(12) United States Patent
Hege et al.

(10) Patent No.: US 9,358,232 B2
(45) Date of Patent: Jun. 7, 2016

(54) METHODS FOR TREATING CANCER USING TOR KINASE INHIBITOR COMBINATION THERAPY

(71) Applicant: Signal Pharmaceuticals, LLC, San Diego, CA (US)

(72) Inventors: Kristen Mae Hege, Burlingame, CA (US); Rajesh Chopra, Summit, NJ (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 73 days.

(21) Appl. No.: 14/254,010

(22) Filed: Apr. 16, 2014

(65) Prior Publication Data

US 2014/0314751 A1     Oct. 23, 2014

Related U.S. Application Data

(60) Provisional application No. 61/908,389, filed on Nov. 25, 2013, provisional application No. 61/813,100, filed on Apr. 17, 2013.

(51) Int. Cl.
| | | |
|---|---|---|
| *A61K 31/4985* | (2006.01) | |
| *A61K 31/505* | (2006.01) | |
| *A61K 39/395* | (2006.01) | |
| *A61K 45/06* | (2006.01) | |
| *C07K 16/28* | (2006.01) | |

(52) U.S. Cl.
CPC ........... *A61K 31/505* (2013.01); *A61K 31/4985* (2013.01); *A61K 39/39558* (2013.01); *A61K 45/06* (2013.01); *C07K 16/2887* (2013.01)

(58) Field of Classification Search
CPC .......................... A61K 31/4985; A61K 31/505
See application file for complete search history.

(56) References Cited

U.S. PATENT DOCUMENTS

| | | | |
|---|---|---|---|
| 3,507,866 | A | 4/1970 | Jones et al. |
| 3,567,725 | A | 3/1971 | Grabowski et al. |
| 4,294,836 | A | 10/1981 | Lesher et al. |
| 4,294,837 | A | 10/1981 | Lesher et al. |
| 4,309,537 | A | 1/1982 | Lesher et al. |
| 4,317,909 | A | 3/1982 | Lesher et al. |
| 4,898,872 | A | 2/1990 | Campbell et al. |
| 4,963,561 | A | 10/1990 | Lesher et al. |
| 5,424,311 | A | 6/1995 | Billhardt-Troughton et al. |
| 5,869,659 | A | 2/1999 | Stolle et al. |
| 6,031,105 | A | 2/2000 | Wright |
| 6,093,728 | A | 7/2000 | McMahon et al. |
| 6,372,740 | B1 | 4/2002 | Murata et al. |
| 6,566,367 | B2 | 5/2003 | Bakthavatchalam et al. |
| 6,791,006 | B2 | 9/2004 | Nezu et al. |
| 6,800,436 | B1 | 10/2004 | Jenne et al. |
| 6,855,723 | B2 | 2/2005 | McMahon et al. |
| 7,608,622 | B2 | 10/2009 | Liu et al. |
| 8,110,578 | B2 * | 2/2012 | Perrin-Ninkovic .. C07D 487/04 514/252.11 |
| 8,372,976 | B2 | 2/2013 | Mortensen et al. |
| 8,383,634 | B2 | 2/2013 | Mortensen et al. |
| 8,492,381 | B2 | 7/2013 | Perrin-Ninkovic et al. |
| 2003/0036652 | A1 | 2/2003 | Bakthavatchalam et al. |
| 2003/0162968 | A1 | 8/2003 | Cirillo et al. |
| 2004/0023921 | A1 | 2/2004 | Hong et al. |
| 2004/0063658 | A1 | 4/2004 | Roberts et al. |
| 2004/0097485 | A1 | 5/2004 | Burkitt et al. |
| 2005/0009737 | A1 | 1/2005 | Clark |
| 2006/0004014 | A1 | 1/2006 | Hoffmann et al. |
| 2006/0135511 | A1 | 6/2006 | Burgey |
| 2006/0142269 | A1 | 6/2006 | Dykes |
| 2006/0211702 | A1 | 9/2006 | Oslob et al. |
| 2007/0036793 | A1 | 2/2007 | Hardie et al. |
| 2007/0112005 | A1 | 5/2007 | Chen et al. |
| 2008/0194019 | A1 | 8/2008 | Cantley et al. |
| 2008/0214580 | A1 | 9/2008 | Neagu et al. |
| 2009/0023724 | A1 | 1/2009 | Mortensen et al. |
| 2009/0042890 | A1 | 2/2009 | Mortensen et al. |
| 2009/0069289 | A1 | 3/2009 | Neagu et al. |
| 2009/0163545 | A1 | 6/2009 | Goldfarb |
| 2009/0181963 | A1 | 7/2009 | Wyeth |
| 2009/0281075 | A1 | 11/2009 | Roughton et al. |
| 2010/0029610 | A1 | 2/2010 | Singh et al. |
| 2010/0144738 | A1 | 6/2010 | Bornmann et al. |
| 2010/0216781 | A1 | 8/2010 | Perrin-Ninkovic et al. |
| 2010/0249122 | A1 | 9/2010 | Kalman |
| 2011/0137028 | A1 | 6/2011 | Harris et al. |
| 2011/0257167 | A1 | 10/2011 | Chopra et al. |
| 2011/0318336 | A1 | 12/2011 | Petricoin, III et al. |
| 2012/0028972 | A1 | 2/2012 | Wong et al. |
| 2012/0077832 | A1 * | 3/2012 | Witowski ............. C07D 239/48 514/275 |
| 2013/0102613 | A1 | 4/2013 | Xu et al. |

(Continued)

FOREIGN PATENT DOCUMENTS

| | | |
|---|---|---|
| CA | 2 458 699 | 3/2003 |
| DE | 262 026 | 11/1988 |
| EP | 0 385 850 | 9/1990 |
| JP | 63275582 | 5/1987 |
| JP | 2001048882 | 2/2001 |
| JP | 2002100363 | 4/2002 |
| JP | 2002167387 | 6/2002 |
| WO | WO 03/032989 | 4/1903 |
| WO | WO 2004/042002 | 5/1904 |
| WO | WO 99/16438 | 4/1999 |

(Continued)

OTHER PUBLICATIONS

Jordan, V. C. Nature Reviews: Drug Discovery, vol. 2, 2003, pp. 205-213.*

(Continued)

*Primary Examiner* — James D Anderson
(74) *Attorney, Agent, or Firm* — Jones Day

(57) ABSTRACT

Provided herein are methods for treating or preventing a cancer, comprising administering an effective amount of a TOR kinase inhibitor and an effective amount of N-(3-(5-fluoro-2-(4-(2-methoxyethoxy)phenylamino)pyrimidin-4-ylamino)phenyl)acrylamide to a patient having a cancer.

6 Claims, 3 Drawing Sheets

(56) References Cited

U.S. PATENT DOCUMENTS

Figure 1:
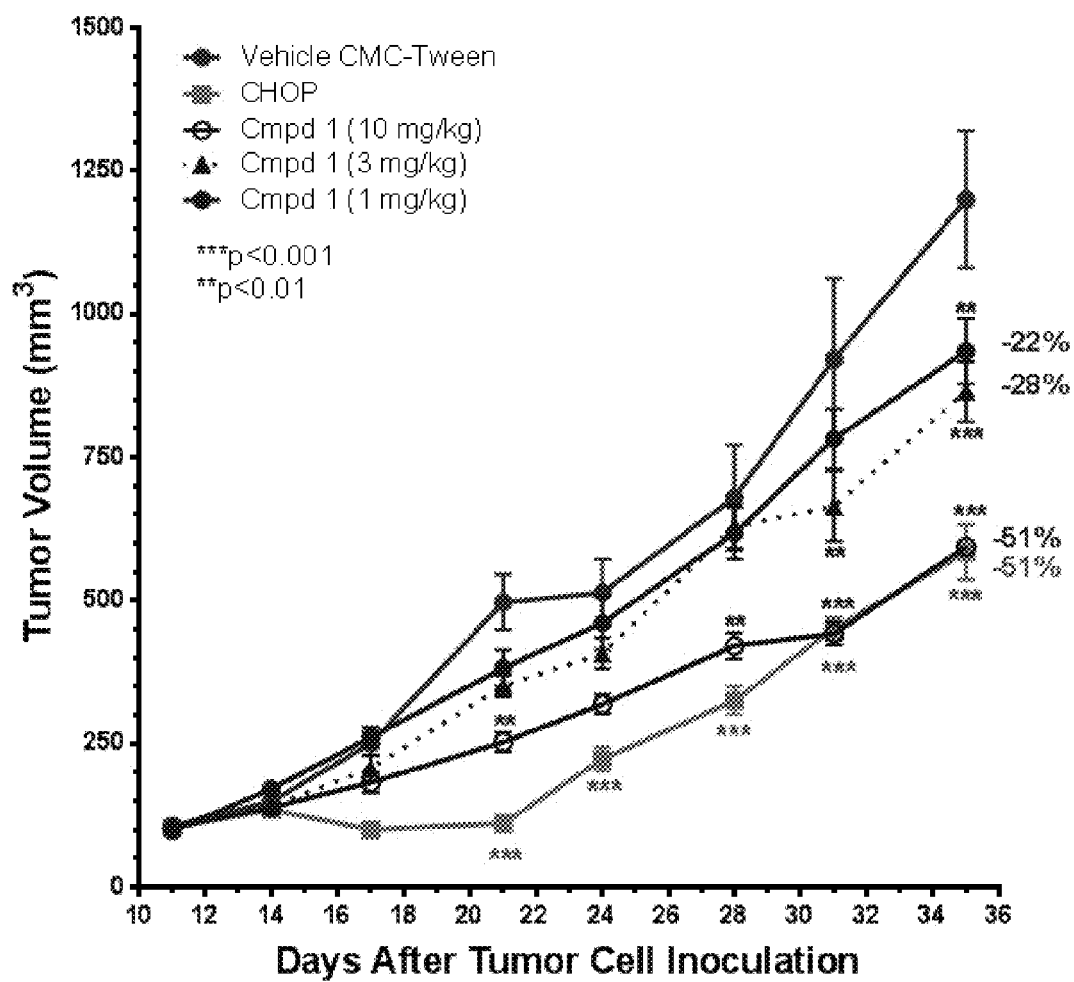

| | | | |
|---|---|---|---|
| 2013/0142873 | A1 | 6/2013 | Assaf et al. |
| 2013/0158023 | A1 | 6/2013 | Ning et al. |
| 2013/0225518 | A1 | 8/2013 | Xu et al. |
| 2013/0245026 | A1 | 9/2013 | Xu et al. |
| 2013/0245027 | A1 | 9/2013 | Xu et al. |
| 2013/0245028 | A1 | 9/2013 | Xu et al. |
| 2013/0245029 | A1 | 9/2013 | Xu et al. |

FOREIGN PATENT DOCUMENTS

| | | |
|---|---|---|
| WO | WO 99/28320 | 6/1999 |
| WO | WO 99/28459 | 6/1999 |
| WO | WO 00/73306 | 12/2000 |
| WO | WO 02/48152 | 6/2002 |
| WO | WO 02/076954 | 10/2002 |
| WO | WO 03/032989 | 4/2003 |
| WO | WO 03/072557 | 9/2003 |
| WO | WO 03/093290 | 11/2003 |
| WO | WO 2004/042002 | 5/2004 |
| WO | WO 2004/048365 | 6/2004 |
| WO | WO 2004/065378 | 8/2004 |
| WO | WO 2004/076454 | 9/2004 |
| WO | WO 2004/078754 | 9/2004 |
| WO | WO 2004/085409 | 10/2004 |
| WO | WO 2004/096797 | 11/2004 |
| WO | WO 2005/003147 | 1/2005 |
| WO | WO 2005/021519 | 3/2005 |
| WO | WO 2005/120511 | 12/2005 |
| WO | WO 2006/001266 | 1/2006 |
| WO | WO 2006/018182 | 2/2006 |
| WO | WO 2006/030031 | 3/2006 |
| WO | WO 2006/036883 | 4/2006 |
| WO | WO 2006/045828 | 5/2006 |
| WO | WO 2006/046031 | 5/2006 |
| WO | WO 2006/050076 | 5/2006 |
| WO | WO 2006/065703 | 6/2006 |
| WO | WO 2006/087530 | 8/2006 |
| WO | WO 2006/090167 | 8/2006 |
| WO | WO 2006/090169 | 8/2006 |
| WO | WO 2006/091737 | 8/2006 |
| WO | WO 2006/108103 | 10/2006 |
| WO | WO 2007/044698 | 4/2007 |
| WO | WO 2007/044729 | 4/2007 |
| WO | WO 2007/044813 | 4/2007 |
| WO | WO 2007/047754 | 4/2007 |
| WO | WO 2007/060404 | 5/2007 |
| WO | WO 2007/066099 | 6/2007 |
| WO | WO 2007/066102 | 6/2007 |
| WO | WO 2007/080382 | 7/2007 |
| WO | WO 2007/125321 | 11/2007 |
| WO | WO 2007/129044 | 11/2007 |
| WO | WO 2007/129052 | 11/2007 |
| WO | WO 2007/129161 | 11/2007 |
| WO | WO 2007/135398 | 11/2007 |
| WO | WO 2008/016669 | 2/2008 |
| WO | WO 2008/023161 | 2/2008 |
| WO | WO 2008/032027 | 3/2008 |
| WO | WO 2008/032028 | 3/2008 |
| WO | WO 2008/032033 | 3/2008 |
| WO | WO 2008/032036 | 3/2008 |
| WO | WO 2008/032060 | 3/2008 |
| WO | WO 2008/032064 | 3/2008 |
| WO | WO 2008/032072 | 3/2008 |
| WO | WO 2008/032077 | 3/2008 |
| WO | WO 2008/032089 | 3/2008 |
| WO | WO 2008/032091 | 3/2008 |
| WO | WO 2008/051493 | 5/2008 |
| WO | WO 2008/064093 | 5/2008 |
| WO | WO 2008/115974 | 9/2008 |
| WO | WO 2008/140947 | 11/2008 |
| WO | WO 2009/007748 | 1/2009 |
| WO | WO 2009/007750 | 1/2009 |
| WO | WO 2009/007751 | 1/2009 |
| WO | WO 2009/052145 | 4/2009 |
| WO | WO 2009/102986 | 8/2009 |
| WO | WO 2010/006072 | 1/2010 |
| WO | WO 2010/062571 | 6/2010 |
| WO | WO 2010/068483 | 6/2010 |
| WO | WO 2011/031965 | 3/2011 |
| WO | WO 2011/079114 | 6/2011 |
| WO | WO 2011/097333 | 8/2011 |
| WO | WO 2012/021444 | 2/2012 |
| WO | WO 2013/063401 | 5/2013 |
| WO | WO 2014/081714 | 5/2014 |

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*

Vippagunta, et al. Advanced Drug Delivery Reviews, 48, 2001, pp. 3-26.*

Wolff, Manfred E., Ed. Burger's Medicinal Chemistry and Drug Discovery—Fifth Edition, New York: John Wiley & Sons, 1996, 1, pp. 975-977.*

Wolff, Manfred E., Ed. Burger's Medicinal Chemistry and Drug Discovery—Fifth Edition, New York: John Wiley & Sons, 1996, 1, 975-976).*

Staudt et al. Blood (ASH Annual Meeting Abstracts), 2001, vol. 118, Abstract 2716 (Abstract attached).*

Wanner et al. British Journal of Haematology, 2006, vol. 134, pp. 475-484.*

Barnes et al. Haematoligica, 2013, vol. 98, No. 4, pp. 615-619 (Published Online Nov. 9, 2012).*

U.S. Appl. No. 14/055,995, Oct. 17, 2013, Signal Pharmaceutical, LLC.

U.S. Appl. No. 14/254,001, Apr. 16, 2014, Signal Pharmaceutical, LLC.

U.S. Appl. No. 14/254,004, Apr. 16, 2014, Signal Pharmaceutical, LLC.

U.S. Appl. No. 14/254,009, Apr. 16, 2014, Signal Pharmaceutical, LLC.

U.S. Appl. No. 14/254,015, Apr. 16, 2014, Signal Pharmaceutical, LLC.

U.S. Appl. No. 14/254,017, Apr. 16, 2014, Signal Pharmaceutical, LLC.

U.S. Appl. No. 14/254,019, Apr. 16, 2014, Signal Pharmaceutical, LLC.

U.S. Appl. No. 14/254,020, Apr. 16, 2014, Signal Pharmaceutical, LLC.

U.S. Appl. No. 14/254,023, Apr. 16, 2014, Signal Pharmaceutical, LLC.

Barlin 1982, "Purine analogs as amplifiers of phleomycin. VII. Some 1H-inidazo[4,5-b]pyrazines and related compound," Australian Journal of Chemistry, vol. 35:2299-2306.

Beresnev et al., 2000, "Interaction of 5-methoxy-1,2,4-traizines with uras as a new route to 6-azapurines," Medeleev Commu., vol. 2:58-59.

Bergmann et al., 1963, "2-Phenylpurines, their chemical and enzumological reactivity," J. Chem Org. , pp. 3729-3735.

Booth et al., 1992, "Synthesis of 9-Hydroxyalkyl-substituted purines from the corresponding 4-(C-Cyanoformimidoyl)imidazole-5-amines," J, Chem Society, Perkin Transactions 1: Organic and Bio-Organic Chemstry, vol. 2119-26.

Booth et al., 1995, "Synthesis of [1α, 2B,3α-2,3-bis(benzyloxymethyl)cyclobutl]imidazol-5-amines: important precursors to cyclobut-A derivatives," J. Chem Society, Perkin Tranactions 1: Organic and Bio-Organic Chemistry, vol. 6, pp. 669-75.

Booth et al., 2001, "The Reactions of Diaminomaleonitrile with Isocyanates and Either Aldehydes or Ketones Revisited," J. Org Chem, vol. 66:8436-8441.

Booth, et al., 1994, "Synthesis of 4- and 5-Disubstituted 1-Benzylimidazoles, Important Precursors of Purine Analogs," J. of Heterocyclic of Chemistry, vol. 31(2):345-50.

Carretero et al. 2010, "Integrative Genomic and Proteomic Analyses Indentity Targets for Lkb1-Deficient Metastatic Lung Tumors," Cancer Cell, vol. 17(6): 547-559.

(56) References Cited

OTHER PUBLICATIONS

Chupakhin et al., 2001, "A simple one pot synthesis of condensed 1,2,4-triazines by using the tandem $A_n$-$S_N$ipso and $S_n^h$—$S_N$ipso reactions," J. of Heterocyclic Chemistry, vol. 38(4):901-907.
Cohen, P. 2001, "The role of protein phosphorylation in human health and disease," Eur. J. Biochem, vol. 268:5001-5010.
Cohen, P. 2002, "Protein kinases—the major drug targets of the twenty-first century?" Nature Reviews/Drug Discovery, vol. 1:309-315.
Cohen, 2005, *Protein Kinase Inhibitors for the Treatment of Disease: The Promise and the Problems*, Handbook of Experimental Pharmacology, Springer Berlin Heidelberg, 167:1-7.
Coish, et al., 2006, "Small molecule inhibitors of IKK kinase activity," Expert Opin. Ther. Patents, vol. 16(1):1-12.
Crofts et al., 1997 "Metabolism of 2-amino-1-methyl-6-phenylimidazo [4,5-b]pyridine (PhIP) by human cytochrome P4501B1," Carcinogenesis, vol. 18(9):1793-1798.
Dang et al., 1999, "Efficient synthesis of purines and purine nucelosides via an inverse electron demand diels—alder reaction," J. Am Chem Soc., vol. 121(24):5833-5834.
Database CAPLUS Online Chemical Abstracts Service, Columbus, Ohio, Database Accession No. 1951:49974 (XP-002472261) (1951).
Database CAPLUS Online Chemical Abstracts Service, Columbus, Ohio, Database Accession No. 1978:433195 (XP-002472262) (1978).
Database CAPLUS Online Chemical Abstracts Service, Columbus, Ohio, Database Accession No. 1966:26849 (XP-002472263) (1965).
Dornow et al., 1957, "Synthese von2-Oxy-imidazolo-(5',4':2,3)-pyridinen)," Arch Pharm. vol. 290, pp. 20-31 (w/English language abstract).
Dzierba et al., 2004, "Synthesis, structure-activity relationships, and in vivo properties of 3,4-dihydro-1H-pyrido[2,3-b]pyrazin-2-ones as corticotropin-releasing factor-1 receptor antagonists," J of Medicinal Chemistry, vol. 47, pp. 5783-5790.
Fabbro et al., 2002, "Protein kinases as targets for anticancer agents: from inhibitors to useful drugs," Pharmacol Ther., 93(2-3):79-98.
Farhadi et al., 2006, "The role of protein kinase C isoforms in modulating injury and repair of the intestinal barrier," J. Pharm Exp. Ther., vol. 316(1):1-7.
Frandsen et al., 1992, "Reaction of the N2-acetoxy derivative of 2-amino-1-methyl-6-phenylimidazo[4,5,b] pyridine . . . ," Carcinogenesis, vol. 13(4):629-635.
Gao et al., 2010, "LKB1 inhibits lung cancer progression through lysyl oxidase and extracellular matrix remodeling," Proceedings of the National Academy of Sciences, vol. 107(44): 18892-18897.
Georgakis and Younes, 2006, "From rapi nui to rapamycin: targeting PI3K/Akt/mTOR for cancer therapy," Expert Rev. Anticancer Ther., vol. 6(1):131-140.
Grimmiger et al., 2010, "Targeting non-malignant disorders with tyrosine kinase inhibitors," Nat. Rev. Drug Disc., 9(12):956-970.
Hamad, 2001, "A new synthesis of 4-cyano-1,3-dihydro-2-oxo-2*H*-imidazole-5-($N^1$-tosyl)carboxamide: Reactive precursor for thiopurine analogues," J of Heterocyclic Chemistry, vol. 38(4):939-944.
Hernan et al., "De novo germline mutation in the serine-threonine kinase STK11/LKB1 gene associated with Peutz-Jeghers syndrome," Clin Genet., 66(1):58-62.
Huang et al., 2010, "Genetic and epigenetic silencing of SCARA5 may contribute to human hepatocellular carcinoma by activating FAK signaling," Journal of Clinical Investigation, American Society for Clinical investigation, vol. 120(1): 223-241.
Inge et al., 2009, "Expression of LKB1 tumor suppressor in non-small cell lung cancer determines sensitivity to 2-deoxyglucose," Journal of Thoracic and Cardiovascular Surgery, vol. 137(3): 580-586.
Irie et al., 2005, "Toward the development of new medicinal leads with selectivity for protein kinase C isozymes," The Chemical Record, vol. 5:185-195.

Itoh et al., 2004, "A novel practical synthesis of C-2-arylpurines," Advanced Synthesis & Catalysis, vol. 346:1859-1867.
Ji et al., 2007, "LKB1 modulates lung cancer differentiation and metastasis," Nature, 448(7155):807-810.
Jones et al., 1973, "6-Substituted-5-chloro-1,3-dihydro-2H-imidazo(4,5-b)pyrazin-2-ones with hypotensive activity," J. Med. Chem., vol. 16(5):537-542.
Kazaoka et al., 2003, "Synthesis of 6-substituted 9-benzyl-8-hydroxypurines with potential interferon-indcuing activity," Chemical & Pharmaceutical Bulletin, vol. 51(5):608-611.
Killday et al., 2001, "Microxine, a new cdc2 kinase inhibitor from the Australian marine sponge Microxina species," J. of Natural Products, vol. 64(4):525-526.
Mahoney et al., 2009, "LKB1/KRAS mutant lung cancers constitute a genetic subset of NSCLC with increased sensitivity to MAPK and mTOR signalling inhibition," Br J Cancer, 100(2):370-375.
Minehan et al., 2000, "Molecular recognition of DNA by Hoechst Benzimidazoles: Exploring beyond theopyrrole-imidazole-hydroxypyrrole polyamide-pairing code," Helvitica Chima Acta, vol. 83(9):2197-2213.
Nagashima et al., 2004, "Solution-Phase parallel synthesis of an N-Alkylated dihydropteridinone library from fluorous amino acids," J of Comb. Chemistry, vol. 6(6):942-949.
Park et al., 2000, "A novel mechanism of TRAF signaling revealed by structural and functional analyses of the TRADD-TRAF2 interaction," Cell, vol. 101:777-787.
Patani et al., 1998, "Bioisosterim: A rational approach in drug design," Chemical Reviews, vol. 96:3147-3176.
PCT Annex to Form PCT/ISA?206 Communication Relating to the Results of the Partial International Search issued in connection with PCT/US2012/049281,filed Aug. 2, 2012.
PCT International Search Report issued in connection with PCT/US2012/049281, filed Aug. 2, 2012.
PCT Written Opinion of the International Searching Authority issued in connection with PCT/US2012/049281, filed Aug. 2, 2012.
Registry File Document for RN 863501-03-5, 863502-39-0 and others (Sep. 20, 2005).
Yuan et al., 2009, "Targeting tumorigenesis: development and use of mTOR inhibitors in cancer therapy," Journal of Hematology & Oncology, Biomed Central Ltd., London UK, vol. 2(1): 45.
Seela et al., 2004, "Product Class 17: Purines," Science of Synthesis, vol. 16, pp. 945-1108.
Shaw et al., 2004, "The LKB1 tumor suppressor negativiely regulates mTOR signaling," Cancer Cell, vol. 6(1): 91-99.
Shaw et al., 2009, "LKB1 and AMP-activated protein kinase control of mTOR signalling and growth," Acta. Physiol (Oxf.) 196(1):65-80.
Singh et al., 1994, "Novel cAMP PDE III Inhibitors: Imidazo[4,5-b]pyridin-2(3H)-ones and Thiazolo[4,5- b]pyridin-2(3h)-ones and Their Analogs," J. Med. Chem, vol. 37(2):248-54.
Sridhar et al., 2000, "Protein kinases as therapeutic targets," Pharm. Res., 17(11):1345-1353.
Wallace 2008, "Palladium-catalyzed synthesis of quinoxaline derivatives," Tetrahedron, vol. 64:9675-9684.
Wei et al., 2009, "Chemopreventive efficacy of rapamycin on Peutz-Jeghers syndrome in a mouse model," Cancer Lett., 277(2):149-154.
Westover et al., 1981, "Synthesis and antiviral activity of certain 9-β-D-Riofuranoaylpurine-6-carboxamides," J.Med. Chem., vol. 24(8):941-46.
Wingo et al., 2009, "Somatic LKB1 mutations promote cervical cancer progression," PloS One, 4(4):1-8.
Gao et al.: 2011, "LKB1 in lung cancerigenesis: a serine/threonine kinase as tumor suppressor," Protein & Cell, Gaodeng Jiaoyu Chubanshe, China, vol. 2(2): 99-107.
Yoneda et al., 1976, "A transformationof 7-azapteridines into 6-azapurines (Imidazo[4,5-e]-as -triazines)," Heterocycles, vol. 4(9):1503-1508.
Yoneda et al., 1978, "Synthesis of imadazo[4,5-e]-as-triazine (6-Azapurine) Derivatives," Chem & Pharm Bulletin, vol. 26(10):3154-3160.
Zaki et al., 2007, "The synthesis of imidazol[4,5-d]pyridines from a substituted imidazole and acyl or sulfonyl acetonitrile," Tetrahedron, vol. 63(18):3745-3753.

(56) References Cited

OTHER PUBLICATIONS

Zhong et al., 2006, "LKB1 mutation in large cell carcinoma of the lung," Cancer Lung, vol. 53(3):285-294.

Shoji et al. 2012, "Genotype-dependent efficacy of a dual PI3K/mTOR inhibitor, NVP-BEZ235, and an mTOR inhibitor, RAD001, in endometrial carcinomas." *PloS one* 7.5, 2012, e37431.

Gini et al., 2013, "The mTOR Kinase Inhibitors, CC214-1 and CC214-2, Preferentially Block the Growth of EGFRvIII-Activated Glioblastomas," Clin Cancer Res 2013;19:5722-5732.

Choi et al., 2012, "Inhibitors of B-Cell Receptor Signaling for Patients With B-Cell Malignancies," Jan. 1, 2012, pp. 404-410, vol. 18, No. 5, The Cancer Journal.

Costa et al., 2007, "Aspects of mTOR biology and the use of mTOR inhibitors in non-Hodgkin's lymphoma," Jan. 26, 2007, pp. 78-84, vol. 33, No. 1, Cancer Treatment Reviews, Saunders, US.

Johnson et al., 2003, "Advances in the therapy of chronic lymphocytic leukemia," Jul. 1, 2003, pp. 297-305, vol. 10, No. 4, Current opinion in Hematology, Philadelphia, US.

\* cited by examiner

METHODS FOR TREATING CANCER USING TOR KINASE INHIBITOR COMBINATION THERAPY

This application claims the benefit of U.S. Provisional Application No. 61/813,100, filed Apr. 17, 2013 and U.S. Provisional Application No. 61/908,389, filed Nov. 25, 2013, the entire contents of which are incorporated herein by reference.

1. FIELD

Provided herein are methods for treating or preventing a cancer comprising administering an effective amount of a TOR kinase inhibitor and an effective amount of N-(3-(5-fluoro-2-(4-(2-methoxyethoxy)phenylamino)pyrimidin-4-ylamino)phenyl)acrylamide to a patient having a cancer.

2. BACKGROUND

The connection between abnormal protein phosphorylation and the cause or consequence of diseases has been known for over 20 years. Accordingly, protein kinases have become a very important group of drug targets. See Cohen, *Nature*, 1:309-315 (2002). Various protein kinase inhibitors have been used clinically in the treatment of a wide variety of diseases, such as cancer and chronic inflammatory diseases, including diabetes and stroke. See Cohen, *Eur. J. Biochem.*, 268:5001-5010 (2001), *Protein Kinase Inhibitors for the Treatment of Disease: The Promise and the Problems*, Handbook of Experimental Pharmacology, Springer Berlin Heidelberg, 167 (2005).

The protein kinases are a large and diverse family of enzymes that catalyze protein phosphorylation and play a critical role in cellular signaling. Protein kinases may exert positive or negative regulatory effects, depending upon their target protein. Protein kinases are involved in specific signaling pathways which regulate cell functions such as, but not limited to, metabolism, cell cycle progression, cell adhesion, vascular function, apoptosis, and angiogenesis. Malfunctions of cellular signaling have been associated with many diseases, the most characterized of which include cancer and diabetes. The regulation of signal transduction by cytokines and the association of signal molecules with protooncogenes and tumor suppressor genes have been well documented. Similarly, the connection between diabetes and related conditions, and deregulated levels of protein kinases, has been demonstrated. See e.g., Sridhar et al. *Pharmaceutical Research*, 17(11):1345-1353 (2000). Viral infections and the conditions related thereto have also been associated with the regulation of protein kinases. Park et al. *Cell* 101 (7): 777-787 (2000).

Because protein kinases regulate nearly every cellular process, including metabolism, cell proliferation, cell differentiation, and cell survival, they are attractive targets for therapeutic intervention for various disease states. For example, cell-cycle control and angiogenesis, in which protein kinases play a pivotal role are cellular processes associated with numerous disease conditions such as but not limited to cancer, inflammatory diseases, abnormal angiogenesis and diseases related thereto, atherosclerosis, macular degeneration, diabetes, obesity, and pain.

Protein kinases have become attractive targets for the treatment of cancers. Fabbro et al., *Pharmacology & Therapeutics* 93:79-98 (2002). It has been proposed that the involvement of protein kinases in the development of human malignancies may occur by: (1) genomic rearrangements (e.g., BCR-ABL in chronic myelogenous leukemia), (2) mutations leading to constitutively active kinase activity, such as acute myelogenous leukemia and gastrointestinal tumors, (3) deregulation of kinase activity by activation of oncogenes or loss of tumor suppressor functions, such as in cancers with oncogenic RAS, (4) deregulation of kinase activity by over-expression, as in the case of EGFR and (5) ectopic expression of growth factors that can contribute to the development and maintenance of the neoplastic phenotype. Fabbro et al., *Pharmacology & Therapeutics* 93:79-98 (2002).

The elucidation of the intricacy of protein kinase pathways and the complexity of the relationship and interaction among and between the various protein kinases and kinase pathways highlights the importance of developing pharmaceutical agents capable of acting as protein kinase modulators, regulators or inhibitors that have beneficial activity on multiple kinases or multiple kinase pathways. Accordingly, there remains a need for new kinase modulators.

The protein named mTOR (mammalian target of rapamycin), which is also called FRAP, RAFT1 or RAPT1), is a 2549-amino acid Ser/Thr protein kinase, that has been shown to be one of the most critical proteins in the mTOR/PI3K/Akt pathway that regulates cell growth and proliferation. Georgakis and Younes *Expert Rev. Anticancer Ther.* 6(1):131-140 (2006). mTOR exists within two complexes, mTORC1 and mTORC2. While mTORC1 is sensitive to rapamycin analogs (such as temsirolimus or everolimus), mTORC2 is largely rapamycin-insensitive. Notably, rapamycin is not a TOR kinase inhibitor. Several mTOR inhibitors have been or are being evaluated in clinical trials for the treatment of cancer. Temsirolimus was approved for use in renal cell carcinoma in 2007 and sirolimus was approved in 1999 for the prophylaxis of renal transplant rejection. Everolimus was approved in 2009 for renal cell carcinoma patients that have progressed on vascular endothelial growth factor receptor inhibitors, in 2010 for subependymal giant cell astrocytoma (SEGA) associated with tuberous sclerosis (TS) in patients who require therapy but are not candidates for surgical resection, and in 2011 for progressive neuroendocrine tumors of pancreatic origin (PNET) in patients with unresectable, locally advanced or metastatic disease. There remains a need for TOR kinase inhibitors that inhibit both mTORC1 and mTORC2 complexes.

DNA-dependent protein kinase (DNA-PK) is a serine/threonine kinase involved in the repair of DNA double strand breaks (DSBs). DSBs are considered to be the most lethal DNA lesion and occur endogenously or in response to ionizing radiation and chemotherapeutics (for review see Jackson, S. P., Bartek, J. The DNA-damage response in human biology and disease. Nature Rev 2009; 461:1071-1078). If left unrepaired, DSBs will lead to cell cycle arrest and/or cell death (Hoeijmakers, J. H. J. Genome maintenance mechanisms for preventing cancer. Nature 2001; 411: 366-374; van Gent, D. C., Hoeijmakers, J. H., Kanaar, R. Chromosomal stability and the DNA double-stranded break connection. *Nat Rev Genet.* 2001; 2: 196-206). In response to the insult, cells have developed complex mechanisms to repair such breaks and these mechanisms may form the basis of therapeutic resistance. There are two major pathways used to repair DSBs, non-homologous end joining (NHEJ) and homologous recombination (HR). NHEJ brings broken ends of the DNA together and rejoins them without reference to a second template (Collis, S. J., DeWeese, T. L., Jeggo P. A., Parker, A. R. The life and death of DNA-PK. Oncogene 2005; 24: 949-961). In contrast, HR is dependent on the proximity of the sister chromatid which provides a template to mediate faithful repair (Takata, M., Sasaki, M. S., Sonoda, E., Morrison, C., Hashimoto, M., Utsumi, H., et al. Homologous recombination and non-homologous end joining pathways of DNA double-strand break repair have overlapping roles in the maintenance of chromosomal integrity in vertebrate cells. EMBO J. 1998; 17: 5497-5508; Haber, J. E. Partners and pathways repairing a double-strand break. Trends Genet. 2000; 16: 259-264). NHEJ repairs the majority of DSBs. In NHEJ, DSBs are recognized by the Ku protein that binds and then activates the catalytic subunit of DNA-PK. This leads to recruitment and activation of end-processing enzymes, polymerases and DNA ligase IV (Collis, S. J., DeWeese, T. L., Jeggo P. A., Parker, A. R. The life and death of DNA-PK. Oncogene 2005; 24: 949-961). NHEJ is primarily controlled by DNA-PK and thus inhibition of DNA-PK is an attractive approach to modulating the repair response to exogenously induced DSBs. Cells deficient in components of the NHEJ pathway are defective in DSB repair and highly sensitive to ionizing radiation and topoisomerase poisons (reviewed by Smith, G. C. M., Jackson, S. P. The DNA-dependent protein kinase. Genes Dev 1999; 13: 916-934; Jeggo, P. A., Caldecott, K., Pidsley, S., Banks, G. R. Sensitivity of Chinese hamster ovary mutants defective in DNA double strand break repair to topoisomerase II inhibitors. Cancer Res 1989; 49: 7057-7063). A DNA-PK inhibitor has been reported to have the same effect of sensitizing cancer cells to therapeutically induced DSBs (Smith, G. C. M., Jackson, S. P. The DNA-dependent protein kinase. Genes Dev 1999; 13: 916-934).

Bruton's tyrosine kinase (BTK) is a non-receptor tyrosine kinase with restricted cellular expression largely limited to B-lymphocytes, monocytes, and mast cells or basophils. BTK is a critical component of the B-cell receptor (BCR) signaling network and is crucial for B-cell development. Investigation has revealed that some B-cell malignancies, including B-cell non-Hodgkin lymphomas, depend on BCR signaling, suggesting that interruption of such signaling could be a promising therapeutic opportunity. Recently, clinical anti-tumor responses in various B-cell non-Hodgkin lymphoma (B-NHL) and CLL/SLL have been reported with agents that inhibit spleen tyrosine kinase (SYK) and BTK, both components of the BCR signaling pathway.

Recent preclinical research has shown that BTK is an important signaling protein in the pathway for lymphomagenesis, especially in certain types of DLBCL. Recent clinical research has further shown that both lenalidomide and certain BTK inhibitors exhibit activity in DLBCL and MCL.

Citation or identification of any reference in Section 2 of this application is not to be construed as an admission that the reference is prior art to the present application.

3. SUMMARY

Provided herein are methods for treating or preventing a cancer, comprising administering an effective amount of a TOR kinase inhibitor and an effective amount of N-(3-(5-fluoro-2-(4-(2-methoxyethoxy)phenylamino)pyrimidin-4-ylamino)phenyl)acrylamide:

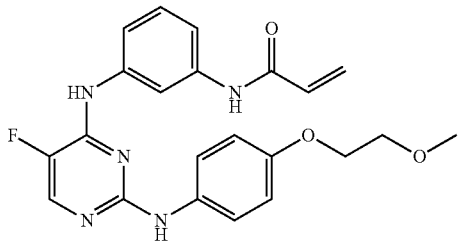

AA or a pharmaceutically acceptable salt thereof (collectively referred to herein as "Compound AA"), to a patient having a cancer. In a particular embodiment, a besylate salt of Compound AA is used in the compositions and methods provided herein. In a particular embodiment, the free base of Compound AA is used in the compositions and methods provided herein.

In certain embodiments, provided herein are methods for achieving an International Workshop on Chronic Lymphocytic Leukemia (IWCLL) response definition of complete response (CR), complete response with incomplete marrow recovery (CRi), partial response (PR), or stable disease (SD) in a patient having chronic lymphocytic leukemia, comprising administering an effective amount of a TOR kinase inhibitor in combination with Compound AA to said patient. In certain embodiments, provided herein are methods for achieving a National Cancer Institute-sponsored Working Group on Chronic Lymphocytic Leukemia (NCI-WG CLL) response definition of complete response (CR), complete response with incomplete marrow recovery (CRi), partial response (PR) or stable disease (SD) in a patient having chronic lymphocytic leukemia, comprising administering an effective amount of a TOR kinase inhibitor in combination with Compound AA to said patient. In certain embodiments, provided herein are methods for achieving an International Workshop Criteria (IWC) for non-Hodgkin's lymphoma of complete response, partial response or stable disease in a patient having non-Hodgkin's lymphoma, comprising administering an effective amount of a TOR kinase inhibitor in combination with Compound AA to said patient. In certain embodiments, provided herein are methods for achieving an International Uniform Response Criteria (IURC) for multiple myeloma of complete response, partial response or stable disease in a patient having multiple myeloma, comprising administering an effective amount of a TOR kinase inhibitor in combination with Compound AA to said patient. In certain embodiments, provided herein are methods for achieving a Response Evaluation Criteria in Solid Tumors (for example, RECIST 1.1) of complete response, partial response or stable disease in a patient having a solid tumor, comprising administering an effective amount of a TOR kinase inhibitor in combination with Compound AA to said patient. In certain embodiments, provided herein are methods for achieving a Prostate Cancer Working Group 2 (PCWG2) Criteria of complete response, partial response or stable disease in a patient having prostate cancer, comprising administering an effective amount of a TOR kinase inhibitor in combination with Compound AA to said patient. In certain embodiments, provided herein are methods for achieving a Responses Assessment for Neuro-Oncology (RANO) Working Group for glioblastoma multiforme of complete response, partial response or stable disease in a patient having glioblastoma multiforme, comprising administering an effective amount of a TOR kinase inhibitor in combination with Compound AA to said patient.

In certain embodiments, provided herein are methods for increasing survival without cancer progression of a patient having a cancer, comprising administering an effective amount of a TOR kinase inhibitor in combination with an effective amount of Compound AA to said patient.

In certain embodiments, the TOR kinase inhibitor is a compound as described herein.

The present embodiments can be understood more fully by reference to the detailed description and examples, which are intended to exemplify non-limiting embodiments.

4. BRIEF DESCRIPTION OF THE DRAWINGS

FIG. 1 depicts the antitumor activity of Compound 1 in the WSU-DLBCL2 xenograft model. Tumor inhibition is shown as a percentage change for each treatment group and represents the difference in average tumor volume between Compound 1-treated mice and vehicle-treated mice on Day 35. The average tumor volumes of all Compound 1-treated groups were significantly smaller than in vehicle-treated control mice on Day 35. At the end of the study on Day 35, approximately 51%, 28% and 22% tumor volume reduction (TVR) was observed at the dose levels of 10, 3 and 1 mg/kg, respectively. No significant body weight loss was observed in mice treated with Compound 1.

Figure 2:
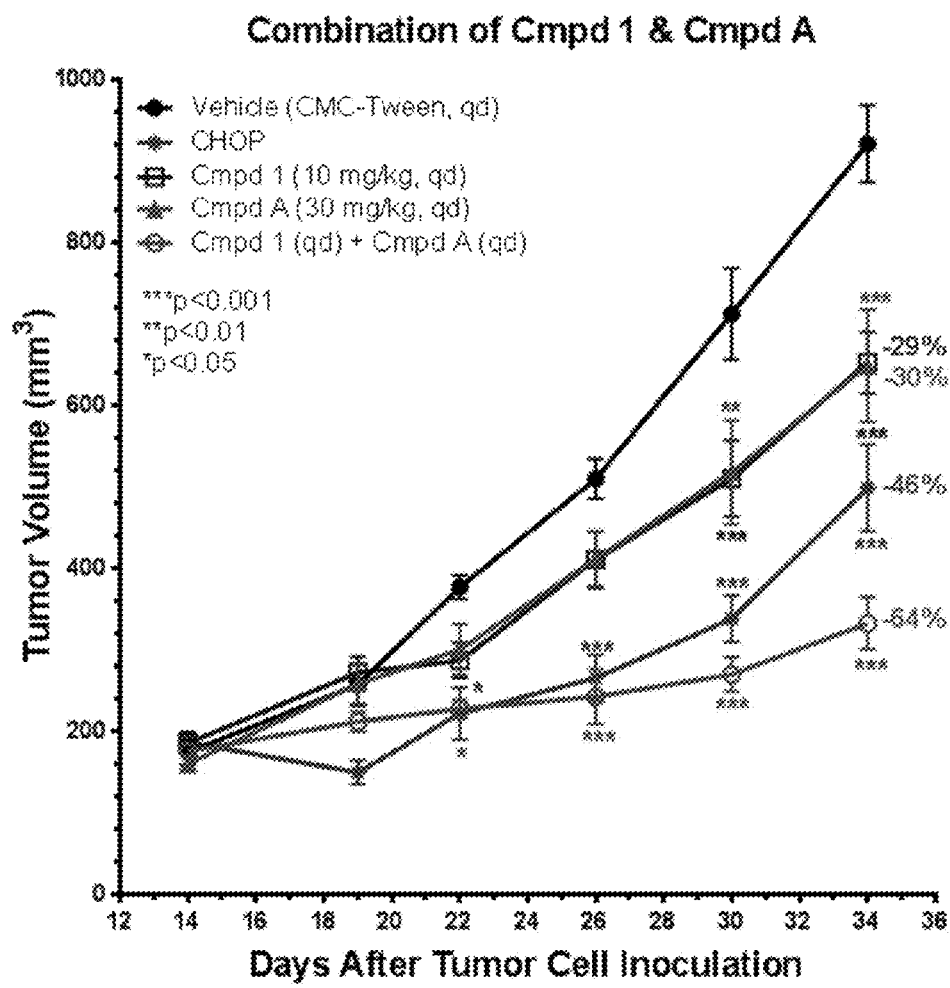

FIG. 2 depicts the antitumor activity of Compound 1 in combination with Compound A in the WSU-DLCL2 xenograft model. Tumor inhibition is shown as a percentage change for each treatment group and represents the difference in average tumor volume between Compound 1- and Compound A-treated mice and vehicle-treated mice on Day 34. Compound 1 at 10 mg/kg yielded a statistically significant ($p<0.001$) decrease in tumor volume of 29% as a single agent treatment. Compound A at 30 mg/kg yielded a statistically significant ($p<0.001$) decrease in tumor volume of 30% as a single agent treatment on day 34. Tumor volumes were further decreased to 64% with Compound 1 in combination with Compound A ($p<0.001$). Using the fractional product method, Compound 1 in combination with Compound A was determined to be synergistic in decreasing tumor volume. In a 2-way ANOVA analysis with a Bonferroni post test, the tumor volumes of animals treated with Compound 1 (10 mg/kg) in combination with Compound A (30 mg/kg) were significantly ($p<0.001$) smaller when compared with the tumors of animals treated with either agent alone. No significant body weight loss was observed in mice treated with Compound 1 or Compound A either as single agents or in combination.

Figure 3:
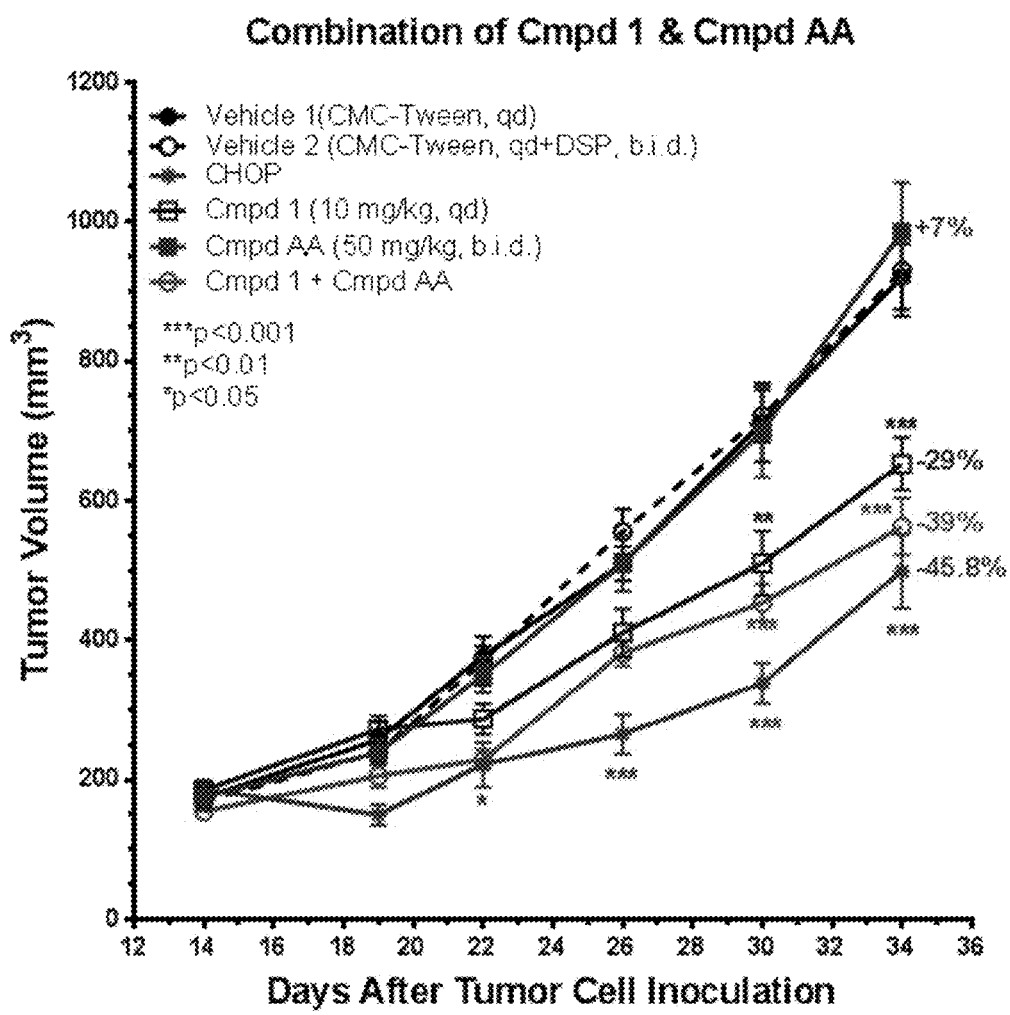

FIG. 3 depicts the antitumor activity of Compound 1 in combination with Compound AA in the WSU-DLCL2 xenograft model. Tumor inhibition is shown as a percentage change for each treatment group and represents the difference in average tumor volume between Compound 1 and Compound AA-treated mice and vehicle-treated mice on Day 34. Compound 1 at 10 mg/kg yielded a statistically significant ($p<0.001$) decrease in tumor volume of 29% as a single agent treatment. No significant antitumor activity of Compound AA at 50 mg/kg (BID) was observed. There was a 39% decrease in the tumor volumes in animals treated with Compound 1 in combination with Compound AA (simultaneous administration) when compared with vehicle control group. In a 2-way ANOVA analysis with a Bonferroni post-test this combination effect of Compound 1 and Compound AA when compared with single agent activity of Compound 1 (10 mg/kg) was not significantly different. No significant body weight loss was observed in mice treated with Compound 1 or Compound AA either as single agents or in combination.

5. DETAILED DESCRIPTION

5.1 Definitions

An "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 or carbon atoms. Representative alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, 2-methylpentyl, 3-methylpentyl, 4-methylpentyl, 2,3-dimethylbutyl and the like. Examples of unsaturated alkyl groups include, but are not limited to, vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, —C≡CH, —C≡C(CH$_3$), —C≡C(CH$_2$CH$_3$), —CH$_2$C≡CH, —CH$_2$C≡C(CH$_3$) and —CH$_2$CC (CH$_2$CH$_3$), among others. An alkyl group can be substituted or unsubstituted. In certain embodiments, when the alkyl groups described herein are said to be "substituted," they may be substituted with any substituent or substituents as those found in the exemplary compounds and embodiments disclosed herein, as well as halogen (chloro, iodo, bromo, or fluoro); hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxylamine; alkoxyamine; aralkoxyamine; N-oxide; hydrazine; hydrazide; hydrazone; azide; isocyanate; isothiocyanate; cyanate; thiocyanate; B(OH)$_2$, or O(alkyl)aminocarbonyl.

An "alkenyl" group is a straight chain or branched non-cyclic hydrocarbon having from 2 to 10 carbon atoms, typically from 2 to 8 carbon atoms, and including at least one carbon-carbon double bond. Representative straight chain and branched (C$_2$-C$_8$)alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl and the like. The double bond of an alkenyl group can be unconjugated or conjugated to another unsaturated group. An alkenyl group can be unsubstituted or substituted.

A "cycloalkyl" group is a saturated, or partially saturated cyclic alkyl group of from 3 to 10 carbon atoms having a single cyclic ring or multiple condensed or bridged rings which can be optionally substituted with from 1 to 3 alkyl groups. In some embodiments, the cycloalkyl group has 3 to 8 ring members, whereas in other embodiments the number of ring carbon atoms ranges from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as adamantyl and the like. Examples of unsaturated cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanone and the like.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aryl ring system having one to four heteroatoms as ring atoms in a heteroaromatic ring system, wherein the remainder of the atoms are carbon atoms. In some embodiments, heteroaryl groups contain 5 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, thiazolyl, pyrolyl, pyridyl, pyridazinyl, pyrimidinyl, pyrazinyl, thiophenyl, benzothiophenyl, furanyl, benzofuranyl (for example, isobenzofuran-1,3-diimine), indolyl, azaindolyl (for example, pyrrolopyridyl or 1H-pyrrolo[2,3-b]pyridyl), indazolyl, benzimidazolyl (for example, 1H-benzo[d]imidazolyl), imidazopyridyl (for example, azabenzimidazolyl, 3H-imidazo[4,5-b]pyridyl or 1H-imidazo[4,5-b]pyridyl), pyrazolopyridyl, triazolopyridyl, benzotriazolyl, benzoxazolyl, benzothiazolyl, benzothiadiazolyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocylyls can also be bonded to other groups at any ring atom (i.e., at any carbon atom or heteroatom of the heterocyclic ring). A heterocyclylalkyl group can be substituted or unsubstituted. Heterocyclyl groups encompass unsaturated, partially saturated and saturated ring systems, such as, for example, imidazolyl, imidazolinyl and imidazolidinyl groups. The phrase heterocyclyl includes fused ring species, including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, pyrrolidyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl (for example, tetrahydro-2H-pyranyl), tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl; for example, 1H-imidazo[4,5-b]pyridyl, or 1H-imidazo[4,5-b]pyridin-2(3H)-onyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

A "cycloalkylalkyl" group is a radical of the formula: -alkyl-cycloalkyl, wherein alkyl and cycloalkyl are defined above. Substituted cycloalkylalkyl groups may be substituted at the alkyl, the cycloalkyl, or both the alkyl and the cycloalkyl portions of the group. Representative cycloalkylalkyl groups include but are not limited to cyclopentylmethyl, cyclopentylethyl, cyclohexylmethyl, cyclohexylethyl, and cyclohexylpropyl. Representative substituted cycloalkylalkyl groups may be mono-substituted or substituted more than once.

An "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and fused (cycloalkylaryl)alkyl groups such as 4-ethyl-indanyl.

A "heterocyclylalkyl" group is a radical of the formula: -alkyl-heterocyclyl, wherein alkyl and heterocyclyl are defined above. Substituted heterocyclylalkyl groups may be substituted at the alkyl, the heterocyclyl, or both the alkyl and the heterocyclyl portions of the group. Representative heterocylylalkyl groups include but are not limited to 4-ethyl-morpholinyl, 4-propylmorpholinyl, furan-2-yl methyl, furan-3-yl methyl, pyrdine-3-yl methyl, (tetrahydro-2H-pyran-4-yl)methyl, (tetrahydro-2H-pyran-4-yl)ethyl, tetrahydrofuran-2-yl methyl, tetrahydrofuran-2-yl ethyl, and indol-2-yl propyl.

A "halogen" is chloro, iodo, bromo, or fluoro.

A "hydroxyalkyl" group is an alkyl group as described above substituted with one or more hydroxy groups.

An "alkoxy" group is —O-(alkyl), wherein alkyl is defined above.

An "alkoxyalkyl" group is -(alkyl)-O-(alkyl), wherein alkyl is defined above.

An "amine" group is a radical of the formula: —NH$_2$.

A "hydroxylamine" group is a radical of the formula: —N(R$^{\#}$)OH or —NHOH, wherein R$^{\#}$ is a substituted or unsubstituted alkyl, cycloalkyl, cycloalkylalkyl, aryl, aralkyl, heterocyclyl or heterocyclylalkyl group as defined herein.

An "alkoxyamine" group is a radical of the formula: —N(R$^{\#}$)O-alkyl or —NHO-alkyl, wherein R$^{\#}$ is as defined above.

An "aralkoxyamine" group is a radical of the formula: —N(R$^{\#}$)O-aryl or —NHO-aryl, wherein R$^{\#}$ is as defined above.

An "alkylamine" group is a radical of the formula: —NH-alkyl or —N(alkyl)$_2$, wherein each alkyl is independently as defined above.

An "aminocarbonyl" group is a radical of the formula: —C(=O)N(R$^{\#}$)$_2$, —C(=O)NH(R$^{\#}$) or —C(=O)NH$_2$, wherein each R$^{\#}$ is as defined above.

An "acylamino" group is a radical of the formula: —NHC(=O)(R$^{\#}$) or —N(alkyl)C(=O)(R$^{\#}$), wherein each alkyl and R$^{\#}$ are independently as defined above.

An "O(alkyl)aminocarbonyl" group is a radical of the formula: —O(alkyl)C(=O)N(R$^{\#}$)$_2$, —O(alkyl)C(=O)NH(R$^{\#}$) or —O(alkyl)C(=O)NH$_2$, wherein each R$^{\#}$ is independently as defined above.

An "N-oxide" group is a radical of the formula: —N$^+$—O$^-$.

A "carboxy" group is a radical of the formula: —C(=O)OH.

A "ketone" group is a radical of the formula: —C(=O)(R$^{\#}$), wherein R$^{\#}$ is as defined above.

An "aldehyde" group is a radical of the formula: —CH(=O).

An "ester" group is a radical of the formula: —C(=O)O(R$^{\#}$) or —OC(=O)(R$^{\#}$), wherein R$^{\#}$ is as defined above.

A "urea" group is a radical of the formula: —N(alkyl)C(=O)N(R$^{\#}$)$_2$, —N(alkyl)C(=O)NH(R$^{\#}$), —N(alkyl)C (=O)NH$_2$, —NHC(=O)N(R$^{\#}$)$_2$, —NHC(=O)NH(R$^{\#}$), or —NHC(=O)NH$_2^{\#}$, wherein each alkyl and R$^{\#}$ are independently as defined above.

An "imine" group is a radical of the formula: —N=C(R$^{\#}$)$_2$ or —C(R$^{\#}$)=N(R$^{\#}$), wherein each R$^{\#}$ is independently as defined above.

An "imide" group is a radical of the formula: —C(=O)N(R#)C(=O)(R#) or —N(C=O)(R$^{\#}$))$_2$, wherein each R$^{\#}$ is independently as defined above.

A "urethane" group is a radical of the formula: —OC(=O)N(R$^{\#}$)$_2$, —OC(=O)NH(R$^{\#}$), —N(R$^{\#}$)C(=O)O(R$^{\#}$), or —NHC(=O)O(R$^{\#}$), wherein each R$^{\#}$ is independently as defined above.

An "amidine" group is a radical of the formula: —C(=N(R$^{\#}$))N(R$^{\#}$)$_2$, —C(=N(R$^{\#}$))NH(R$^{\#}$), —C(=N(R$^{\#}$))NH$_2$, —C(=NH)N(R$^{\#}$)$_2$, —C(=NH)NH(R$^{\#}$), —C(=NH)NH$_2$, —N=C(R$^{\#}$)N(R$^{\#}$)$_2$, —N=C(R$^{\#}$)NH(R$^{\#}$), —N=C(R$^{\#}$)NH$_2$, —N(R$^{\#}$)C(R$^{\#}$)=N(R$^{\#}$), —NHC(R$^{\#}$)=N(R$^{\#}$), —N(R$^{\#}$)C(R$^{\#}$)=NH, or —NHC(R$^{\#}$)=NH, wherein each R$^{\#}$ is independently as defined above.

A "guanidine" group is a radical of the formula: —N(R$^{\#}$)C(=N(R$^{\#}$))N(R$^{\#}$)$_2$, —NHC(=N(R$^{\#}$))N(R$^{\#}$)$_2$, —N(R$^{\#}$)C(=NH)N(R$^{\#}$)$_2$, —N(R$^{\#}$)C(=N(R$^{\#}$))NH(R$^{\#}$), —N(R$^{\#}$)C(=N(R$^{\#}$))NH$_2$, —NHC(=N(R$^{\#}$))NH(R$^{\#}$), —NHC(=N(R$^{\#}$))NH$_2$, —NHC(=NH)NH(R$^{\#}$), —NHC(=NH)NH$_2$, —N=C(N(R$^{\#}$)$_2$)$_2$, —N=C(NH(R$^{\#}$))$_2$, or —N=C(NH$_2$)$_2$, wherein each R$^{\#}$ is independently as defined above.

A "enamine" group is a radical of the formula: —N(R$^{\#}$)C(R$^{\#}$)=C(R$^{\#}$)$_2$, —NHC(R$^{\#}$)=C(R$^{\#}$)$_2$, —C(N(R$^{\#}$)$_2$)=C(R$^{\#}$)$_2$, —C(NH(R$^{\#}$))=C(R$^{\#}$)$_2$, —C(NH$_2$)=C(R$^{\#}$)$_2$, —C(R$^{\#}$)=C(R$^{\#}$)(N(R$^{\#}$)$_2$), —C(R$^{\#}$)=C(R$^{\#}$)(NH(R$^{\#}$)) or —C(R$^{\#}$)=C(R$^{\#}$)(NH$_2$), wherein each R$^{\#}$ is independently as defined above.

An "oxime" group is a radical of the formula: —C(=NO(R$^{\#}$))(R$^{\#}$), —C(=NOH)(R$^{\#}$), —CH(=NO(R$^{\#}$)), or —CH(=NOH), wherein each R$^{\#}$ is independently as defined above.

A "hydrazide" group is a radical of the formula: —C(=O)N(R$^{\#}$)N(R$^{\#}$)$_2$, —C(=O)NHN(R$^{\#}$)$_2$, —C(=O)N(R$^{\#}$)NH(R$^{\#}$), —C(=O)N(R$^{\#}$)NH$_2$, —C(=O)NHNH(R$^{\#}$)$_2$, or —C(=O)NHNH$_2$, wherein each R$^{\#}$ is independently as defined above.

A "hydrazine" group is a radical of the formula: —N(R$^{\#}$)N(R$^{\#}$)$_2$, —NHN(R$^{\#}$)$_2$, —N(R$^{\#}$)NH(R$^{\#}$), —N(R$^{\#}$)NH$_2$, —NHNH(R$^{\#}$)$_2$, or —NHNH$_2$, wherein each R$^{\#}$ is independently as defined above.

A "hydrazone" group is a radical of the formula: —C(=N—N(R$^{\#}$)$_2$)(R$^{\#}$)$_2$, —C(=N—NH(R$^{\#}$))(R$^{\#}$)$_2$, —C(=N—NH$_2$)(R$^{\#}$)$_2$, —N(R$^{\#}$)(N=C(R$^{\#}$)$_2$), or —NH(N=C(R$^{\#}$)$_2$), wherein each R$^{\#}$ is independently as defined above.

An "azide" group is a radical of the formula: —N$_3$.

An "isocyanate" group is a radical of the formula: —N=C=O.

An "isothiocyanate" group is a radical of the formula: —N=C=S.

A "cyanate" group is a radical of the formula: —OCN.

A "thiocyanate" group is a radical of the formula: —SCN.

A "thioether" group is a radical of the formula; —S(R$^{\#}$), wherein R$^{\#}$ is as defined above.

A "thiocarbonyl" group is a radical of the formula: —C(=S)(R$^{\#}$), wherein R$^{\#}$ is as defined above.

A "sulfinyl" group is a radical of the formula: —S(=O)(R$^{\#}$), wherein R$^{\#}$ is as defined above.

A "sulfone" group is a radical of the formula: —S(=O)$_2$(R$^{\#}$), wherein R$^{\#}$ is as defined above.

A "sulfonylamino" group is a radical of the formula: —NHSO$_2$(R$^{\#}$) or —N(alkyl)SO$_2$(R$^{\#}$), wherein each alkyl and R$^{\#}$ are defined above.

A "sulfonamide" group is a radical of the formula: —S(=O)$_2$N(R$^{\#}$)$_2$, or —S(=O)$_2$NH(R$^{\#}$), or —S(=O)$_2$NH$_2$, wherein each R$^{\#}$ is independently as defined above.

A "phosphonate" group is a radical of the formula: —P(=O)(O(R$^{\#}$))$_2$, —P(=O)(OH)$_2$, —OP(=O)(O(R$^{\#}$))(R$^{\#}$), or —OP(=O)(OH)(R$^{\#}$), wherein each R$^{\#}$ is independently as defined above.

A "phosphine" group is a radical of the formula: —P(R$^{\#}$)$_2$, wherein each R$^{\#}$ is independently as defined above.

When the groups described herein, with the exception of alkyl group are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonate; phosphine; thiocarbonyl; sulfinyl; sulfone; sulfonamide; ketone; aldehyde; ester; urea; urethane; oxime; hydroxylamine; alkoxyamine; aralkoxyamine; N-oxide; hydrazine; hydrazide; hydrazone; azide; isocyanate; isothiocyanate; cyanate; thiocyanate; oxygen (=O); B(OH)$_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl) aryloxy; aralkyloxy; heterocyclyloxy; and heterocyclyl alkoxy.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic or besylate, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences*, 18$^{th}$ eds., Mack Publishing, Easton Pa. (1990) or *Remington: The Science and Practice of Pharmacy*, 19$^{th}$ eds., Mack Publishing, Easton Pa. (1995).

As used herein and unless otherwise indicated, the term "clathrate" means a TOR kinase inhibitor, or a salt thereof, in the form of a crystal lattice that contains spaces (e.g., channels) that have a guest molecule (e.g., a solvent or water) trapped within or a crystal lattice wherein a TOR kinase inhibitor is a guest molecule.

As used herein and unless otherwise indicated, the term "solvate" means a TOR kinase inhibitor, or a salt thereof, that further includes a stoichiometric or non-stoichiometric amount of a solvent bound by non-covalent intermolecular forces. In one embodiment, the solvate is a hydrate.

As used herein and unless otherwise indicated, the term "hydrate" means a TOR kinase inhibitor, or a salt thereof, that further includes a stoichiometric or non-stoichiometric amount of water bound by non-covalent intermolecular forces.

As used herein and unless otherwise indicated, the term "prodrug" means a TOR kinase inhibitor derivative that can hydrolyze, oxidize, or otherwise react under biological conditions (in vitro or in vivo) to provide an active compound, particularly a TOR kinase inhibitor. Examples of prodrugs include, but are not limited to, derivatives and metabolites of a TOR kinase inhibitor that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6*th* ed. (Donald J. Abraham ed., 2001, Wiley) and *Design and Application of Prodrugs* (H. Bundgaard ed., 1985, Harwood Academic Publishers Gmfh).

As used herein and unless otherwise indicated, the term "stereoisomer" or "stereomerically pure" means one stereoisomer of a TOR kinase inhibitor that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The TOR kinase inhibitors can have chiral centers and can occur as racemates, individual enantiomers or diastereomers, and mixtures thereof. All such isomeric forms are included within the embodiments disclosed herein, including mixtures thereof. The use of stereomerically pure forms of such TOR kinase inhibitors, as well as the use of mixtures of those forms are encompassed by the embodiments disclosed herein. For example, mixtures comprising equal or unequal amounts of the enantiomers of a particular TOR kinase inhibitor may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the TOR kinase inhibitors can include E and Z isomers, or a mixture thereof, and cis and trans isomers or a mixture thereof. In certain embodiments, the TOR kinase inhibitors are isolated as either the cis or trans isomer. In other embodiments, the TOR kinase inhibitors are a mixture of the cis and trans isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

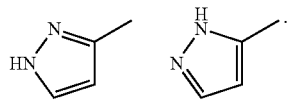

As readily understood by one skilled in the art, a wide variety of functional groups and other structures may exhibit tautomerism and all tautomers of the TOR kinase inhibitors are within the scope of the present invention.

It should also be noted the TOR kinase inhibitors can contain unnatural proportions of atomic isotopes at one or more of the atoms. For example, the compounds may be radiolabeled with radioactive isotopes, such as for example tritium ($^3$H), iodine-125 ($^{125}$I), sulfur-35 ($^{35}$S), or carbon-14 ($^{14}$C), or may be isotopically enriched, such as with deuterium ($^2$H), carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the TOR kinase inhibitors as described herein, whether radioactive or not, are intended to be encompassed within the scope of the embodiments provided herein. In some embodiments, there are provided isotopologues of the TOR kinase inhibitors, for example, the isotopologues are deuterium, carbon-13, or nitrogen-15 enriched TOR kinase inhibitors.

It should be noted that if there is a discrepancy between a depicted structure and a name for that structure, the depicted structure is to be accorded more weight.

"Treating" as used herein, means an alleviation, in whole or in part, of a cancer or a symptom associated with a cancer, or slowing, or halting of further progression or worsening of those symptoms.

"Preventing" as used herein, means the prevention of the onset, recurrence or spread, in whole or in part, of a cancer, or a symptom thereof.

The term "effective amount" in connection with an TOR kinase inhibitor or Compound AA means an amount alone or in combination capable of alleviating, in whole or in part, a symptom associated with a cancer, or slowing or halting further progression or worsening of those symptoms, or treating or preventing a cancer in a subject having or at risk for having a cancer. The effective amount of the TOR kinase inhibitor or Compound AA, for example in a pharmaceutical composition, may be at a level that will exercise the desired effect; for example, about 0.005 mg/kg of a subject's body weight to about 100 mg/kg of a patient's body weight in unit dosage for both oral and parenteral administration.

The term "cancer" includes, but is not limited to, blood born tumors and solid tumors. Blood born tumors include lymphomas, leukemias and myelomas. Lymphomas and leukemias are malignancies arising among white blood cells. The term "cancer" also refers to any of various malignant neoplasms characterized by the proliferation of cells that can invade surrounding tissue and metastasize to new body sites. Both benign and malignant tumors are classified according to the type of tissue in which they are found. For example, fibromas are neoplasms of fibrous connective tissue, and melanomas are abnormal growths of pigment (melanin) cells. Malignant tumors originating from epithelial tissue, e.g., in skin, bronchi, and stomach, are termed carcinomas. Malignancies of epithelial glandular tissue such as are found in the breast, prostate, and colon, are known as adenocarcinomas. Malignant growths of connective tissue, e.g., muscle, cartilage, lymph tissue, and bone, are called sarcomas. Through the process of metastasis, tumor cell migration to other areas of the body establishes neoplasms in areas away from the site of initial appearance. Bone tissues are one of the most favored sites of metastases of malignant tumors, occurring in about 30% of all cancer cases. Among malignant tumors, cancers of the lung, breast, prostate or the like are particularly known to be likely to metastasize to bone.

In the context of neoplasm, cancer, tumor growth or tumor cell growth, inhibition may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention. In this context, the term "prevention" includes either preventing the onset of clinically evident neoplasia altogether or preventing the onset of a preclinically evident stage of neoplasia in individuals at risk. Also intended to be encompassed by this definition is the prevention of transformation into malignant cells or to arrest or reverse the progression of premalignant cells to malignant cells. This includes prophylactic treatment of those at risk of developing the neoplasia.

The term "refractory B-cell non-Hodgkin's lymphoma" as used herein is defined as B-cell non-Hodgkin's lymphoma which was treated with an anti-CD-20 antibody-containing regimen, for example rituximab-containing regimen, (i) without achieving at least a partial response to therapy or (ii) which progressed within 6 months of treatment.

The term "relapsed B-cell non-Hodgkin's lymphoma" as used herein is defined as B-cell non-Hodgkin's lymphoma which progressed after ≥6 months post-treatment with an anti-CD-20 antibody-containing regimen, for example rituximab-containing regimen, after achieving partial response or complete response to therapy.

A person of ordinary skill will appreciate that diseases characterized as "B-cell lymphoma" exist as a continuum of diseases or disorders. While the continuum of B-cell lymphomas is sometimes discussed in terms of "aggressive" B-cell lymphomas or "indolent" B-cell lymphomas, a person of ordinary skill will appreciate that a B-cell lymphoma characterized as indolent may progress and become an aggressive B-cell lymphoma. Conversely, an aggressive form of B-cell lymphoma may be downgraded to an indolent or stable form of B-cell lymphoma. Reference is made to indolent and aggressive B-cell lymphomas as generally understood by a person skilled in the art with the recognition that such characterizations are inherently dynamic and depend on the particular circumstances of the individual.

As used herein, and unless otherwise specified, the term "in combination with" includes the administration of two or more therapeutic agents simultaneously, concurrently, or sequentially within no specific time limits unless otherwise indicated. In one embodiment, a TOR kinase inhibitor is administered in combination with Compound AA. In one embodiment, a TOR kinase inhibitor is administered in combination with Compound AA and further in combination with an anti-CD20 antibody, for example, rituximab (Rituxan®, Biogen Idec/Genentech or MabThera®, Hoffmann-La Roche). In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), essentially concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent, or any combination thereof. For example, in one embodiment, the first agent can be administered prior to the second therapeutic agent, for e.g. 1 week. In another, the first agent can be administered prior to (for example 1 day prior) and then concomitant with the second therapeutic agent.

The terms "patient" and "subject" as used herein include an animal, including, but not limited to, an animal such as a cow, monkey, horse, sheep, pig, chicken, turkey, quail, cat, dog, mouse, rat, rabbit or guinea pig, in one embodiment a mammal, in another embodiment a human. In one embodiment, a "patient" or "subject" is a human having a cancer.

In the context of a cancer, inhibition may be assessed by inhibition of disease progression, inhibition of tumor growth, reduction of primary tumor, relief of tumor-related symptoms, inhibition of tumor secreted factors (including tumor secreted hormones, such as those that contribute to carcinoid syndrome), delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from randomization until death from any cause, and is measured in the intent-to-treat population. TTP as used herein means the time from randomization until objective tumor progression; TTP does not include deaths. As used herein, PFS means the time from randomization until objective tumor progression or death. In one embodiment, PFS rates will be computed using the Kaplan-Meier estimates. In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

In certain embodiments, the treatment of lymphoma may be assessed by the International Workshop Criteria (IWC) for non-Hodgkin lymphoma (NHL) (see Cheson B D, Pfistner B, Juweid, M E, et. al. Revised Response Criteria for Malignant Lymphoma. J. Clin. Oncol: 2007: (25) 579-586), using the response and endpoint definitions shown below:

| Response | Definition | Nodal Masses | Spleen, liver | Bone Marrow |
| --- | --- | --- | --- | --- |
| CR | Disappearance of all evidence of disease | (a) FDG-avid or PET positive prior to therapy; mass of any size permitted if PET negative (b) Variably FDG-avid or PET negative; regression to normal size on CT | Not palpable, nodules disappeared | Infiltrate cleared on repeat biopsy; if indeterminate by morphology, immunohistochemistry should be negative |
| PR | Regression of measurable disease and no new sites | ≥50% decrease in SPD of up to 6 largest dominant masses; no increase in size of other nodes (a) FDG-avid or PET positive prior to therapy; one or more PET positive at previously involved site (b) Variably FDG-avid or PET negative; regression on CT | ≥50% decrease in SPD of nodules (for single nodule in greatest transverse diameter); no increase in size of liver or spleen | Irrelevant if positive prior to therapy; cell type should be specified |
| SD | Failure to attain CR/PR or PD | (a) FDG-avid or PET positive prior to therapy; PET positive at prior sites of disease and no new sites on CT or PET (b) Variably FDG-avid or PET negative; no change in size of previous lesions on CT | | |
| PD or relapsed disease | Any new lesion or increase by ≥50% of previously involved sites from nadir | Appearance of a new lesion(s) ≥1.5 cm in any axis, ≥50% increase in SPD of more than one node, or ≥50% increase in longest diameter of a previously identifed node ≥1 cm in short axis Lesions PET positive if FDG-avid lymphoma or PET positive prior to therapy | ≥50% increase from nadir in the SPD of any previous lesions | New or recurrent involvement |

Abbreviations: CR, complete remission; FDG, [$^{18}$F]fluorodeoxyglucose; PET, positron emission tomography; CT, computed tomography; PR, partial remission; SPD, sum of the product of the diameters; SD, stable disease; PD, progressive disease.

| End point | Patients | Definition | Measured from |
| --- | --- | --- | --- |
| Primary | | | |
| Overall survival | All | Death as a result of any cause | Entry onto study |
| Progression-free survival | All | Disease progression or death as a result of any cause | Entry onto study |
| Secondary | | | |
| Event-free survival | All | Failure of treatment or death as result of any cause | Entry onto study |
| Time to progression | All | Time to progression or death as a result of lymphoma | Entry onto study |
| Disease-free survival | In CR | Time to relapse or death as a result of lymphoma or acute toxicity of treatment | Documentation of response |
| Response duration | In CR or PR | Time to relapse or progression | Documentation of response |
| Lymphoma-specific survival | All | Time to death as a result of lymphoma | Entry onto study |
| Time to next treatment | All | Time to new treatment | End of primary treatment |

Abbreviations:
CR: complete remission;
PR: partial remission.

In one embodiment, the end point for lymphoma is evidence of clinical benefit. Clinical benefit may reflect improvement in quality of life, or reduction in patient symptoms, transfusion requirements, frequent infections, or other parameters. Time to reappearance or progression of lymphoma-related symptoms can also be used in this end point.

In certain embodiments, the treatment of CLL may be assessed by the International Workshop Guidelines for CLL (see Hallek M, Cheson B D, Catovsky D, et al. Guidelines for the diagnosis and treatment of chronic lymphocytic leukemia: a report from the International Workshop on Chronic Lymphocytic Leukemia updating the National Cancer Institute-Working Group 1996 guidelines. Blood, 2008; (111) 12: 5446-5456) using the response and endpoint definitions shown therein and in particular:

| Parameter | CR | PR | PD |
|---|---|---|---|
| Group A | | | |
| Lymphadenopathy[†] | None > 1.5 cm | Decrease ≥ 50% | Increase ≥ 50% |
| Hepatomegaly | None | Decrease ≥ 50% | Increase ≥ 50% |
| Splenomegaly | None | Decrease ≥ 50% | Increase ≥ 50% |
| Blood lymphocytes | <4000/μL | Decrease ≥ 50% from baseline | Increase ≥ 50% over baseline |
| Marrow[‡] | Normocellular, <30% lymphocytes, no B-lymphoid nodules. Hypocellular marrow defines CRi (5.1.6). | 50% reduction in marrow infiltrate, or B-lymphoid nodules | |
| Group B | | | |
| Platelet count | >100 000/μL | >100 000/μL or increase ≥ 50% over baseline | Decrease of ≥50% from baseline secondary to CLL |
| Hemoglobin | >11.0 g/dL | >11 g/dL or increase ≥50% over baseline | Decrease of > 2 g/dL from baseline secondary to CLL |
| Neutrophils[‡] | >1500/μL | >1500/μL or >50% improvement over baseline | |

Group A criteria define the tumor load;
Group B criteria define the function of the hematopoietic system (or marrow).
CR (complete remission): all of the criteria have to be met, and patients have to lack disease-related constitutional symptoms;
PR (partial remission): at least two of the criteria of group A plus one of the criteria of group B have to be met;
SD is absence of progressive disease (PD) and failure to achieve at least a PR;
PD: at least one of the above criteria of group A or group B has to be met.
Sum of the products of multiple lymph nodes (as evaluated by CT scans in clinical trials, or by physical examination in general practice). These parameters are irrelevant for some response categories.

In certain embodiments, the treatment of multiple myeloma may be assessed by the International Uniform Response Criteria for Multiple Myeloma (IURC) (see Durie B G M, Harousseau J-L, Miguel J S, et al. International uniform response criteria for multiple myeloma. Leukemia, 2006; (10) 10:1-7), using the response and endpoint definitions shown below:

| Response Subcategory | Response Criteria[a] |
|---|---|
| sCR | CR as defined below plus Normal FLC ratio and Absence of clonal cells in bone marrow[b] by immunohistochemistry or immunofluorescence[c] |
| CR | Negative immunofixation on the serum and urine and Disappearance of any soft tissue plasmacytomas and < 5% plasma cells in bone marrow[b] |
| VGPR | Serum and urine M-protein detectable by immunofixation but not on electrophoresis or 90% or greater reduction in serum M-protein plus urine M-protein level < 100 mg per 24 h |
| PR | ≥50% reduction of serum M-protein and reduction in 24-h urinary M-protein by ≥ 90% or to < 200 mg per 24 h If the serum and urine M-protein are unmeasurable,[d] a ≥50% decrease in the difference between involved and uninvolved FLC levels is required in place of the M-protein criteria |

-continued

| Response Subcategory | Response Criteria[a] |
|---|---|
| | If serum and urine M-protein are unmeasurable, and serum free light assay is also unmeasurable, ≥50% reduction in plasma cells is required in place of M-protein, provided baseline bone marrow plasma cell percentage was ≥ 30% |
| | In addition to the above listed criteria, if present at baseline, a ≥ 50% reduction in the size of soft tissue plasmacytomas is also required |
| SD (not recommended for use as an indicator of response; stability of disease is best described by providing the time to progression estimates) | Not meeting criteria for CR, VGPR, PR or progressive disease |

Abbreviations:
CR, complete response;
FLC, free light chain;
PR, partial response;
SD, stable disease;
sCR, stringent complete response;
VGPR, very good partial response;

[a]All response categories require two consecutive assessments made at anytime before the institution of any new therapy; all categories also require no known evidence of progressive or new bone lesions if radiographic studies were performed. Radiographic studies are not required to satisfy these response requirements;
[b]Confirmation with repeat bone marrow biopsy not needed;
[c]Presence/absence of clonal cells is based upon the κ/λ ratio. An abnormal κ/λ ratio by immunohistochemistry and/or immunofluorescence requires a minimum of 100 plasma cells for analysis. An abnormal ratio reflecting presence of an abnormal clone is κ/λ of > 4:1 or < 1:2.
[d]Measurable disease defined by at least one of the following measurements: Bone marrow plasma cells ≥ 30%; Serum M-protein ≥ 1 g/dl (≥10 gm/l)[10 g/l]; Urine M-protein ≥ 200 mg/24 h; Serum FLC assay: Involved FLC level ≥ 10 mg/dl (≥100 mg/l); provided serum FLC ratio is abnormal.

In certain embodiments, the treatment of a cancer may be assessed by Response Evaluation Criteria in Solid Tumors (RECIST 1.1) (see Thereasse P., et al. New Guidelines to Evaluate the Response to Treatment in Solid Tumors. J. of the National Cancer Institute; 2000; (92) 205-216 and Eisenhauer E. A., Therasse P., Bogaerts J., et al. New response evaluation criteria in solid tumours: Revised RECIST guideline (version 1.1). European J. Cancer; 2009; (45) 228-247). Overall responses for all possible combinations of tumor responses in target and non-target lesions with our without the appearance of new lesions are as follows:

| Target lesions | Non-target lesions | New lesions | Overall response |
|---|---|---|---|
| CR | CR | No | CR |
| CR | Incomplete response/SD | No | PR |
| PR | Non-PD | No | PR |
| SD | Non-PD | No | SD |
| PD | Any | Yes or no | PD |
| Any | PD | Yes or no | PD |
| Any | Any | Yes | PD |

CR = complete response;
PR = partial response;
SD = stable disease; and
PD = progressive disease.

With respect to the evaluation of target lesions, complete response (CR) is the disappearance of all target lesions, partial response (PR) is at least a 30% decrease in the sum of the longest diameter of target lesions, taking as reference the baseline sum longest diameter, progressive disease (PD) is at least a 20% increase in the sum of the longest diameter of target lesions, taking as reference the smallest sum longest diameter recorded since the treatment started or the appearance of one or more new lesions and stable disease (SD) is neither sufficient shrinkage to qualify for partial response nor sufficient increase to qualify for progressive disease, taking as reference the smallest sum longest diameter since the treatment started.

With respect to the evaluation of non-target lesions, complete response (CR) is the disappearance of all non-target lesions and normalization of tumor marker level; incomplete response/stable disease (SD) is the persistence of one or more non-target lesion(s) and/or the maintenance of tumor marker level above the normal limits, and progressive disease (PD) is the appearance of one or more new lesions and/or unequivocal progression of existing non-target lesions.

The procedures, conventions, and definitions described below provide guidance for implementing the recommendations from the Response Assessment for Neuro-Oncology (RANO) Working Group regarding response criteria for high-grade gliomas (Wen P., Macdonald, D R., Reardon, D A., et al. Updated response assessment criteria for highgrade gliomas: Response assessment in neuro-oncology working group. J Clin Oncol 2010; 28: 1963-1972). Primary modifications to the RANO criteria for Criteria for Time Point Responses (TPR) can include the addition of operational conventions for defining changes in glucocorticoid dose, and the removal of subjects' clinical deterioration component to focus on objective radiologic assessments. The baseline MRI scan is defined as the assessment performed at the end of the post-surgery rest period, prior to re-initiating compound treatment. The baseline MRI is used as the reference for assessing complete response (CR) and partial response (PR). Whereas, the smallest SPD (sum of the products of perpendicular diameters) obtained either at baseline or at subsequent assessments will be designated the nadir assessment and utilized as the reference for determining progression. For the 5 days preceding any protocol-defined MRI scan, subjects receive either no glucocorticoids or are on a stable dose of glucocorticoids. A stable dose is defined as the same daily dose for the 5 consecutive days preceding the MRI scan. If the prescribed glucocorticoid dose is changed in the 5 days before the baseline scan, a new baseline scan is required with glucocorticoid use meeting the criteria described above. The following definitions will be used.

Measurable Lesions: Measurable lesions are contrast-enhancing lesions that can be measured bidimensionally. A measurement is made of the maximal enhancing tumor diameter (also known as the longest diameter, LD). The greatest perpendicular diameter is measured on the same image. The cross hairs of bidimensional measurements should cross and the product of these diameters will be calculated.

Minimal Diameter: T1-weighted image in which the sections are 5 mm with 1 mm skip. The minimal LD of a measurable lesion is set as 5 mm by 5 mm. Larger diameters may be required for inclusion and/or designation as target lesions. After baseline, target lesions that become smaller than the minimum requirement for measurement or become no longer amenable to bidimensional measurement will be recorded at the default value of 5 mm for each diameter below 5 mm. Lesions that disappear will be recorded as 0 mm by 0 mm.

Multicentric Lesions: Lesions that are considered multicentric (as opposed to continuous) are lesions where there is normal intervening brain tissue between the two (or more) lesions. For multicentric lesions that are discrete foci of enhancement, the approach is to separately measure each enhancing lesion that meets the inclusion criteria. If there is no normal brain tissue between two (or more) lesions, they will be considered the same lesion.

Nonmeasurable Lesions: All lesions that do not meet the criteria for measurable disease as defined above will be considered non-measurable lesions, as well as all nonenhancing and other truly nonmeasurable lesions. Nonmeasurable lesions include foci of enhancement that are less than the specified smallest diameter (ie., less than 5 mm by 5 mm), nonenhancing lesions (eg., as seen on T1-weighted post-contrast, T2-weighted, or fluid-attenuated inversion recovery (FLAIR) images), hemorrhagic or predominantly cystic or necrotic lesions, and leptomeningeal tumor. Hemorrhagic lesions often have intrinsic T1-weighted hyperintensity that could be misinterpreted as enhancing tumor, and for this reason, the pre-contrast T1-weighted image may be examined to exclude baseline or interval sub-acute hemorrhage.

At baseline, lesions will be classified as follows: Target lesions: Up to 5 measurable lesions can be selected as target lesions with each measuring at least 10 mm by 5 mm, representative of the subject's disease; Non-target lesions: All other lesions, including all nonmeasurable lesions (including mass effects and T2/FLAIR findings) and any measurable lesion not selected as a target lesion. At baseline, target lesions are to be measured as described in the definition for measurable lesions and the SPD of all target lesions is to be determined. The presence of all other lesions is to be documented. At all post-treatment evaluations, the baseline classification of lesions as target and non-target lesions will be maintained and lesions will be documented and described in a consistent fashion over time (eg., recorded in the same order on source documents and eCRFs). All measurable and non-measurable lesions must be assessed using the same technique as at baseline (e.g., subjects should be imaged on the same MRI scanner or at least with the same magnet strength) for the duration of the study to reduce difficulties in interpreting changes. At each evaluation, target lesions will be measured and the SPD calculated. Non-target lesions will be assessed qualitatively and new lesions, if any, will be documented separately. At each evaluation, a time point response will be determined for target lesions, non-target lesions, and new lesion. Tumor progression can be established even if only a subset of lesions is assessed. However, unless progression is observed, objective status (stable disease, PR or CR) can only be determined when all lesions are assessed.

Confirmation assessments for overall time point responses of CR and PR will be performed at the next scheduled assessment, but confirmation may not occur if scans have an interval of <28 days. Best response, incorporating confirmation requirements, will be derived from the series of time points.

In certain embodiments, treatment of a cancer may be assessed by the inhibition of phosphorylation of S6RP, 4E-BP1, AKT and/or DNA-PK in circulating blood and/or tumor cells, and/or skin biopsies or tumor biopsies/aspirates, before, during and/or after treatment with a TOR kinase inhibitor. For example, the inhibition of phosphorylation of S6RP, 4E-BP1, AKT and/or DNA-PK is assessed in B-cells, T-cells and/or monocytes. In other embodiments, treatment of a cancer may be assessed by the inhibition of DNA-dependent protein kinase (DNA-PK) activity in skin samples and/or tumor biopsies/aspirates, such as by assessment of the amount of pDNA-PK S2056 as a biomarker for DNA damage pathways, before, during, and/or after TOR kinase inhibitor treatment. In one embodiment, the skin sample is irradiated by UV light.

In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

As used herein, the term "antibody", or grammatical variations thereof (i.e., antibodies), refers to polypeptide(s) capable of binding to an epitope. In some embodiments, an antibody is a full-length antibody. In some embodiments, an antibody is less than full length (i.e., an antibody fragment) but includes at least one binding site. In some such embodiments, the binding site comprises at least one, and preferably at least two sequences with structure of antibody variable regions. In some embodiments, the term "antibody" encompasses any protein having a binding domain which is homologous or largely homologous to an immunoglobulin-binding domain. In particular embodiments, the term "antibody" encompasses polypeptides having a binding domain that shows at least 99% identity with an immunoglobulin-binding domain. In some embodiments, the antibody is any protein having a binding domain that shows at least 70%, at least 80%, at least 85%, at least 90% or at least 95% identity with an immunoglobulin-binding domain. Antibody polypeptides in accordance with the present invention may be prepared by any available means, including, for example, isolation from a natural source or antibody library, recombinant production in or with a host system, chemical synthesis, etc., or combinations thereof. In some embodiments, an antibody is monoclonal or polyclonal. In some embodiments, an antibody may be a member of any immunoglobulin class, including any of the human classes IgG, IgM, IgA, IgD and IgE. In certain embodiments, an antibody is a member of the IgG immunoglobulin class. In some embodiments, the term "antibody" refers to any derivative of an antibody that possesses the ability to bind to an epitope of interest. In some embodiments, an antibody fragment comprises multiple chains that are linked together, for example, by disulfide linkages. In some embodiments, an antibody is a human antibody. In some embodiments, an antibody is a humanized antibody. In some embodiments, humanized antibodies include chimeric immunoglobulins, immunoglobulin chains or antibody fragments (Fv, Fab, Fab', F(ab')$_2$ or other antigen binding subsequences of antibodies) that contain minimal sequence derived from non-human immunoglobulin. In some embodiments, humanized antibodies are human immunoglobulin (recipient antibody) in which residues from a complementary-determining region (CDR) of the recipient are replaced by residues from a CDR of a non-human species (donor antibody) such as mouse, rat or rabbit having the desired specificity, affinity and capacity. In particular embodiments, antibodies for use in the present invention bind to particular epitopes of CD20. In some embodiments, epitopes of CD20 to which anti-CD20 antibodies bind include, for example, 170ANPS173 (Binder et al., *Blood* 2006, 108(6): 1975-1978), FMC7 (Deans et al., *Blood* 2008, 111(4): 2492), Rp5-L and Rp15-C (mimotopes of CD20) (Perosa et al., *J. Immunol.* 2009, 182:416-423), 182YCYSI185 (Binder et al., *Blood* 2006, 108(6): 1975-1978) and WEWTI (a mimic of 182YCYSI185) (Binder et al., *Blood* 2006, 108(6): 1975-1978). In some embodiments, an anti-CD20 antibody has a binding affinity (Kd) for an epitope of CD20 of less than 12 nM, less than 11 nM, less than 10 nM, less than 9 nM, less than 8 nM, less than 7 nM, less than 6 nM, less than 5 nM, less than 4 nM, less than 3 nM, less than 2 nM or less than 1 nM.

As used herein, the term "biosimilar" (for example, of an approved reference product/biological drug, such as a protein therapeutic, antibody, etc.) refers to a biologic product that is similar to the reference product based upon data derived from (a) analytical studies that demonstrate that the biological product is highly similar to the reference product notwithstanding minor differences in clinically inactive components; (b) animal studies (including the assessment of toxicity); and/or (c) a clinical study or studies (including the assessment of immunogenicity and pharmacokinetics or pharmacodynamics) that are sufficient to demonstrate safety, purity, and potency in one or more appropriate conditions of use for which the reference product is approved and intended to be used and for which approval is sought (e.g., that there are no clinically meaningful differences between the biological product and the reference product in terms of the safety, purity, and potency of the product).

In some embodiments, the biosimilar biological product and reference product utilizes the same mechanism or mechanisms of action for the condition or conditions of use prescribed, recommended, or suggested in the proposed labeling, but only to the extent the mechanism or mechanisms of action are known for the reference product. In some embodiments, the condition or conditions of use prescribed, recommended, or suggested in the labeling proposed for the biological product have been previously approved for the reference product. In some embodiments, the route of administration, the dosage form, and/or the strength of the biological product are the same as those of the reference product. In some embodiments, the facility in which the biological product is manufactured, processed, packed, or held meets standards designed to assure that the biological product continues to be safe, pure, and potent. The reference product may be approved in at least one of the U.S., Europe, or Japan. A biosimilar can be for example, a presently known antibody having the same primary amino acid sequence as a marketed antibody, but may be made in different cell types or by different production, purification or formulation methods.

5.2 TOR Kinase Inhibitors

The compounds provided herein are generally referred to as "TOR kinase inhibitor(s)." In one aspect, the TOR kinase inhibitors do not include rapamycin or rapamycin analogs (rapalogs).

In one embodiment, the TOR kinase inhibitors include compounds having the following formula (I):

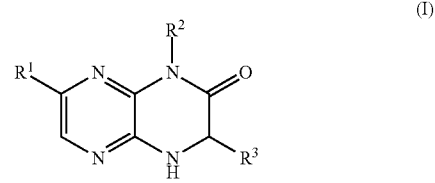

and pharmaceutically acceptable salts, clathrates, solvates, stereoisomers, tautomers, metabolites, isotopologues and prodrugs thereof, wherein:

$R^1$ is substituted or unsubstituted $C_{1-8}$ alkyl, substituted or unsubstituted aryl, substituted or unsubstituted cycloalkyl, substituted or unsubstituted heterocyclyl, or substituted or unsubstituted heterocyclylalkyl;

$R^2$ is H, substituted or unsubstituted $C_{1-8}$ alkyl, substituted or unsubstituted cycloalkyl, substituted or unsubstituted heterocyclyl, substituted or unsubstituted heterocyclylalkyl, substituted or unsubstituted aralkyl, or substituted or unsubstituted cycloalkylalkyl;

$R^3$ is H, or a substituted or unsubstituted $C_{1-8}$ alkyl, wherein in certain embodiments, the TOR kinase inhibitors do not include 7-(4-hydroxyphenyl)-1-(3-methoxybenzyl)-3,4-dihydropyrazino[2,3-b]pyrazin-2(1H)-one, depicted below:

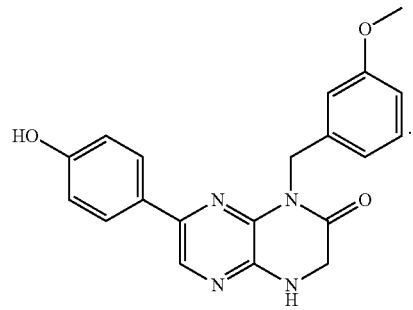 [SMILES: COc1cccc(CN2C(=O)CNc3ncc(-c4ccc(O)cc4)nc32)c1]

In some embodiments of compounds of formula (I), $R^1$ is substituted or unsubstituted aryl or substituted or unsubstituted heteroaryl. For example, $R^1$ is phenyl, pyridyl, pyrimidyl, benzimidazolyl, 1H-pyrrolo[2,3-b]pyridyl, indazolyl, indolyl, 1H-imidazo[4,5-b]pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl (for example, methyl), substituted or unsubstituted heterocyclyl (for example, a substituted or unsubstituted triazolyl or pyrazolyl), aminocarbonyl, halogen (for example, fluorine), cyano, hydroxyalkyl and hydroxy. In other embodiments, $R^1$ is pyridyl substituted with one or more substituents independently selected from the group consisting of substituted or unsubstituted $C_{1-8}$ alkyl (for example, methyl), substituted or unsubstituted heterocyclyl (for example, a substituted or unsubstituted triazolyl), halogen, aminocarbonyl, cyano, hydroxyalkyl (for example, hydroxypropyl), —OR, and —$NR_2$, wherein each R is independently H, or a substituted or unsubstituted $C_{1-4}$ alkyl. In some embodiments, $R^1$ is 1H-pyrrolo[2,3-b]pyridyl or benzimidazolyl, optionally substituted with one or more substituents independently selected from the group consisting of substituted or unsubstituted $C_{1-8}$ alkyl, and —$NR_2$, wherein R is independently H, or a substituted or unsubstituted $C_{1-4}$ alkyl.

In some embodiments, $R^1$ is

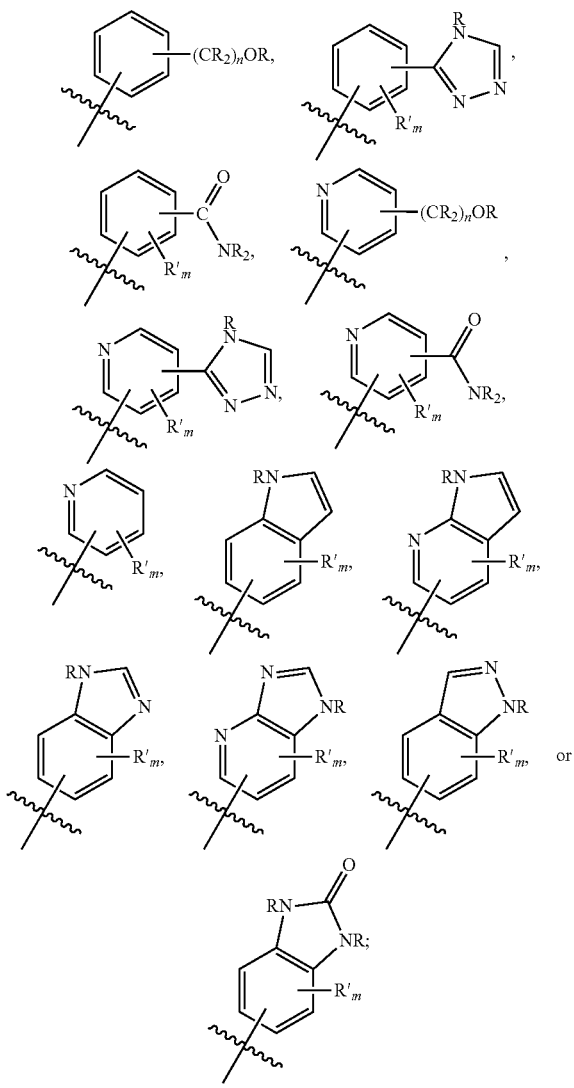

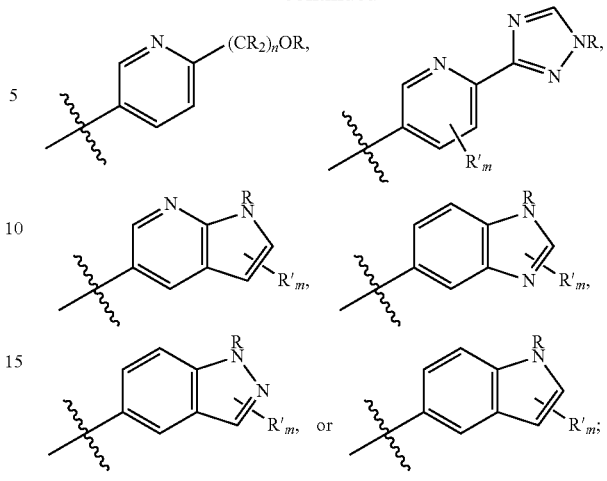

wherein R is at each occurrence independently H, or a substituted or unsubstituted $C_{1-4}$ alkyl; R' is at each occurrence independently a substituted or unsubstituted $C_{1-4}$ alkyl, halogen, cyano, —OR or —$NR_2$; m is 0-3; and n is 0-3.

In some embodiments of compounds of formula (I), $R^2$ is H, substituted or unsubstituted $C_{1-8}$ alkyl, substituted or unsubstituted cycloalkyl, substituted or unsubstituted heterocyclyl, substituted or unsubstituted $C_{1-4}$ alkyl-heterocyclyl, substituted or unsubstituted $C_{1-4}$ alkyl-aryl, or substituted or unsubstituted $C_{1-4}$ alkyl-cycloalkyl. For example, $R^2$ is H, methyl, ethyl, n-propyl, isopropyl, n-butyl, sec-butyl, isobutyl, tert-butyl, n-pentyl, isopentyl, cyclopentyl, cyclohexyl, tetrahydrofuranyl, tetrahydropyranyl, ($C_{1-4}$ alkyl)-phenyl, ($C_{1-4}$ alkyl)-cyclopropyl, ($C_{1-4}$ alkyl)-cyclobutyl, ($C_{1-4}$ alkyl)-cyclopentyl, ($C_{1-4}$ alkyl)-cyclohexyl, ($C_{1-4}$ alkyl)-pyrrolidyl, ($C_{1-4}$ alkyl)-piperidyl, ($C_{1-4}$ alkyl)-piperazinyl, ($C_{1-4}$ alkyl)-morpholinyl, ($C_{1-4}$ alkyl)-tetrahydrofuranyl, or ($C_{1-4}$ alkyl)-tetrahydropyranyl, each optionally substituted.

In other embodiments, $R^2$ is H, $C_{1-4}$ alkyl, ($C_{1-4}$alkyl)(OR),

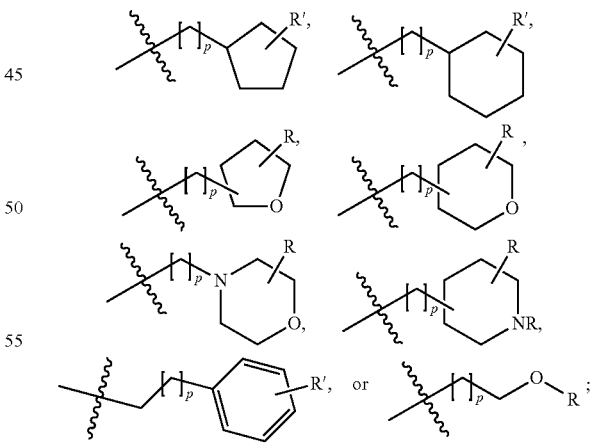

wherein R is at each occurrence independently H, or a substituted or unsubstituted $C_{1-4}$ alkyl (for example, methyl); R' is at each occurrence independently H, —OR, cyano, or a substituted or unsubstituted $C_{1-4}$ alkyl (for example, methyl); and p is 0-3.

In other embodiments of compounds of formula (I), $R^2$ is H, $C_{1-4}$ alkyl, ($C_{1-4}$alkyl)(OR), wherein R is at each occurrence independently H, or a substituted or unsubstituted $C_{1-4}$ alkyl (for example, methyl); R' is at each occurrence independently a substituted or unsubstituted $C_{1-4}$ alkyl (for example, methyl), halogen (for example, fluoro), cyano, —OR, or —$NR_2$; m is 0-3; and n is 0-3. It will be understood by those skilled in the art that any of the substitutents R' may be attached to any suitable atom of any of the rings in the fused ring systems.

In some embodiments of compounds of formula (I), $R^1$ is

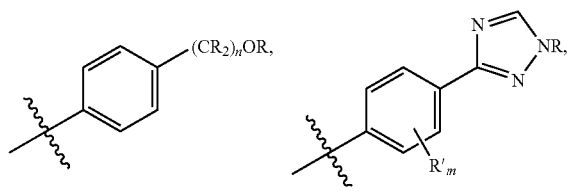

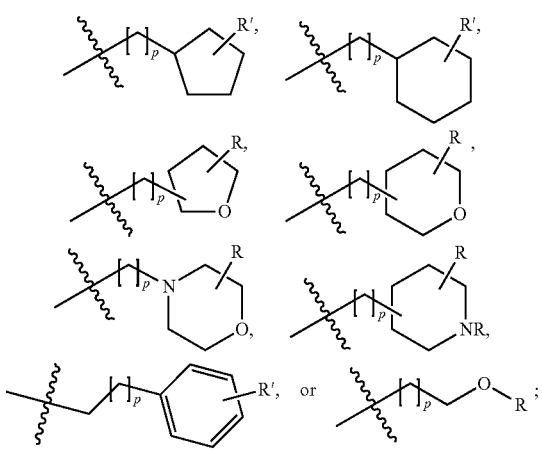

wherein R is at each occurrence independently H, or a substituted or unsubstituted $C_{1-2}$ alkyl; R' is at each occurrence independently H, —OR, cyano, or a substituted or unsubstituted $C_{1-2}$ alkyl; and p is 0-1.

In other embodiments of compounds of formula (I), $R^3$ is H.

In some such embodiments described herein, $R^1$ is substituted or unsubstituted aryl, or substituted or unsubstituted heteroaryl. For example, $R^1$ is phenyl, pyridyl, pyrimidyl, benzimidazolyl, 1H-pyrrolo[2,3-b]pyridyl, indazolyl, indolyl, 1H-imidazo[4,5-b]pyridine, pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl, substituted or unsubstituted heterocyclyl, aminocarbonyl, halogen, cyano, hydroxyalkyl and hydroxy. In others, $R^1$ is pyridyl substituted with one or more substituents independently selected from the group consisting of $C_{1-8}$ alkyl, substituted or unsubstituted heterocyclyl, halogen, aminocarbonyl, cyano, hydroxyalkyl, —OR, and —$NR_2$, wherein each R is independently H, or a substituted or unsubstituted $C_{1-4}$ alkyl. In still others, $R^1$ is 1H-pyrrolo[2,3-b]pyridyl or benzimidazolyl, optionally substituted with one or more substituents independently selected from the group consisting of substituted or unsubstituted $C_{1-8}$ alkyl, and —$NR_2$, wherein R is independently H, or a substituted or unsubstituted $C_{1-4}$ alkyl.

In certain embodiments, the compounds of formula (I) have an $R^1$ group set forth herein and an $R^2$ group set forth herein.

In some embodiments of compounds of formula (I), the compound inhibits TOR kinase. In other embodiments of compounds of formula (I), the compound inhibits DNA-PK. In certain embodiments of compounds of formula (I), the compound inhibits both TOR kinase and DNA-PK.

In some embodiments of compounds of formula (I), the compound at a concentration of 10 μM inhibits TOR kinase, DNA-PK, PI3K, or a combination thereof by at least about 50%. Compounds of formula (I) may be shown to be inhibitors of the kinases above in any suitable assay system.

Representative TOR kinase inhibitors of formula (I) include compounds from Table A.

TABLE A 7-(5-fluoro-2-methyl-4-(1H-1,2,4-triazol-3-yl)phenyl)-1-((trans-4-methoxycyclohexyl)methyl)-3,4-dihydropyrazino[2,3-b]pyrazin-2(1H)-one;
7-(6-(1H-1,2,4-triazol-3-yl)pyridin-3-yl)-1-(cis-4-methoxycyclohexyl)-3,4-dihydropyrazino[2,3-b]pyrazin-2(1H)-one;
7-(1H-pyrrolo[2,3-b]pyridin-3-yl)-1-(2-(tetrahydro-2H-pyran-4-yl)ethyl)-3,4-dihydropyrazino[2,3-b]pyrazin-2(1H)-one;
7-(5-fluoro-2-methyl-4-(1H-1,2,4-triazol-3-yl)phenyl)-1-((cis-4-methoxycyclohexyl)methyl)-3,4-dihydropyrazino[2,3-b]pyrazin-2(1H)-one;
1-ethyl-7-(1H-pyrrolo[3,2-b]pyridin-5-yl)-3,4-dihydropyrazino[2,3-b]pyrazin-2(1H)-one;
7-(6-(1H-1,2,4-triazol-3-yl)pyridin-3-yl)-1-((cis-4-methoxycyclohexyl)methyl)-3,4-dihydropyrazino[2,3-b]pyrazin-2(1H)-one;
7-(1H-benzo[d]imidazol-4-yl)-1-(2-(tetrahydro-2H-pyran-4-yl)ethyl)-3,4-dihydropyrazino[2,3-b]pyrazin-2(1H)-one;
7-(1H-pyrrolo[2,3-b]pyridin-4-yl)-1-(2-(tetrahydro-2H-pyran-4-yl)ethyl)-3,4-dihydropyrazino[2,3-b]pyrazin-2(1H)-one;
7-(6-(1H-1,2,4-triazol-3-yl)pyridin-3-yl)-1-((trans-4-methoxycyclohexyl)methyl)-3,4-dihydropyrazino[2,3-b]pyrazin-2(1H)-one;
7-(6-(1H-1,2,4-triazol-3-yl)pyridin-3-yl)-1-((trans-4-hydroxycyclohexyl)methyl)-3,4-dihydropyrazino[2,3-b]pyrazin-2(1H)-one;
7-(6-(1H-1,2,4-triazol-3-yl)pyridin-3-yl)-1-(cis-4-hydroxycyclohexyl)-3,4-dihydropyrazino[2,3-b]pyrazin-2(1H)-one;
7-(5-fluoro-2-methyl-4-(1H-1,2,4-triazol-3-yl)phenyl)-1-(cis-4-hydroxycyclohexyl)-3,4-dihydropyrazino[2,3-b]pyrazin-2(1H)-one;
7-(6-(1H-1,2,4-triazol-3-yl)pyridin-3-yl)-1-(tetrahydro-2H-pyran-4-yl)-3,4-dihydropyrazino[2,3-b]pyrazin-2(1H)-one;
7-(6-(1H-1,2,4-triazol-3-yl)pyridin-3-yl)-1-(2-methoxyethyl)-3,4-dihydropyrazino[2,3-b]pyrazin-2(1H)-one;
7-(6-(1H-1,2,4-triazol-3-yl)pyridin-3-yl)-1-ethyl-3,4-dihydropyrazino[2,3-b]pyrazin-2(1H)-one;
7-(5-fluoro-2-methyl-4-(1H-1,2,4-triazol-3-yl)phenyl)-1-((cis-4-hydroxycyclohexyl)methyl)-3,4-dihydropyrazino[2,3-b]pyrazin-2(1H)-one;
7-(5-fluoro-2-methyl-4-(1H-1,2,4-triazol-3-yl)phenyl)-1-(tetrahydro-2H-pyran-4-yl)-3,4-dihydropyrazino[2,3-b]pyrazin-2(1H)-one;
7-(1H-indol-4-yl)-1-(2-(tetrahydro-2H-pyran-4-yl)ethyl)-3,4-dihydropyrazino[2,3-b]pyrazin-2(1H)-one;
7-(5-fluoro-2-methyl-4-(1H-1,2,4-triazol-3-yl)phenyl)-1-((trans-4-hydroxycyclohexyl)methyl)-3,4-dihydropyrazino[2,3-b]pyrazin-2(1H)-one;
7-(6-(1H-1,2,4-triazol-3-yl)pyridin-3-yl)-1-((cis-4-hydroxycyclohexyl)methyl)-3,4-dihydropyrazino[2,3-b]pyrazin-2(1H)-one;
7-(6-(1H-1,2,4-triazol-3-yl)pyridin-3-yl)-1-(trans-4-hydroxycyclohexyl)-3,4-dihydropyrazino[2,3-b]pyrazin-2(1H)-one;

TABLE A-continued 7-(6-(1H-1,2,4-triazol-3-yl)pyridin-3-yl)-1-(trans-4-methoxycyclohexyl)-3,4-dihydropyrazino[2,3-b]pyrazin-2(1H)-one;

7-(6-(1H-1,2,4-triazol-3-yl)pyridin-3-yl)-1-isopropyl-3,4-dihydropyrazino[2,3-b]pyrazin-2(1H)-one;

7-(5-fluoro-2-methyl-4-(1H-1,2,4-triazol-3-yl)phenyl)-1-(trans-4-methoxycyclohexyl)-3,4-dihydropyrazino[2,3-b]pyrazin-2(1H)-one;

7-(5-fluoro-2-methyl-4-(1H-1,2,4-triazol-3-yl)phenyl)-1-(trans-4-hydroxycyclohexyl)-3,4-dihydropyrazino[2,3-b]pyrazin-2(1H)-one;

7-(5-fluoro-2-methyl-4-(1H-1,2,4-triazol-3-yl)phenyl)-1-(2-methoxyethyl)-3,4-dihydropyrazino[2,3-b]pyrazin-2(1H)-one;

7-(5-fluoro-2-methyl-4-(1H-1,2,4-triazol-3-yl)phenyl)-1-isopropyl-3,4-dihydropyrazino[2,3-b]pyrazin-2(1H)-one;

1-ethyl-7-(5-fluoro-2-methyl-4-(1H-1,2,4-triazol-3-yl)phenyl)-3,4-dihydropyrazino[2,3-b]pyrazin-2(1H)-one;

7-(2-hydroxypyridin-4-yl)-1-(2-(tetrahydro-2H-pyran-4-yl)ethyl)-3,4-dihydropyrazino[2,3-b]pyrazin-2(1H)-one;

1-isopropyl-7-(4-methyl-6-(1H-1,2,4-triazol-3-yl)pyridin-3-yl)-3,4-dihydropyrazino[2,3-b]pyrazin-2(1H)-one;

5-(8-isopropyl-7-oxo-5,6,7,8-tetrahydropyrazino[2,3-b]pyrazin-2-yl)-4-methylpicolinamide;

7-(1H-indazol-4-yl)-1-(2-(tetrahydro-2H-pyran-4-yl)ethyl)-3,4-dihydropyrazino[2,3-b]pyrazin-2(1H)-one;

7-(2-aminopyrimidin-5-yl)-1-(2-(tetrahydro-2H-pyran-4-yl)ethyl)-3,4-dihydropyrazino[2,3-b]pyrazin-2(1H)-one;

7-(2-aminopyridin-4-yl)-1-(2-(tetrahydro-2H-pyran-4-yl)ethyl)-3,4-dihydropyrazino[2,3-b]pyrazin-2(1H)-one;

7-(6-(methylamino)pyridin-3-yl)-1-(2-(tetrahydro-2H-pyran-4-yl)ethyl)-3,4-dihydropyrazino[2,3-b]pyrazin-2(1H)-one;

7-(6-hydroxypyridin-3-yl)-1-(2-(tetrahydro-2H-pyran-4-yl)ethyl)-3,4-dihydropyrazino[2,3-b]pyrazin-2(1H)-one;

7-(4-(1H-pyrazol-3-yl)phenyl)-1-(2-methoxyethyl)-3,4-dihydropyrazino[2,3-b]pyrazin-2(1H)-one;

7-(pyridin-3-yl)-1-(2-(tetrahydro-2H-pyran-4-yl)ethyl)-3,4-dihydropyrazino[2,3-b]pyrazin-2(1H)-one;

7-(1H-indazol-4-yl)-1-(2-methoxyethyl)-3,4-dihydropyrazino[2,3-b]pyrazin-2(1H)-one;

7-(1H-indazol-6-yl)-1-(2-methoxyethyl)-3,4-dihydropyrazino[2,3-b]pyrazin-2(1H)-one;

7-(pyrimidin-5-yl)-1-(2-(tetrahydro-2H-pyran-4-yl)ethyl)-3,4-dihydropyrazino[2,3-b]pyrazin-2(1H)-one;

7-(6-methoxypyridin-3-yl)-1-(2-(tetrahydro-2H-pyran-4-yl)ethyl)-3,4-dihydropyrazino[2,3-b]pyrazin-2(1H)-one;

1-(2-methoxyethyl)-7-(1H-pyrrolo[2,3-b]pyridin-5-yl)-3,4-dihydropyrazino[2,3-b]pyrazin-2(1H)-one;

1-ethyl-7-(1H-pyrrolo[2,3-b]pyridin-5-yl)-3,4-dihydropyrazino[2,3-b]pyrazin-2(1H)-one;

1-ethyl-7-(1H-indazol-4-yl)-3,4-dihydropyrazino[2,3-b]pyrazin-2(1H)-one;

7-(pyridin-4-yl)-1-(2-(tetrahydro-2H-pyran-4-yl)ethyl)-3,4-dihydropyrazino[2,3-b]pyrazin-2(1H)-one;

7-(6-aminopyridin-3-yl)-1-(2-(tetrahydro-2H-pyran-4-yl)ethyl)-3,4-dihydropyrazino[2,3-b]pyrazin-2(1H)-one;

1-methyl-7-(2-methyl-6-(4H-1,2,4-triazol-3-yl)pyridin-3-yl)-3,4-dihydropyrazino[2,3-b]pyrazin-2(1H)-one;

2-(2-hydroxypropan-2-yl)-5-(8-(trans-4-methoxycyclohexyl)-7-oxo-5,6,7,8-tetrahydropyrazino[2,3-b]pyrazin-2-yl)pyridine 1-oxide;

4-methyl-5-(7-oxo-8-((tetrahydro-2H-pyran-4-yl)methyl)-5,6,7,8-tetrahydropyrazino[2,3-b]pyrazin-2-yl)picolinamide;

5-(8-((cis-4-methoxycyclohexyl)methyl)-7-oxo-5,6,7,8-tetrahydropyrazino[2,3-b]pyrazin-2-yl)-4-methylpicolinamide;

7-(1H-pyrazol-4-yl)-1-(2-(tetrahydro-2H-pyran-4-yl)ethyl)-3,4-dihydropyrazino[2,3-b]pyrazin-2(1H)-one;

1-(trans-4-methoxycyclohexyl)-7-(4-methyl-6-(1H-1,2,4-triazol-3-yl)pyridin-3-yl)-3,4-dihydropyrazino[2,3-b]pyrazin-2(1H)-one;

3-((7-(2-methyl-6-(4H-1,2,4-triazol-3-yl)pyridin-3-yl)-2-oxo-3,4-dihydropyrazino[2,3-b]pyrazin-1(2H)-yl)methyl)benzonitrile;

1-((trans-4-methoxycyclohexyl)methyl)-7-(4-methyl-6-(1H-1,2,4-triazol-3-yl)pyridin-3-yl)-3,4-dihydropyrazino[2,3-b]pyrazin-2(1H)-one;

3-(7-oxo-8-(2-(tetrahydro-2H-pyran-4-yl)ethyl)-5,6,7,8-tetrahydropyrazino[2,3-b]pyrazin-2-yl)benzamide;

5-(8-((trans-4-methoxycyclohexyl)methyl)-7-oxo-5,6,7,8-tetrahydropyrazino[2,3-b]pyrazin-2-yl)-4-methylpicolinamide;

3-((7-(6-(2-hydroxypropan-2-yl)pyridin-3-yl)-2-oxo-3,4-dihydropyrazino[2,3-b]pyrazin-1(2H)-yl)methyl)benzonitrile;

7-(6-(2-hydroxypropan-2-yl)pyridin-3-yl)-1-((1R,3R)-3-methoxycyclopentyl)-3,4-dihydropyrazino[2,3-b]pyrazin-2(1H)-one;

7-(6-(2-hydroxypropan-2-yl)pyridin-3-yl)-1-((1S,3R)-3-methoxycyclopentyl)-3,4-dihydropyrazino[2,3-b]pyrazin-2(1H)-one;

7-(6-(2-hydroxypropan-2-yl)pyridin-3-yl)-1-((1S,3S)-3-methoxycyclopentyl)-3,4-dihydropyrazino[2,3-b]pyrazin-2(1H)-one;

TABLE A-continued 7-(6-(2-hydroxypropan-2-yl)pyridin-3-yl)-1-((1R,3S)-3-methoxycyclopentyl)-3,4-dihydropyrazino[2,3-b]pyrazin-2(1H)-one;
7-(1H-indazol-6-yl)-1-(2-(tetrahydro-2H-pyran-4-yl)ethyl)-3,4-dihydropyrazino[2,3-b]pyrazin-2(1H)-one;
7-(2-methyl-6-(4H-1,2,4-triazol-3-yl)pyridin-3-yl)-1-(2-morpholinoethyl)-3,4-dihydropyrazino[2,3-b]pyrazin-2(1H)-one;
1-(trans-4-hydroxycyclohexyl)-7-(2-methyl-6-(4H-1,2,4-triazol-3-yl)pyridin-3-yl)-3,4-dihydropyrazino[2,3-b]pyrazin-2(1H)-one;
1-(cis-4-hydroxycyclohexyl)-7-(2-methyl-6-(4H-1,2,4-triazol-3-yl)pyridin-3-yl)-3,4-dihydropyrazino[2,3-b]pyrazin-2(1H)-one;
7-(6-(2-hydroxypropan-2-yl)pyridin-3-yl)-1-(2-morpholinoethyl)-3,4-dihydropyrazino[2,3-b]pyrazin-2(1H)-one;
1-isopropyl-7-(2-methyl-6-(4H-1,2,4-triazol-3-yl)pyridin-3-yl)-3,4-dihydropyrazino[2,3-b]pyrazin-2(1H)-one;
7-(1H-imidazo[4,5-b]pyridin-6-yl)-1-(2-(tetrahydro-2H-pyran-4-yl)ethyl)-3,4-dihydropyrazino[2,3-b]pyrazin-2(1H)-one;
1-((cis-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one;
1-(trans-4-hydroxycyclohexyl)-7-(6-(2-hydroxypropan-2-yl)pyridin-3-yl)-3,4-dihydropyrazino[2,3-b]pyrazin-2(1H)-one;
1-(cis-4-hydroxycyclohexyl)-7-(6-(2-hydroxypropan-2-yl)pyridin-3-yl)-3,4-dihydropyrazino[2,3-b]pyrazin-2(1H)-one;
4-(7-oxo-8-(2-(tetrahydro-2H-pyran-4-yl)ethyl)-5,6,7,8-tetrahydropyrazino[2,3-b]pyrazin-2-yl)benzamide;
7-(1H-indazol-5-yl)-1-(2-(tetrahydro-2H-pyran-4-yl)ethyl)-3,4-dihydropyrazino[2,3-b]pyrazin-2(1H)-one;
7-(1H-pyrrolo[2,3-b]pyridin-5-yl)-1-(2-(tetrahydro-2H-pyran-4-yl)ethyl)-3,4-dihydropyrazino[2,3-b]pyrazin-2(1H)-one;
7-(2-methyl-6-(4H-1,2,4-triazol-3-yl)pyridin-3-yl)-1-(tetrahydro-2H-pyran-4-yl)-3,4-dihydropyrazino[2,3-b]pyrazin-2(1H)-one;
1-((1S,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;
1-((1R,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;
1-((1R,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;
1-((1S,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;
7-(1H-indol-5-yl)-1-(2-(tetrahydro-2H-pyran-4-yl)ethyl)-3,4-dihydropyrazino[2,3-b]pyrazin-2(1H)-one;
1-ethyl-7-(2-methyl-6-(4H-1,2,4-triazol-3-yl)pyridin-3-yl)-3,4-dihydropyrazino[2,3-b]pyrazin-2(1H)-one;
7-(1H-indol-6-yl)-1-(2-(tetrahydro-2H-pyran-4-yl)ethyl)-3,4-dihydropyrazino[2,3-b]pyrazin-2(1H)-one;
7-(4-(2-hydroxypropan-2-yl)phenyl)-1-(trans-4-methoxycyclohexyl)-3,4-dihydropyrazino[2,3-b]pyrazin-2(1H)-one;
7-(6-(2-hydroxypropan-2-yl)pyridin-3-yl)-1-(tetrahydro-2H-pyran-4-yl)-3,4-dihydropyrazino[2,3-b]pyrazin-2(1H)-one;
1-((trans-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one;
7-(6-(2-hydroxypropan-2-yl)pyridin-3-yl)-1-((cis-4-methoxycyclohexyl)methyl)-3,4-dihydropyrazino[2,3-b]pyrazin-2(1H)-one;
1-(2-methoxyethyl)-7-(4-methyl-2-(methylamino)-1H-benzo[d]imidazol-6-yl)-3,4-dihydropyrazino[2,3-b]pyrazin-2(1H)-one;
7-(7-methyl-2-oxo-2,3-dihydro-1H-benzo[d]imidazol-5-yl)-1-((tetrahydro-2H-pyran-4-yl)methyl)-3,4-dihydropyrazino[2,3-b]pyrazin-2(1H)-one;
7-(2-methyl-4-(4H-1,2,4-triazol-3-yl)phenyl)-3,4-dihydropyrazino[2,3-b]pyrazin-2(1H)-one;
1-(2-methoxyethyl)-7-(4-methyl-6-(1H-1,2,4-triazol-3-yl)pyridin-3-yl)-3,4-dihydropyrazino[2,3-b]pyrazin-2(1H)-one;
1-benzyl-7-(2-methyl-4-(4H-1,2,4-triazol-3-yl)phenyl)-3,4-dihydropyrazino[2,3-b]pyrazin-2(1H)-one;
7-(3-fluoro-4-(4H-1,2,4-triazol-3-yl)phenyl)-1-(2-methoxyethyl)-3,4-dihydropyrazino[2,3-b]pyrazin-2(1H)-one;
7-(3-fluoro-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one;
7-(3-fluoro-2-methyl-4-(1H-1,2,4-triazol-3-yl)phenyl)-1-(2-methoxyethyl)-3,4-dihydropyrazino[2,3-b]pyrazin-2(1H)-one;
1-(trans-4-methoxycyclohexyl)-7-(2-methyl-6-(4H-1,2,4-triazol-3-yl)pyridin-3-yl)-3,4-dihydropyrazino[2,3-b]pyrazin-2(1H)-one;
7-(6-(2-hydroxypropan-2-yl)pyridin-3-yl)-1-(trans-4-methoxycyclohexyl)-3,4-dihydropyrazino[2,3-b]pyrazin-2(1H)-one;
7-(5-fluoro-2-methyl-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one;
7-(3-fluoro-2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one;
1-(2-methoxyethyl)-7-(2-methyl-6-(4H-1,2,4-triazol-3-yl)pyridin-3-yl)-3,4-dihydropyrazino[2,3-b]pyrazin-2(1H)-one;

TABLE A-continued 7-(6-(2-hydroxypropan-2-yl)pyridin-3-yl)-1-((trans-4-methoxycyclohexyl)methyl)-3,4-dihydropyrazino[2,3-b]pyrazin-2(1H)-one;
1-(cyclopentylmethyl)-7-(6-(2-hydroxypropan-2-yl)pyridin-3-yl)-3,4-dihydropyrazino[2,3-b]pyrazin-2(1H)-one;
7-(4-(2-hydroxypropan-2-yl)phenyl)-1-(2-methoxyethyl)-3,4-dihydropyrazino[2,3-b]pyrazin-2(1H)-one;
(S)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one;
(R)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one;
7-(2-methyl-6-(4H-1,2,4-triazol-3-yl)pyridin-3-yl)-1-((tetrahydro-2H-pyran-4-yl)methyl)-3,4-dihydropyrazino[2,3-b]pyrazin-2(1H)-one;
7-(4-(2-hydroxypropan-2-yl)phenyl)-1-(2-(tetrahydro-2H-pyran-4-yl)ethyl)-3,4-dihydropyrazino[2,3-b]pyrazin-2(1H)-one;
7-(6-(2-hydroxypropan-2-yl)pyridin-3-yl)-1-(4-(trifluoromethyl)benzyl)-3,4-dihydropyrazino[2,3-b]pyrazin-2(1H)-one;
7-(6-(2-hydroxypropan-2-yl)pyridin-3-yl)-1-(3-(trifluoromethyl)benzyl)-3,4-dihydropyrazino[2,3-b]pyrazin-2(1H)-one;
7-(6-(2-hydroxypropan-2-yl)pyridin-3-yl)-1-(3-methoxypropyl)-3,4-dihydropyrazino[2,3-b]pyrazin-2(1H)-one;
7-(4-methyl-6-(1H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one;
7-(6-(2-hydroxypropan-2-yl)pyridin-3-yl)-1-(2-methoxyethyl)-3,4-dihydropyrazino[2,3-b]pyrazin-2(1H)-one;
7-(6-(2-hydroxypropan-2-yl)pyridin-3-yl)-1-((tetrahydro-2H-pyran-4-yl)methyl)-3,4-dihydropyrazino[2,3-b]pyrazin-2(1H)-one;
7-(4-methyl-2-(methylamino)-1H-benzo[d]imidazol-6-yl)-1-((tetrahydro-2H-pyran-4-yl)methyl)-3,4-dihydropyrazino[2,3-b]pyrazin-2(1H)-one;
7-(2-amino-4-methyl-1H-benzo[d]imidazol-6-yl)-1-((tetrahydro-2H-pyran-4-yl)methyl)-3,4-dihydropyrazino[2,3-b]pyrazin-2(1H)-one;
7-(2-methyl-6-(4H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one;
(R)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one;
(S)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one;
7-(6-(2-hydroxypropan-2-yl)pyridin-3-yl)-3,3-dimethyl-1-(2-(tetrahydro-2H-pyran-4-yl)ethyl)-3,4-dihydropyrazino[2,3-b]pyrazin-2(1H)-one;
7-(2-amino-4-methyl-1H-benzo[d]imidazol-6-yl)-1-(2-(tetrahydro-2H-pyran-4-yl)ethyl)-3,4-dihydropyrazino[2,3-b]pyrazin-2(1H)-one;
7-(6-(2-hydroxypropan-2-yl)pyridin-3-yl)-1-(2-(tetrahydro-2H-pyran-4-yl)ethyl)-3,4-dihydropyrazino[2,3-b]pyrazin-2(1H)-one;
7-(2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one;
7-(4-(1H-1,2,4-triazol-5-yl)phenyl)-1-(2-(tetrahydro-2H-pyran-4-yl)ethyl)-3,4-dihydropyrazino[2,3-b]pyrazin-2(1H)-one;
1-(1-hydroxypropan-2-yl)-7-(2-methyl-6-(1H-1,2,4-triazol-3-yl)pyridin-3-yl)-3,4-dihydropyrazino[2,3-b]pyrazin-2(1H)-one; and
1-(2-hydroxyethyl)-7-(2-methyl-6-(1H-1,2,4-triazol-3-yl)pyridin-3-yl)-3,4-dihydropyrazino[2,3-b]pyrazin-2(1H)-one,
and pharmaceutically acceptable salts, clathrates, solvates, stereoisomers, tautomers, metabolites, isotopologues and prodrugs thereof.

5.3 Methods for Making TOR Kinase Inhibitors

The TOR kinase inhibitors can be obtained via standard, well-known synthetic methodology, see e.g., March, J. Advanced Organic Chemistry; Reactions Mechanisms, and Structure, 4th ed., 1992. Starting materials useful for preparing compounds of formula (III) and intermediates therefore, are commercially available or can be prepared from commercially available materials using known synthetic methods and reagents.

Particular methods for preparing compounds of formula (I) are disclosed in U.S. Pat. No. 8,110,578, issued Feb. 7, 2012, and U.S. Pat. No. 8,569,494, issued Oct. 29, 2013, each incorporated by reference herein in their entirety.

5.4 Compound AA

N-(3-(5-fluoro-2-(4-(2-methoxyethoxy)phenylamino)pyrimidin-4-ylamino)phenyl)acrylamide:

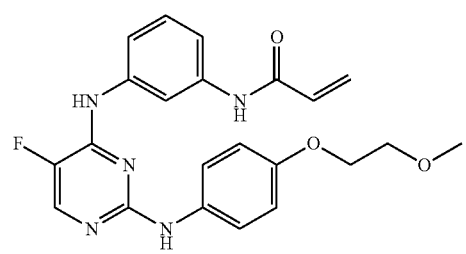

AA and pharmaceutically acceptable salts thereof are referred to herein collectively as "Compound AA." In one embodiment, the besylate salt of Compound AA is used in the compositions and methods provided herein. In one embodiment, the free base of Compound AA is used in the compositions and methods provided herein.

United States published patent application number US 2010/0029610, published Feb. 4, 2010 ("the '610 publication," the entirety of which is hereby incorporated herein by reference), describes Compound AA, which is designated as compound number I-182 in the '610 publication. Compound AA covalently and irreversibly inhibits activity of one or more protein kinases, including BTK, a member of TEC-kinases. The synthesis of Compound AA is described in detail at Example 20 of the '610 publication. Compound AA is active in a variety of assays and therapeutic models demonstrating covalent, irreversible inhibition of BTK (in enzymatic and cellular assays). Notably, Compound AA is a potent, selective, orally available, small molecule which was found to inhibit B-cell proliferation and activation.

5.5 Anti-CD20 Antibodies

CD20, the first B-cell specific antigen defined by the monoclonal antibody tositumomab, plays a critical role in B-cell development. Human CD20 is a 297 amino acid (30- to 35-kDa) phosphoprotein with four transmembrane domains encoded by the gene MS4A1 located on chromosome 11q12.2. CD20 plays a critical role in B-cell development and is a biomarker for immunotherapies targeting B-cell derived diseases. CD20 is an integral membrane protein expressed by B lymphocytes in early stages of differentiation and by most B cell lymphomas, but not by differentiated plasma cells. CD20 remains on the membrane of B cells without dissociation or internalization upon antibody binding. CD20 functions though binding to the Src family of tyrosine kinases, such as Lyn, Fyn and Lck, and believed to be involved as a result in the phosphorylation cascade of intracellular proteins. Anti-CD20 antibodies are broadly classified into type I and type II antibodies. Both types of anti-CD 20 antibodies exhibit equal ability in activating Fc-FcγR interactions such as antibody-dependent cellular cytotoxicity (ADCC) and phagocytosis. Type I anti-CD20 antibodies redistribute CD20 into membrane lipid rafts and potently activate complement-dependent cytotoxicity (CDC). Type II anti-CD20 antibodies weakly activate CDC but more potently induce direct programmed cell death.

A person of ordinary skill in the art can readily identify and select additional anti-CD20 antibodies that are useful in the present invention. For example, in some embodiments, such antibodies are described, for example, in U.S. Pat. Nos. 8,153, 125, 8,147,832, 8,101,179, 8,084,582, 8,057,793 and 7,879, 984, and U.S. Patent Publication Nos. 2011/0129412, 2012/0183545, 2012/0134990 and 2012/0034185.

In some embodiments, an anti-CD20 antibody for use in the present invention is a type I antibody. In some embodiments, an anti-CD20 for use in the present invention is a type II antibody.

In some embodiments, an anti-CD20 antibody is an antibody that binds to a CD20 epitope selected from 170ANPS173 and 182YCYSI185.

In some embodiments, an anti-CD20 antibody has a binding affinity (Kd) for an epitope of CD20 of less than 12 nM, less than 11 nM, less than 10 nM, less than 9 nM, less than 8 nM, less than 7 nM, less than 6 nM, less than 5 nM, less than 4 nM, less than 3 nM, less than 2 nM or less than 1 nM.

Rituximab is but one example of an anti-CD20 antibody. In some embodiments, an anti-CD20 antibody for use in the present invention includes, for example, rituximab (Rituxan® or MabThera®), Gazyva® (i.e., obinutuzumab) and Arzerra® (ofatumumab). For ease of reference, provided methods and regimens detailed herein refer to an exemplary anti-CD20 antibody (i.e., rituximab); however, such reference is not intended to limit the present invention to a single anti-CD20 antibody. Indeed, all references to rituximab, or a biosimilar thereof, are to be read by a person skilled in the art to encompass the class of anti-CD20 antibodies. For example, it will be appreciated that the anti-CD20 antibodies ofatumumab (Arzerra®) or obinutuzumab (Gazyva®) can instead be administered in each instance where reference is made to a CD20 antibody or rituximab. In some such embodiments, ofatumumab is administered in 12 doses according to the following schedule: 300 mg initial dose, followed 1 week later by 2000 mg dose weekly for 7 doses, followed 4 weeks later by 2000 mg every 4 weeks for 4 doses. In some such embodiments, obinutuzumab is administered for six 28-day cycles as follows: 100 mg on day 1, cycle 1; 900 mg on day 2 cycle 1; 1000 mg on days 8 and 15 of cycle 1; and 1000 mg on day 1 of cycles 2-6. Accordingly, in some embodiments, the term "rituximab" encompasses all corresponding anti-CD20 antibodies that fulfill the requirements necessary for obtaining a marketing authorization as an identical or biosimilar product in a country or territory selected from the group of countries consisting of the USA, Europe and Japan.

In some embodiments, an anti-CD20 antibody has the same or similar activity as rituximab, or a biosimilar thereof. In some embodiments, an anti-CD20 antibody binds to the same or similar region or epitope as rituximab or a fragment thereof. In some embodiments, an anti-CD20 antibody competes with the binding of rituximab or a fragment thereof to CD20. In some embodiments, an anti-CD20 antibody is bioequivalent to rituximab or a fragment thereof. In some embodiments, an anti-CD20 antibody is a biosimilar of rituximab or a fragment thereof. In some embodiments, an anti-CD20 antibody is a variant or derivative of rituximab, including functional fragments, derivatives, or antibody conjugates.

Rituximab (Rituxan® or MabThera®) is a genetically engineered cytolytic, chimeric murine/human monoclonal IgG1 kappa antibody directed against the CD20 cell-surface molecule present in normal B lymphocytes and B-cell CLL and in most forms of non-Hodgkin's B-cell lymphomas. Rituximab has a binding affinity for the CD20 antigen of approximately 8.0 nM. Rituximab can induce complement-dependent cellular cytotoxicity (CDC) and antibody-dependent cellular cytotoxicity (ADCC), leading to its clinical activity against lymphoma cells. Rituximab can also lead to apoptosis of B cells upon binding to CD20, thereby leading to direct inhibition of cellular growth.

Rituximab is produced by mammalian cell (Chinese Hamster Ovary) suspension culture in a nutrient medium containing the antibiotic gentamicin. Gentamicin is not detectable in the final product. Rituximab is a sterile, clear, colorless, preservative-free liquid concentrate for intravenous administration. Rituximab is supplied at a concentration of 10 mg/mL in either 100 mg/10 mL or 500 mg/50 mL single-use vials. Rituximab is formulated in polysorbate 80 (0.7 mg/mL), sodium citrate dihydrate (7.35 mg/mL), sodium chloride (9 mg/mL) and water for injection. The pH of Rituxan® (or MabThera®) is 6.5

Rituximab has been investigated in clinical studies and approved for treatment of patients with CLL in combination with fludarabine and cyclophosphamide, as well as patients with rheumatoid arthritis in combination with methotrexate. Rituximab is also approved for treatment of non-Hodgkin's lymphoma, Wegener's Granulomatosis and Microscopic Polyangiitis.

5.6 Methods of Use

Provided herein are methods for treating or preventing a cancer, comprising administering an effective amount of a TOR kinase inhibitor and an effective amount of Compound AA to a patient having a cancer.

In certain embodiments, the cancer is a bloodborne tumor.

In certain embodiments, the cancer is a lymphoma, a leukemia or a multiple myeloma.

In certain embodiments, the cancer is non-Hodgkin's lymphoma. In certain embodiments, the non-Hodgkin's lymphoma is diffuse large B-cell lymphoma (DLBCL), follicular lymphoma (FL), acute myeloid leukemia (AML), mantle cell lymphoma (MCL), or ALK⁺ anaplastic large cell lymphoma. In one embodiment, the non-Hodgkin's lymphoma is advanced solid non-Hodgkin's lymphoma. In one embodiment, the non-Hodgkin's lymphoma is diffuse large B-cell lymphoma (DLBCL).

In certain embodiments, the cancer is diffuse large B-cell lymphoma (DLBCL).

In certain embodiments, the cancer is a B-cell lymphoma.

In certain embodiments, the B-cell lymphoma is a B-cell non-Hodgkin's lymphoma selected from diffuse large B-cell lymphoma, Burkitt's lymphoma/leukemia, mantle cell lymphoma, mediastinal (thymic) large B-cell lymphoma, follicular lymphoma, marginal zone lymphoma (including extranodal marginal zone B-cell lymphoma and nodal marginal zone B-cell lymphoma), lymphoplasmacytic lymphoma/ Waldenstrom macroglobulinemia. In some embodiments, the B-cell lymphoma is chronic lymphocytic leukemia/small lymphocytic lymphoma (CLL/SLL). In one embodiment, the B-cell lymphoma is Waldenstrom macroglobulinemia. In other embodiments, the CLL is characterized as the small lymphocytic lymphoma (SLL) variant of CLL.

In one embodiment, the B-cell non-Hodgkin's lymphoma is refractory B-cell non-Hodgkin's lymphoma. In one embodiment, the B-cell non-Hodgkin's lymphoma is relapsed B-cell non-Hodgkin's lymphoma.

In certain embodiments, the cancer is a T-cell lymphoma.

The B-cell disorders chronic lymphocytic leukemia/small lymphocytic lymphoma (CLL/SLL) represent 2 ends of a spectrum of the same disease process differing in the degree of blood/marrow involvement (CLL) versus lymph node involvement (SLL).

In other embodiments, the cancer is a multiple myeloma.

In certain embodiments, the cancer is a cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, and brain or central nervous system.

In other embodiments, the cancer is a solid tumor. In certain embodiments, the solid tumor is a relapsed or refractory solid tumor.

In one embodiment, the solid tumor is a neuroendocrine tumor. In certain embodiments, the neuroendocrine tumor is a neuroendocrine tumor of gut origin. In certain embodiments, the neuroendocrine tumor is of non-pancreatic origin. In certain embodiments, the neuroendocrine tumor is non-pancreatic of gut origin. In certain embodiments, the neuroendocrine tumor is of unknown primary origin. In certain embodiments, the neuroendocrine tumor is a symptomatic endocrine producing tumor or a nonfunctional tumor. In certain embodiments, the neuroendocrine tumor is locally unresectable, metastatic moderate, well differentiated, low (grade 1) or intermediate (grade 2).

In one embodiment, the solid tumor is non-small cell lung cancer (NSCLC).

In another embodiment, the solid tumor is glioblastoma multiforme (GBM).

In another embodiment, the solid tumor is hepatocellular carcinoma (HCC).

In another embodiment, the solid tumor is breast cancer. In one embodiment, the breast cancer is hormone receptor positive. In one embodiment, the breast cancer is estrogen receptor positive (ER+, ER+/Her2 or ER+/Her2+). In one embodiment, the breast cancer is estrogen receptor negative (ER−/ Her2+). In one embodiment, the breast cancer is triple negative (TN) (breast cancer that does not express the genes and/or protein corresponding to the estrogen receptor (ER), progesterone receptor (PR), and that does not overexpress the Her2/neu protein).

In another embodiment, the solid tumor is colorectal cancer (CRC).

In another embodiment, the solid tumor is salivary cancer.

In another embodiment, the solid tumor is pancreatic cancer.

In another embodiment, the solid tumor is adenocystic cancer.

In another embodiment, the solid tumor is adrenal cancer.

In another embodiment, the solid tumor is esophageal cancer, renal cancer, leiomyosarcoma, or paraganglioma.

In one embodiment, the solid tumor is an advanced solid tumor.

In another embodiment, the cancer is head and neck squamous cell carcinoma.

In another embodiment, the cancer is E-twenty six (ETS) overexpressing castration-resistant prostate cancer.

In another embodiment, the cancer is E-twenty six (ETS) overexpressing Ewings sarcoma.

In other embodiments, the cancer is a cancer associated with the pathways involving mTOR, PI3K, or Akt kinases and mutants or isoforms thereof. Other cancers within the scope of the methods provided herein include those associated with the pathways of the following kinases: PI3Kα, PI3Kβ, PI3Kδ, KDR, GSK3α, GSK3β, ATM, ATX, ATR, cFMS, and/or DNA-PK kinases and mutants or isoforms thereof. In some embodiments, the cancers associated with mTOR/ PI3K/Akt pathways include solid and blood-borne tumors, for example, multiple myeloma, mantle cell lymphoma, diffused large B-cell lymphoma, acute myeloid lymphoma, follicular lymphoma, chronic lymphocytic leukemia; and solid tumors, for example, breast, lung, endometrial, ovarian, gastric, cervical, and prostate cancer; glioblastoma; renal carcinoma; hepatocellular carcinoma; colon carcinoma; neuroendocrine tumors; head and neck tumors; and sarcomas, such as Ewing's sarcoma.

Further provided herein are methods for treating or preventing a cancer, comprising administering an effective amount of Compound AA (e.g., alone or in the absence of a TOR kinase inhibitor) to a patient having a cancer.

In certain embodiments wherein Compound AA is administered alone or in the absence of a TOR kinase inhibitor, the cancer is a cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, and brain or central nervous system.

In other embodiments wherein Compound AA is administered alone or in the absence of a TOR kinase inhibitor, the cancer is a solid tumor. In certain embodiments, the solid tumor is a relapsed or refractory solid tumor.

In one embodiment wherein Compound AA is administered alone or in the absence of a TOR kinase inhibitor, the solid tumor is a neuroendocrine tumor. In certain embodiments, the neuroendocrine tumor is a neuroendocrine tumor of gut origin. In certain embodiments, the neuroendocrine tumor is of non-pancreatic origin. In certain embodiments, the neuroendocrine tumor is non-pancreatic of gut origin. In certain embodiments, the neuroendocrine tumor is of unknown primary origin. In certain embodiments, the neuroendocrine tumor is a symptomatic endocrine producing tumor or a nonfunctional tumor. In certain embodiments, the neuroendocrine tumor is locally unresectable, metastatic moderate, well differentiated, low (grade 1) or intermediate (grade 2).

In one embodiment wherein Compound AA is administered alone or in the absence of a TOR kinase inhibitor, the solid tumor is non-small cell lung cancer (NSCLC).

In another embodiment wherein Compound AA is administered alone or in the absence of a TOR kinase inhibitor, the solid tumor is glioblastoma multiforme (GBM).

In another embodiment wherein Compound AA is administered alone or in the absence of a TOR kinase inhibitor, the solid tumor is hepatocellular carcinoma (HCC).

In another embodiment wherein Compound AA is administered alone or in the absence of a TOR kinase inhibitor, the solid tumor is breast cancer. In one embodiment, the breast cancer is hormone receptor positive. In one embodiment, the breast cancer is estrogen receptor positive (ER+, ER+/Her2 or ER+/Her2+). In one embodiment, the breast cancer is estrogen receptor negative (ER−/Her2+). In one embodiment, the breast cancer is triple negative (TN) (breast cancer that does not express the genes and/or protein corresponding to the estrogen receptor (ER), progesterone receptor (PR), and that does not overexpress the Her2/neu protein).

In another embodiment wherein Compound AA is administered alone or in the absence of a TOR kinase inhibitor, the solid tumor is colorectal cancer (CRC).

In another embodiment wherein Compound AA is administered alone or in the absence of a TOR kinase inhibitor, the solid tumor is salivary cancer.

In another embodiment wherein Compound AA is administered alone or in the absence of a TOR kinase inhibitor, the solid tumor is pancreatic cancer.

In another embodiment wherein Compound AA is administered alone or in the absence of a TOR kinase inhibitor, the solid tumor is adenocystic cancer.

In another embodiment wherein Compound AA is administered alone or in the absence of a TOR kinase inhibitor, the solid tumor is adrenal cancer.

In another embodiment wherein Compound AA is administered alone or in the absence of a TOR kinase inhibitor, the solid tumor is esophageal cancer, renal cancer, leiomyosarcoma, or paraganglioma.

In one embodiment wherein Compound AA is administered alone or in the absence of a TOR kinase inhibitor, the solid tumor is an advanced solid tumor.

In another embodiment wherein Compound AA is administered alone or in the absence of a TOR kinase inhibitor, the cancer is head and neck squamous cell carcinoma.

In another embodiment wherein Compound AA is administered alone or in the absence of a TOR kinase inhibitor, the cancer is E-twenty six (ETS) overexpressing castration-resistant prostate cancer.

In another embodiment wherein Compound AA is administered alone or in the absence of a TOR kinase inhibitor, the cancer is E-twenty six (ETS) overexpressing Ewings sarcoma.

In other embodiments wherein Compound AA is administered alone or in the absence of a TOR kinase inhibitor, the cancer is a cancer associated with the pathways involving mTOR, PI3K, or Akt kinases and mutants or isoforms thereof.

Other cancers within the scope of the methods provided herein include those associated with the pathways of the following kinases: PI3Kα, PI3Kβ, PI3Kδ, KDR, GSK3α, GSK3β, ATM, ATX, ATR, cFMS, and/or DNA-PK kinases and mutants or isoforms thereof. In some embodiments, the cancers associated with mTOR/PI3K/Akt pathways include solid and blood-borne tumors, for example, multiple myeloma, mantle cell lymphoma, diffused large B-cell lymphoma, acute myeloid lymphoma, follicular lymphoma, chronic lymphocytic leukemia; and solid tumors, for example, breast, lung, endometrial, ovarian, gastric, cervical, and prostate cancer; glioblastoma; renal carcinoma; hepatocellular carcinoma; colon carcinoma; neuroendocrine tumors; head and neck tumors; and sarcomas, such as Ewing's sarcoma.

In certain embodiments wherein Compound AA is administered alone or in the absence of a TOR kinase inhibitor, the cancer is acute myeloid leukemia.

In certain embodiments wherein Compound AA is administered alone or in the absence of a TOR kinase inhibitor, the cancer is ALK$^+$ anaplastic large cell lymphoma.

In certain embodiments wherein Compound AA is administered alone or in the absence of a TOR kinase inhibitor, the cancer is a T-cell lymphoma.

In certain embodiments, provided herein are methods for achieving an International Workshop on Chronic Lymphocytic Leukemia (IWCLL) response definition of a complete response, partial response or stable disease in a patient having chronic lymphocytic leukemia, comprising administering an effective amount of a TOR kinase inhibitor in combination with Compound AA to said patient. In certain embodiments, provided herein are methods for achieving a Response Evaluation Criteria in Solid Tumors (for example, RECIST 1.1) of complete response, partial response or stable disease in a patient having a solid tumor, comprising administering an effective amount of a TOR kinase inhibitor in combination with Compound AA to said patient. In certain embodiments, provided herein are methods for achieving a National Cancer Institute-Sponsored Working Group on Chronic Lymphocytic Leukemia (NCI-WG CLL) response definition of complete response, partial response or stable disease in a patient having leukemia, comprising administering an effective amount of a TOR kinase inhibitor in combination with Compound AA to said patient. In certain embodiments, provided herein are methods for achieving a Prostate Cancer Working Group 2 (PCWG2) Criteria of complete response, partial response or stable disease in a patient having prostate cancer, comprising administering an effective amount of a TOR kinase inhibitor in combination with Compound AA to said patient. In certain embodiments, provided herein are methods for achieving an International Workshop Criteria (IWC) for non-Hodgkin's lymphoma of complete response, partial response or stable disease in a patient having non-Hodgkin's lymphoma, comprising administering an effective amount of a TOR kinase inhibitor in combination with Compound AA to said patient. In certain embodiments, provided herein are methods for achieving an International Uniform Response Criteria (IURC) for multiple myeloma of complete response, partial response or stable disease in a patient having multiple myeloma, comprising administering an effective amount of a TOR kinase inhibitor in combination with Compound AA to said patient. In certain embodiments, provided herein are methods for achieving a Responses Assessment for Neuro-Oncology (RANO) Working Group for glioblastoma multiforme of complete response, partial response or stable disease in a patient having glioblastoma multiforme, comprising administering an effective amount of a TOR kinase inhibitor in combination with Compound AA to said patient.

In certain embodiments, provided herein are methods for increasing survival without disease progression of a patient having a cancer, comprising administering an effective amount of a TOR kinase inhibitor in combination with an effective amount of Compound AA to said patient.

In certain embodiments, provided herein are methods for treating a cancer, the methods comprising administering an effective amount of a TOR kinase inhibitor in combination with an effective amount of Compound AA to a patient having a cancer, wherein the treatment results in prevention or retarding of clinical progression, such as cancer-related cachexia or increased pain.

In some embodiments, provided herein are methods for treating a cancer, the methods comprising administering an effective amount of a TOR kinase inhibitor in combination with an effective amount of Compound AA to a patient having a B-cell lymphoma, wherein the treatment results in one or more of inhibition of disease progression, increased Time To Progression (TTP), increased Progression Free Survival (PFS), and/or increased Overall Survival (OS), among others.

In some embodiments, the TOR kinase inhibitor is a compound as described herein. In one embodiment, the TOR kinase inhibitor is a compound of formula (I). In one embodiment, the TOR kinase inhibitor is a compound from Table A. In one embodiment, the TOR kinase inhibitor is Compound 1 (a TOR kinase inhibitor set forth herein having molecular formula $C_{21}H_{27}N_5O_3$). In one embodiment, the TOR kinase inhibitor is Compound 2 (a TOR kinase inhibitor set forth herein having molecular formula $C_{16}H_{16}N_8O$). In one embodiment, the TOR kinase inhibitor is Compound 3 (a TOR kinase inhibitor set forth herein having molecular formula $C_{20}H_{25}N_5O_3$). In one embodiment, Compound 1 is 7-(6-(2-hydroxypropan-2-yl)pyridin-3-yl)-1-((1r,4r)-4-methoxycyclohexyl)-3,4-dihydropyrazino-[2,3-b]pyrazin-2(1H)-one, alternatively named 7-(6-(2-hydroxypropan-2-yl)pyridin-3-yl)-1-((trans)-4-methoxycyclohexyl)-3,4-dihydropyrazino[2,3-b]pyrazin-2(1H)-one, or 7-(6-(2-hydroxypropan-2-yl)pyridin-3-yl)-1-((1R*,4R*)-4-methoxycyclohexyl)-3,4-dihydropyrazino[2,3-b]pyrazin-2(1H)-one. In another embodiment, Compound 2 is 1-ethyl-7-(2-methyl-6-(1H-1,2,4-triazol-3-yl)pyridin-3-yl)-3,4-dihydropyrazino[2,3-b]pyrazin-2(1H)-one, or a tautomer thereof, for example, 1-ethyl-7-(2-methyl-6-(4H-1,2,4-triazol-3-yl)pyridin-3-yl)-3,4-dihydropyrazino[2,3-b]pyrazin-2(1H)-one, or 1-ethyl-7-(2-methyl-6-(1H-1,2,4-triazol-5-yl)pyridin-3-yl)-3,4-dihydropyrazino[2,3-b]pyrazin-2(1H)-one. In another embodiment, Compound 3 is 1-((trans)-4-hydroxycyclohexyl)-7-(6-(2-hydroxypropan-2-yl)pyridin-3-yl)-3,4-dihydropyrazino[2,3-b]pyrazin-2(1H)-one, alternatively named 1-((1r,4r)-4-hydroxycyclohexyl)-7-(6-(2-hydroxypropan-2-yl)pyridin-3-yl)-3,4-dihydropyrazino[2,3-b]pyrazin-2(1H)-one. In one embodiment, Compound 3 is a metabolite of Compound 1.

A TOR kinase inhibitor administered in combination with Compound AA can be further combined with radiation therapy or surgery. In certain embodiments, a TOR kinase inhibitor is administered in combination with Compound AA to patient who is undergoing radiation therapy, has previously undergone radiation therapy or will be undergoing radiation therapy. In certain embodiments, a TOR kinase inhibitor is administered in combination with Compound AA to a patient who has undergone surgery, such as tumor removal surgery.

Further provided herein are methods for treating patients who have been previously treated for a cancer, as well as those who have not previously been treated. Because patients with a cancer have heterogenous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with a cancer.

In one embodiment, a TOR kinase inhibitor is administered in combination with Compound AA and an anti-CD20 antibody, for example, rituximab (Rituxan® or MabThera®). Accordingly, provided herein are methods for treating or preventing a cancer, comprising administering an effective amount of a TOR kinase inhibitor, an effective amount of Compound AA and an effective amount of an anti-CD20 antibody, for example, rituximab (Rituxan® or MabThera®) to a patient having a cancer. In a specific embodiment, Compound 1 is administered in combination with Compound AA and an anti-CD20 antibody, for example, rituximab (Rituxan® or MabThera®). In a particular embodiment, the cancer treated or prevented with a combination of a TOR kinase inhibitor, Compound AA and an anti-CD20 antibody, for example, rituximab (Rituxan® or MabThera®) is diffuse large B-cell lymphomas (DLBCL).

In certain embodiments, a TOR kinase inhibitor is administered in combination with Compound AA to a patient in cycles. Cycling therapy involves the administration of an active agent(s) for a period of time, followed by a rest for a period of time, and repeating this sequential administration. Cycling therapy can reduce the development of resistance, avoid or reduce the side effects, and/or improves the efficacy of the treatment. The administration of a TOR kinase inhibitor, Compound AA and an anti-CD20 antibody, for example, rituximab (Rituxan® or MabThera®), in combination can also be carried out in such cycles.

In some embodiments, Compound AA is administered twice daily, or BID, whereas a TOR kinase inhibitor is administered once daily, or QD. Alternatively and/or additionally, Compound AA may be administered once or twice daily for one or more 28 day cycles, whereas a TOR kinase inhibitor may be administered once daily for days 1 through 21 of one or more 28-day cycles. In some embodiments, Compound AA is administered twice daily on days 1 through 28 of one or more 28-day cycles and a TOR kinase inhibitor is administered once daily on days 2 through 22 of one or more 28-day cycles. In some embodiments, Compound AA is administered twice daily on days 1 through 28 of one or more 28-day cycles and a TOR kinase inhibitor is administered once daily on days 1 through 28 of one or more 28-day cycles.

In some embodiments, a TOR kinase inhibitor is administered once daily, or QD, Compound AA is administered twice daily, or BID, and an anti-CD20 antibody, for example, rituximab (Rituxan® or MabThera®), is administered once monthly or once every 4 weeks. Alternatively and/or additionally, in one or more 28-day cycles, a TOR kinase inhibitor may be administered once daily, Compound AA may be administered once or twice daily and an anti-CD20 antibody, for example, rituximab (Rituxan® or MabThera®), may be administered once.

In some embodiments, provided methods comprise administering Compound AA in combination with a TOR kinase inhibitor daily for a period of 1, 2, 3, 4, 5, 6, 7, 8, 9, 10, 11, 12, 13, 14, 15, 16, 17, 18, 19, 20, 21, 22, 23, 24, 25, 26, 27 or 28 days. In some embodiments, a treatment regimen comprises at least one 28-day cycle. As used herein, the term "28-day cycle" means that the combination of Compound AA and a TOR kinase inhibitor is administered to a patient in need thereof for 28 consecutive days. In some embodiments, the combination of Compound AA and a TOR kinase inhibitor is administered for at least one 28-day cycle. In some embodiments, the combination of Compound AA and a TOR kinase inhibitor is administered for at least two, at least three, at least four, at least five or at least six 28-day cycles. In some embodiments, the combination of Compound AA and a TOR kinase inhibitor is administered for at least seven, at least eight, at least nine, at least ten, at least eleven or at least twelve 28-day cycles. In some embodiments, the combination of Compound AA and a TOR kinase inhibitor is administered for at least thirteen, at least fourteen, at least fifteen, at least sixteen, at least seventeen or at least eighteen 28-day cycles.

In some embodiments, the combination of Compound AA and a TOR kinase inhibitor is administered for at least eighteen 28-day cycles, and Compound AA is further administered for at least one additional 28-day cycle. In some embodiments, the combination of Compound AA and a TOR kinase inhibitor is administered for at least eighteen 28-day cycles, and Compound AA is further administered for at least two, at least three, at least four, at least five, at least six, at least seven, at least eight, at least nine, at least ten, at least eleven or at least twelve additional 28-day cycles. In some embodiments, the combination of Compound AA and a TOR kinase inhibitor is administered for at least eighteen 28-day cycles, and Compound AA is further administered for at least thirteen, at least fourteen, at least fifteen, at least sixteen, at least seventeen, at least eighteen, at least nineteen, at least twenty, at least twenty-one, at least twenty-two, at least twenty-three or at least twenty-four additional 28-day cycles. In some embodiments, the combination of Compound AA and a TOR kinase inhibitor is administered to a patient for the duration of the patient's life. In some embodiments, the combination of Compound AA and a TOR kinase inhibitor is administered for at least eighteen 28-day cycles, and Compound AA is further administered for the duration of the patient's life. In some embodiments, Compound AA is administered on days 1 through 28 (for example, one dose each day or two doses each day) of each 28-day cycle and Compound AA is administered on days 1 through 21 (for example, one dose each day) of one or more 28-day cycles. In some embodiments, Compound AA is administered on days 1 through 28 of one or more 28-day cycles and Compound AA is administered on days 2 through 22 of one or more 28-day cycles.

In some embodiments, two adjacent 28-day cycles may be separated by a rest period. Such a rest period may be one, two, three, four, five, six, seven or more days during which the patient is not administered either or both Compound AA and a TOR kinase inhibitor. In a preferred embodiment, two adjacent 28-day cycles are continuous.

In one embodiment, a TOR kinase inhibitor is administered in combination with Compound AA daily in single or divided doses for about 3 days, about 5 days, about one week, about two weeks, about three weeks, about four weeks (e.g., 28 days), about five weeks, about six weeks, about seven weeks, about eight weeks, about ten weeks, about fifteen weeks, or about twenty weeks, followed by a rest period of about 1 day to about ten weeks. In one embodiment, the methods provided herein contemplate cycling treatments of about one week, about two weeks, about three weeks, about four weeks, about five weeks, about six weeks, about eight weeks, about ten weeks, about fifteen weeks, or about twenty weeks. In some embodiments, a TOR kinase inhibitor is administered in combination with Compound AA in single or divided doses for about 3 days, about 5 days, about one week, about two weeks, about three weeks, about four weeks (e.g., 28 days), about five weeks, or about six weeks with a rest period of about 1, 2, 3, 4, 5, 6, 7, 8, 9, 10, 12, 14, 16, 18, 20, 22, 24, 26, 28, 29, or 30 days. In some embodiments, the rest period is 1 day. In some embodiments, the rest period is 3 days. In some embodiments, the rest period is 7 days. In some embodiments, the rest period is 14 days. In some embodiments, the rest period is 28 days. The frequency, number and length of dosing cycles can be increased or decreased.

In one embodiment, the methods provided herein comprise: i) administering to the subject a first daily dose of a TOR kinase inhibitor in combination with Compound AA; ii) optionally resting for a period of at least one day where Compound AA is not administered to the subject; iii) administering a second dose of a TOR kinase inhibitor in combination with Compound AA to the subject; and iv) repeating steps ii) to iii) a plurality of times.

In one embodiment, the methods provided herein comprise administering to the subject a dose of Compound AA on day 1, followed by administering a TOR kinase inhibitor in combination with Compound AA to the subject on day 2 and subsequent days.

In certain embodiments, a TOR kinase inhibitor in combination with Compound AA is administered continuously for between about 1 and about 52 weeks. In certain embodiments, a TOR kinase inhibitor in combination with Compound AA is administered continuously for about 0.5, 1, 2, 3, 4, 5, 6, 7, 8, 9, 10, 11, or 12 months. In certain embodiments, a TOR kinase inhibitor in combination with Compound AA is administered continuously for about 7, about 14, about 21, about 28, about 35, about 42, about 84, or about 112 days.

In certain embodiments, when a TOR kinase inhibitor is administered in combination with Compound AA, the TOR kinase inhibitor is administered continuously for 28 days, while Compound AA is administered continuously for 21 days followed by 7 days without administration of Compound AA. In one embodiment, in a 28 day cycle, Compound AA is administered alone on Day 1, Compound AA and the TOR kinase inhibitor are administered in combination on Days 2-21 and the TOR kinase inhibitor is administered alone on Days 22-28. In some such embodiments, starting with Cycle 2 both Compound AA and the TOR kinase inhibitor are administered on Day 1, Compound AA is continued through Day 21, while the TOR kinase inhibitor is continued through Day 28. The 28 day cycles, as described above, can be continued for as long needed, such as for 1, 2, 3, 4, 5, 6, 7, 8, 9, 10, 11 or 12 months or longer.

In certain embodiments, when a TOR kinase inhibitor is administered in combination with Compound AA, in a 28 day cycle, Compound AA is administered alone on Days 1-7 and the TOR kinase inhibitor is administered alone on Days 8-28. Such 28 day cycles can be continued for as long needed, such as for 1, 2, 3, 4, 5, 6, 7, 8, 9, 10, 11 or 12 months or longer.

In certain embodiments, when a TOR kinase inhibitor is administered in combination with Compound AA, the TOR kinase inhibitor is administered at an amount of about 2.5 mg to about 50 mg per day (such as about 2.5 mg, about 10 mg, about 15 mg, about 16 mg/day, about 20 mg, about 30 mg or about 45 mg per day) and Compound AA is administered at an amount of about 25 mg to about 1250 mg per day (such as about 25 mg, about 50 mg, about 75 mg, about 100 mg, about 125 mg, about 150 mg, about 175 mg, about 200 mg, about 225 mg, about 250 mg, about 375 mg, about 500 mg, about 750 mg, about 1000 mg or about 1250 mg per day). In certain embodiments, about 2.5 mg per day of a TOR kinase inhibitor is administered in combination with about 25 mg, about 50 mg, about 75 mg, about 100 mg, about 125 mg, about 150 mg, about 175 mg, about 200 mg, about 225 mg, about 250 mg, about 375 mg, about 500 mg, about 750 mg, about 1000 mg or about 1250 mg per day of Compound AA. In certain embodiments, about 10 mg per day of a TOR kinase inhibitor is administered in combination with about 25 mg, about 50 mg, about 75 mg, about 100 mg, about 125 mg, about 150 mg, about 175 mg, about 200 mg, about 225 mg, about 250 mg, about 375 mg, about 500 mg, about 750 mg, about 1000 mg or about 1250 mg per day of Compound AA. In certain embodiments, about 15 mg per day of a TOR kinase inhibitor is administered in combination with about 25 mg, about 50 mg, about 75 mg, about 100 mg, about 125 mg, about 150 mg, about 175 mg, about 200 mg, about 225 mg, about 250 mg, about 375 mg, about 500 mg, about 750 mg, about 1000 mg or about 1250 mg per day of Compound AA. In certain embodiments, about 16 mg per day of a TOR kinase inhibitor is administered in combination with about 25 mg, about 50 mg, about 75 mg, about 100 mg, about 125 mg, about 150 mg, about 175 mg, about 200 mg, about 225 mg, about 250 mg, about 375 mg, about 500 mg, about 750 mg, about 1000 mg or about 1250 mg per day of Compound AA. In certain embodiments, about 20 mg per day of a TOR kinase inhibitor is administered in combination with about 25 mg, about 50 mg, about 75 mg, about 100 mg, about 125 mg, about 150 mg, about 175 mg, about 200 mg, about 225 mg, about 250 mg, about 375 mg, about 500 mg, about 750 mg, about 1000 mg or about 1250 mg per day of Compound AA. In certain embodiments, about 30 mg per day of a TOR kinase inhibitor is administered in combination with about 25 mg, about 50 mg, about 75 mg, about 100 mg, about 125 mg, about 150 mg, about 175 mg, about 200 mg, about 225 mg, about 250 mg, about 375 mg, about 500 mg, about 750 mg, about 1000 mg or about 1250 mg per day of Compound AA. In certain embodiments, about 45 mg per day of a TOR kinase inhibitor is administered in combination with about 25 mg, about 50 mg, about 75 mg, about 100 mg, about 125 mg, about 150 mg, about 175 mg, about 200 mg, about 225 mg, about 250 mg, about 375 mg, about 500 mg, about 750 mg, about 1000 mg or about 1250 mg per day of Compound AA. A TOR kinase inhibitor and Compound AA can each be independently administered once (QD), twice (BD) or three times (TID) per day.

In some embodiments, methods provided herein comprise administering to a patient in need thereof a therapeutically effective amount of a TOR kinase inhibitor in combination with Compound AA, wherein the therapeutically effective amount of Compound AA is about 250 mg to about 1250 mg per day. In some embodiments, the therapeutically effective amount of Compound AA is administered as one or more discreet doses. For example, in some embodiments, a therapeutically effective amount of Compound AA is 250 mg per day, wherein the therapeutically effective amount is administered as 125 mg twice daily (BID). In some embodiments, a therapeutically effective amount of Compound AA is 500 mg per day, wherein the therapeutically effective amount is administered as 250 mg twice daily (BID). In some embodiments, a therapeutically effective amount of Compound AA is 750 mg per day, wherein the therapeutically effective amount is administered as 375 mg twice daily (BID). In some embodiments, a therapeutically effective amount of Compound AA is 1000 mg per day, wherein the therapeutically effective amount is administered as 500 mg twice daily (BID).

In some embodiments, methods provided herein comprise administering to a patient in need thereof a therapeutically effective amount of a TOR kinase inhibitor in combination with Compound AA, wherein the therapeutically effective amount of Compound AA is about 125 mg to about 1250 mg per day, or about 125 mg to about 1125 mg per day, or about 125 mg to about 1000 mg per day, or about 125 mg to about 875 mg per day, or about 125 mg to about 750 mg per day, or about 125 mg to about 625 mg per day, or about 125 mg to about 500 mg per day, or about 125 mg to about 375 mg per day, or about 125 mg to about 250 mg per day, or about 250 mg to about 1250 mg per day, or about 250 mg to about 1125 mg per day, or about 250 mg to about 1000 mg per day, or about 250 mg to about 875 mg per day, or about 250 mg to about 750 mg per day, or about 250 mg to about 625 mg per day, or about 250 mg to about 500 mg per day, or about 250 mg to about 375 mg per day, or about 375 mg to about 1250 mg per day, or about 375 mg to about 1125 mg per day, or about 375 mg to about 1000 mg per day, or about 375 mg to about 875 mg per day, or about 375 mg to about 750 mg per day, or about 375 mg to about 625 mg per day, or about 375 mg to about 500 mg per day, or about 500 mg to about 1250 mg per day, or about 500 mg to about 1125 mg per day, or about 500 mg to about 1000 mg per day, or about 500 mg to about 875 mg per day, or about 500 mg to about 750 mg per day, or about 500 mg to about 625 mg per day, or about 625 mg to about 1250 mg per day, or about 625 mg to about 1125 mg per day, or about 625 mg to about 1000 mg per day, or about 625 mg to about 875 mg per day, or about 625 mg to about 750 mg per day, or about 750 mg to about 1250 mg per day, or about 750 mg to about 1125 mg per day, or about 750 mg to about 1000 mg per day, or about 875 mg to about 1250 mg per day, or about 875 mg to about 1125 mg per day, or about 875 mg to about 1000 mg per day.

In some embodiments, methods provided herein comprise administering to a patient in need thereof a therapeutically effective amount of a TOR kinase inhibitor in combination with Compound AA, wherein the therapeutically effective amount of Compound AA per day is about 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, 800 mg, 805 mg, 810 mg, 815 mg, 820 mg, 825 mg, 830 mg, 835 mg, 840 mg, 845 mg, 850 mg, 855 mg, 860 mg, 865 mg, 870 mg, 875 mg, 880 mg, 885 mg, 890 mg, 895 mg, 900 mg, 905 mg, 910 mg, 915 mg, 920 mg, 925 mg, 930 mg, 935 mg, 940 mg, 945 mg, 950 mg, 955 mg, 960 mg, 965 mg, 970 mg, 975 mg, 980 mg, 985 mg, 990 mg, 995 mg, 1000 mg, 1005 mg, 1010 mg, 1015 mg, 1020 mg, 1025 mg, 1030 mg, 1035 mg, 1040 mg, 1045 mg, 1050 mg, 1055 mg, 1060 mg, 1065 mg, 1070 mg, 1075 mg, 1080 mg, 1085 mg, 1090 mg, 1095 mg, 1100 mg, 1105 mg, 1110 mg, 1115 mg, 1120 mg, 1125 mg, 1130 mg, 1135 mg, 1140 mg, 1145 mg, 1150 mg, 1155 mg, 1160 mg, 1165 mg, 1170 mg, 1175 mg, 1180 mg, 1185 mg, 1190 mg, 1195 mg, 1200 mg, 1205 mg, 1210 mg, 1215 mg, 1220 mg, 1225 mg, 1230 mg, 1235 mg, 1240 mg, 1245 mg or 1250 mg.

In some embodiments, the methods of treatment provided herein comprise administering to a patient in need thereof about 125 mg BID to about 500 mg BID Compound AA in combination with about 2.5 mg to about 50 mg per day (such as about 2.5 mg, about 10 mg, about 15 mg, about 16 mg/day, about 20 mg, about 30 mg or about 45 mg per day) of a TOR kinase inhibitor. In some embodiments, provided methods comprise administering to a patient in need thereof 375 mg BID to about 500 mg BID Compound AA in combination with about 2.5 mg to about 50 mg (such as about 2.5 mg, about 10 mg, about 15 mg, about 16 mg/day, about 20 mg, about 30 mg or about 45 mg per day) of a TOR kinase inhibitor.

In certain embodiments, when a TOR kinase inhibitor is administered in combination with Compound AA, the TOR kinase inhibitor:Compound AA ratio is from about 1:1 to about 1:10. In certain embodiments, when a TOR kinase inhibitor is administered in combination with Compound AA, the TOR kinase inhibitor:Compound AA ratio is less than about 1:1, less than about 1:3 or less than about 1:10. In certain embodiments, when a TOR kinase inhibitor is administered in combination with Compound AA, the TOR kinase inhibitor:Compound AA ratio is about 1:1, about 1:3 or about 1:10.

In certain embodiments, the methods provided herein further comprise the administration of an anti-CD20 antibody, for example, rituximab (Rituxan® or MabThera®), in combination with a TOR kinase inhibitor and Compound AA, wherein the amount of an anti-CD20 antibody, for example, rituximab (Rituxan® or MabThera®), administered is about 250 mg/m$^2$ to about 500 mg/m$^2$ once per 28 days, the amount of a TOR kinase inhibitor administered is about 10 mg to about 40 mg daily and the amount of Compound AA is about 250 mg to about 750 mg BID. In a particular embodiment, the methods provided herein further comprise the administration of an anti-CD20 antibody, for example, rituximab (Rituxan® or MabThera®), in combination with a TOR kinase inhibitor and Compound AA, wherein the amount of an anti-CD20 antibody, for example, rituximab (Rituxan® or MabThera®), administered is about 375 mg/m$^2$ or about 500 mg/m$^2$ once per 28 days, the amount of a TOR kinase inhibitor administered is about 20 mg or about 30 mg daily and the amount of Compound AA administered is about 375 mg or about 500 mg BID.

In some embodiments, provided methods comprise administering to a patient in need thereof a pharmaceutical composition comprising rituximab, wherein rituximab is administered as an infusion at a rate of 50 mg/hr. In some embodiments, the infusion rate of rituximab is increased by 50 mg/hr every 30 minutes, to a maximum of 400 mg/hr. In some embodiments, the infusion rate of rituximab is increased by 100 mg/hr every 30 minutes, to a maximum of 400 mg/hr. Accordingly, in some embodiments, the infusion rate of rituximab is 100 mg/hr. In some embodiments, the infusion rate of rituximab is 150 mg/hr. In some embodiments, the infusion rate of rituximab is 200 mg/hr. In some embodiments, the infusion rate of rituximab is 250 mg/hr. In some embodiments, the infusion rate of rituximab is 300 mg/hr. In some embodiments, the infusion rate of rituximab is 350 mg/hr. In some embodiments, the infusion rate of rituximab is 400 mg/hr.

In some embodiments, 375 mg/m$^2$ rituximab is administered on cycle 1 day 2, and 500 mg/m$^2$ rituximab is administered on cycle 2 day 1. In some embodiments, 375 mg/m$^2$ rituximab is administered on cycle 1 day 2, and 500 mg/m$^2$ rituximab is administered on each of cycle 2 day 1 and cycle 3 day 1. In some embodiments, 375 mg/m$^2$ rituximab is administered on cycle 1 day 2, and 500 mg/m$^2$ rituximab is administered on each of cycle 2 day 1, cycle 3 day 1 and cycle 4 day 1. In some embodiments, 375 mg/m$^2$ rituximab is administered on cycle 1 day 2, and 500 mg/m$^2$ rituximab is administered on each of cycle 2 day 1, cycle 3 day 1, cycle 4 day 1 and cycle 5 day 1. In some embodiments, 375 mg/m$^2$ rituximab is administered on cycle 1 day 2, and 500 mg/m$^2$ rituximab is administered on each of cycle 2 day 1, cycle 3 day 1, cycle 4 day 1, cycle 5 day 1 and cycle 6 day 1.

In certain embodiments, each of the methods provided herein comprises administering an effective amount of Compound AA (e.g., alone or in the absence of a TOR kinase inhibitor) to a patient having a cancer.

5.7 Pharmaceutical Compositions and Routes of Administration

Provided herein are compositions comprising an effective amount of a TOR kinase inhibitor and an effective amount of Compound AA and compositions comprising an effective amount of a TOR kinase inhibitor and Compound AA and a pharmaceutically acceptable carrier or vehicle.

In some embodiments, the pharmaceutical compositions described herein are suitable for oral, parenteral, mucosal, transdermal or topical administration.

The compositions can be administered to a patient orally or parenterally in the conventional form of preparations, such as capsules, microcapsules, tablets, granules, powder, troches, pills, suppositories, injections, suspensions and syrups. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the TOR kinase inhibitor in the pharmaceutical composition may be at a level that will exercise the desired effect; for example, about 0.005 mg/kg of a patient's body weight to about 10 mg/kg of a patient's body weight in unit dosage for both oral and parenteral administration.

The dose of a TOR kinase inhibitor and the dose of Compound AA to be administered to a patient is rather widely variable and can be subject to the judgment of a healthcare practitioner. In general, the TOR kinase inhibitors and Compound AA can be administered one to four times a day in a dose of about 0.005 mg/kg of a patient's body weight to about 10 mg/kg of a patient's body weight in a patient, but the above dosage may be properly varied depending on the age, body weight and medical condition of the patient and the type of administration. In one embodiment, the dose is about 0.01 mg/kg of a patient's body weight to about 5 mg/kg of a patient's body weight, about 0.05 mg/kg of a patient's body weight to about 1 mg/kg of a patient's body weight, about 0.1 mg/kg of a patient's body weight to about 0.75 mg/kg of a patient's body weight or about 0.25 mg/kg of a patient's body weight to about 0.5 mg/kg of a patient's body weight. In one embodiment, one dose is given per day. In any given case, the amount of the TOR kinase inhibitor administered will depend on such factors as the solubility of the active component, the formulation used and the route of administration.

In another embodiment, provided herein are unit dosage formulations that comprise between about 1 mg and about 2000 mg, about 1 mg and about 200 mg, about 35 mg and about 1400 mg, about 125 mg and about 1000 mg, about 250 mg and about 1000 mg, about 500 mg and about 1000 mg, about 1 mg to about 30 mg, about 1 mg to about 25 mg or about 2.5 mg to about 20 mg of a TOR kinase inhibitor alone or in combination with Compound AA. In another embodiment, provided herein are unit dosage formulations that comprise 1 mg, 2.5 mg, 5 mg, 7.5 mg, 8 mg, 10 mg, 15 mg, 20 mg, 30 mg, 35 mg, 45 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a TOR kinase inhibitor alone or in combination with Compound AA. In another embodiment, provided herein are unit dosage formulations that comprise about 2.5 mg, about 7.5 mg, about 8 mg, about 10 mg, about 15 mg, about 20 mg, about 30 mg or about 45 mg of a TOR kinase inhibitor alone or in combination with Compound AA.

In a particular embodiment, provided herein are unit dosage formulations comprising about 7.5 mg, about 8 mg, about 10 mg, about 15 mg, about 30 mg, about 45 mg, about 50 mg, about 75 mg, about 100 mg or about 400 mg of a TOR kinase inhibitor in combination with Compound AA. In a particular embodiment, provided herein are unit dosage formulations comprising about 5 mg, about 7.5 mg or about 10 mg of a TOR kinase inhibitor in combination with Compound AA.

In certain embodiments, provided herein are unit dosage formulations comprising about 25 mg, about 50 mg, about 75 mg, about 100 mg, about 125 mg, about 150 mg, about 175 mg, about 200 mg, about 225 mg or about 250 mg of Compound AA alone or in combination with a TOR kinase inhibitor.

In certain embodiments, provided herein are unit dosage formulations wherein the TOR kinase inhibitor:Compound AA ratio is from about 1:1 to about 1:10. In certain embodiments, provided herein are unit dosage formulations wherein the TOR kinase inhibitor:Compound AA ratio is less than about 1:1, less than about 1:3 or less than about 1:10. In certain embodiments, provided herein are unit dosage formulations wherein the TOR kinase inhibitor:Compound AA ratio is about 1:1, about 1:3 or about 1:10.

A TOR kinase inhibitor can be administered in combination with Compound AA once, twice, three, four or more times daily.

A TOR kinase inhibitor can be administered in combination with Compound AA orally for reasons of convenience. In one embodiment, when administered orally, a TOR kinase inhibitor in combination with Compound AA is administered with a meal and water. In another embodiment, the TOR kinase inhibitor in combination with Compound AA is dispersed in water or juice (e.g., apple juice or orange juice) and administered orally as a suspension. In another embodiment, when administered orally, a TOR kinase inhibitor in combination with Compound AA is administered in a fasted state.

The TOR kinase inhibitor can also be administered in combination with Compound AA intravenously, such as intravenous infusion, or subcutaneously, such as subcutaneous injection. The mode of administration is left to the discretion of the healthcare practitioner, and can depend in-part upon the site of the medical condition.

In one embodiment, provided herein are capsules containing a TOR kinase inhibitor in combination with Compound AA without an additional carrier, excipient or vehicle.

In another embodiment, provided herein are compositions comprising an effective amount of a TOR kinase inhibitor, an effective amount of Compound AA, and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a TOR kinase inhibitor with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. In one embodiment, the pharmaceutical composition is lactose-free. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders. Illustrative tablet formulations comprising Compound 1 are provided herein.

A lubricant might be necessary in a tablet formulation to prevent the tablet and punches from sticking in the die. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a TOR kinase inhibitor in combination with Compound AA as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the TOR kinase inhibitor in combination with Compound AA can be delayed or prolonged by proper formulation. For example, a slowly soluble pellet of the TOR kinase inhibitor in combination with Compound AA can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the TOR kinase inhibitor in combination with Compound AA in oily or emulsified vehicles that allow it to disperse slowly in the serum.

In some embodiments, a pharmaceutically acceptable composition comprising Compound AA comprises from about 5% to about 60% of Compound AA, or a pharmaceutically acceptable salt thereof, based upon total weight of the composition. In some embodiments, a pharmaceutically acceptable composition comprising Compound AA comprises from about 5% to about 15% or about 7% to about 15% or about 7% to about 10% or about 9% to about 12% of Compound AA, based upon total weight of the composition. In some embodiments, provided methods comprise administering to a patient in need thereof a pharmaceutically acceptable composition comprising from about 25% to about 75% or about 30% to about 60% or about 40% to about 50% or about 40% to about 45% of Compound AA, based upon total weight of the formulation. In certain embodiments, provided regimens comprise administering to a patient in need thereof a pharmaceutically acceptable composition comprising from about 6%, about 7%, about 8%, about 9%, about 10%, about 11%, about 12%, about 13%, about 20%, about 30%, about 40%, about 41%, about 42%, about 43%, about 44%, about 45%, about 50%, about 60%, about 70%, or about 75% of Compound AA, based upon total weight of given composition or formulation.

In certain embodiments, Compound 1 is administered in a formulation set forth in U.S. Patent Application Publication No. 2013-0142873, published Jun. 6, 2013, which is incorporated herein in its entirety (see particularly paragraph [0323] to paragraph [0424], and paragraph [0636] to paragraph [0655]). In other embodiments, Compound 1 is administered in a formulation set forth in U.S. Provisional Patent Application No. 61/828,506, filed May 29, 2013, which is incorporated herein in its entirety (see particularly paragraph [0246] to paragraph [0403], and paragraph [0571] to paragraph [0586]).

In certain embodiments, the Compound 2 is administered in a formulation set forth in U.S. Provisional Application No. 61/813,064, filed Apr. 17, 2013, which is incorporated herein in its entirety (see particularly paragraph [0168] to paragraph [0189] and paragraph [0262] to paragraph [0294]). In other embodiments, the Compound 2 is administered in a formulation set forth in U.S. Provisional Patent Application No. 61/911,201, filed Dec. 3, 2013, which is incorporated herein in its entirety (see particularly paragraph [0170] to paragraph [0190], and paragraph [0264] to paragraph [0296]).

5.8 Kits

In certain embodiments, provided herein are kits comprising a TOR kinase inhibitor and Compound AA.

In certain embodiments, provided herein are kits comprising one or more unit dosage forms of a TOR kinase inhibitor, such as those described herein, and one or more unit dosage forms of Compound AA, such as those described herein.

In some embodiments, the kits described herein additionally comprise an anti-CD-20 antibody, for example, rituximab (Rituxan® or MabThera®).

In certain embodiments, the kits provided herein further comprise instructions for use, such as for administering a TOR kinase inhibitor and Compound AA.

6. EXAMPLES

6.1 Biochemical Assays mTOR HTR-FRET Assay.

The following is an example of an assay that can be used to determine the TOR kinase inhibitory activity of a test compound. TOR kinase inhibitors were dissolved in DMSO and prepared as 10 mM stocks and diluted appropriately for the experiments. Reagents were prepared as follows:

"Simple TOR buffer" (used to dilute high glycerol TOR fraction): 10 mM Tris pH 7.4, 100 mM NaCl, 0.1% Tween-20, 1 mM DTT. Invitrogen mTOR (cat#PV4753) was diluted in this buffer to an assay concentration of 0.200 µg/mL.

ATP/Substrate solution: 0.075 mM ATP, 12.5 mM $MnCl_2$, 50 mM Hepes, pH 7.4, 50 mM β-GOP, 250 nM Microcystin LR, 0.25 mM EDTA, 5 mM DTT, and 3.5 µg/mL GST-p70S6.

Detection reagent solution: 50 mM HEPES, pH 7.4, 0.01% Triton X-100, 0.01% BSA, 0.1 mM EDTA, 12.7 µg/mL Cy5-αGST Amersham (Cat#PA92002V), 9 ng/mL α-phospho p70S6 (Thr389) (Cell Signaling Mouse Monoclonal #9206L), 627 ng/mL α-mouse Lance Eu (Perkin Elmer Cat#AD0077).

To 20 µL of the Simple TOR buffer is added 0.5 µL of test compound in DMSO. To initiate the reaction 5 µL of ATP/Substrate solution was added to 20 µL of the Simple TOR buffer solution (control) and to the compound solution prepared above. The assay was stopped after 60 min by adding 5 µL of a 60 mM EDTA solution; 10 µL of detection reagent solution was then added and the mixture was allowed to sit for at least 2 hours before reading on a Perkin-Elmer Envision Microplate Reader set to detect LANCE Eu TR-FRET (excitation at 320 nm and emission at 495/520 nm).

TOR kinase inhibitors were tested in the TOR HTR-FRET assay and were found to have activity therein, with certain compounds having an $IC_{50}$ below 10 µM in the assay, with some compounds having an $IC_{50}$ between and 0.005 nM and 250 nM, others having an $IC_{50}$ between and 250 nM and 500 nM, others having an $IC_{50}$ between 500 nM and 1 µM, and others having an $IC_{50}$ between 1 µM and 10 µM.

DNA-PK Assay.

DNA-PK assay is performed using the procedures supplied in the Promega DNA-PK assay kit (catalog #V7870). DNA-PK enzyme can be purchased from Promega (Promega cat#V5811).

Selected TOR kinase inhibitors as described herein have, or are expected to have, an $IC_{50}$ below 10 µM in this assay, with some TOR kinase inhibitors as described herein having an $IC_{50}$ below 1 µM, and others having an $IC_{50}$ below 0.10 µM.

6.2 Cell Based Assays

DLBCL Cell Proliferation Assay.

DLBCL cell proliferation was assessed by the $^3$H-thymidine incorporation assay. Briefly, cells were cultured in 96-well cell culture plates in the presence or absence of Compound 1, Compound AA (besylate salt), or both. Each well contained 6000 cells/80 µL cell culture medium (Roswell Park Memorial Institute (RPMI)-1640+10-20% fetal bovine serum (FBS), 1% pen/strep/1% L-glutamine). Compound dilutions were made in 10× the required final concentration, and 10 µL of each compound was added to the cells in triplicate. The cells were treated with drugs in a final concentration of 0.2% dimethyl sulfoxide (DMSO) for all samples. Cells were grown at 37° C. in a humidified incubator at 5% $CO_2$ for 72 hours in the presence of the test compounds. One microcurie of $^3$H-thymidine (GE Healthcare, Fairfield, Conn.) was added to each well for the final 6 hours of culture. The cells were harvested onto UniFilter-96 GF/C filter plates (PerkinElmer, Waltham, Mass.) using a cell harvester (Tomtec, Hamden, Conn.), and the plates were allowed to dry overnight. A total of 25 μL/well of Microscint™-20 (PerkinElmer) was added and the plates were analyzed in TopCount NXT (PerkinElmer). Each well was counted for 1 minute. The percentage inhibition of cell proliferation was calculated by averaging all triplicates and normalizing to the DMSO control (0% inhibition). Final cumulative half-maximal inhibitory concentrations ($IC_{50}$) were calculated using non-linear regression and sigmoidal dose response, constraining the top to 100% and bottom to 0% and allowing variable slope, using GraphPad Prism version 5.01. SEM (standard error of the mean) was calculated from the individual $IC_{50}$s of each replicate.

Cell Lines.

The effect on cell proliferation of Compound 1 alone or in combination with Compound AA was evaluated on GCB DLBCL cell lines (SuDHL6, SuDHL10, HT, Farage, Pfeifer), ABC DLBCL cell lines (OCI-Ly10, U2932, OCI-Ly3), and DHIT (double hit, i.e. cMyc and Bcl-2 mutant) GCB DLBCL cell lines (Karpas 422, WSU-DLBCL2).

Data Analysis.

Theoretical additivity was calculated using the fractional product method and plotted as a separate curve. If the observed combination effect was greater than the theoretical additivity at two or more concentrations and error bars between theoretical additivity curve and combination curves did not overlap, synergy was assigned. All data was generated with n=3.

Results:

Synergy was observed upon treatment with the combination of Compound 1 and Compound AA in the following DLBCL cell lines: SuDHL6, SuDHL10 and Pfeiffer (GCB DLBCL sub types).

6.3 In Vivo Assays

DLBCL Xenograft Model.

Severe combined immunodeficiency (SCID) mice were implanted with human DLBCL cell line (WSU-DLCL2) into the flank. Treatment of compounds started between Day 11 and Day 14 after cell inoculation. Randomized groups of mice (n=9 to 10/group) were treated with the single agents (Compound 1, Compound A or Compound AA) or the combination of Compound 1/Compound A, Compound A/Compound AA, or Compound 1/Compound AA. Compounds were administered orally on a once daily (Compound 1 and Compound A) or twice daily (C) schedule for 21 days. The positive control consisted of CHOP therapy (combination of cyclophosphamide, doxorubicin, vincristine and prednisone). Compound 1 and Compound A were formulated in CMC-Tween (carboxymethylcellulose/Tween 80/deionized water). Compound AA was suspended in DSP (dimethylsulphoxide/solutol/phosphate buffered saline).

Initial studies were conducted in order to determine the antitumor activity of Compound 1 and to identify a dose level for the combination studies. In the WSU-DLCL2 xenograft model, Compound 1 inhibited tumor growth in a dose-dependent fashion. By the end of the 3-week dosing period, a 51%, 28%, and 22% tumor volume reduction (TVR) was observed in 10, 3, and 1 mg/kg Compound 1-treated animals, respectively, when compared with vehicle control (FIG. 1). In a subsequent combination study, Compound 1 was dosed at 10 mg/kg, once daily (QD). Compound A and Compound AA were dosed at 30 mg/kg (QD) and 50 mg/kg (BID), respectively. In this combination study, Compound 1 and Compound A demonstrated significant antitumor activity as single agents with a TVR of 29% and 30%, respectively, whereas Compound AA was inactive in this model (FIGS. 2-3). The combination of Compound 1 and Compound A produced a highly significant (p<0.001), synergistic inhibition of tumor growth (64%) in the WSU-DLCL2 xenograft model (FIG. 2). The antitumor activity of the combination of Compound 1 and Compound AA was not significantly different from that of Compound 1 as a single agent (FIG. 3). Similarly, the antitumor activity of the combination of Compound A and Compound AA was not significantly different from that of Compound A as a single agent in the WSU-DLCL2 xenograft model.

OCI-Ly10 DLBCL Xenograft Model.

OCI-Ly10 cells are derived from a diffuse-large B-cell lymphoma, a type of non-Hodgkins lymphoma. In brief, female CB.17 SCID mice are inoculated with $5\times10^6$ OCI-Ly10 cells subcutaneously, and tumor are allowed to grow to approximately 50-300 mm$^3$. The mice bearing xenograft with similarly sized tumors are pooled together and randomized into various treatment groups. A typical efficacy study design involves administering one or more compounds at various dose levels and schedules, based on prior single agent studies, to tumor-bearing mice. Tumor volume is measured biweekly for approximately 28 days of treatment using calipers, and tumor volume is calculated using standard methods, for example, using the formula of $W^2\times L/2$. Tumor volume can optionally be measured further post-treatment. Statistical analysis will be performed using standard statistical methods.

6.4 Clinical Protocol

A Phase 1B, Multi-Center, Open-Label Study of Novel Combinations and Rituximab in Diffuse Large B Cell Lymphoma.

This study is a Phase 1B, multi-center, open-label study of the TOR kinase inhibitor Compound 1, Compound A (3-(5-Amino-2-methyl-4-oxoquinazolin-3(4H)-yl)-piperidine-2,6-dione), and Compound AA (N-(3-(5-fluoro-2-(4-(2-methoxyethoxy)phenylamino)pyrimidin-4-ylamino)phenyl) acrylamide), when administered in combination and in combination with rituximab, in subjects having Diffuse Large B Cell Lymphoma (DLBCL).

The primary objective of the study is to determine the safety and tolerability of Compound A, Compound 1 and Compound AA, when administered orally as doublets and in combination with rituximab, and to define the non-tolerated dose (NTD) and the maximum tolerated dose (MTD) of each combination. The secondary objectives of the study are to provide information on the preliminary efficacy of each drug combination and to characterize the pharmacokinetics (PK) of Compound A, Compound 1 (and the M1 metabolite) and Compound AA following oral administration as single agents and after combination treatment to assess drug-drug interactions.

Study Design.

This study is a phase 1B dose escalation clinical study of Compound A, Compound 1 and Compound AA administered orally as doublets, and as triplets in combination with rituximab, in subjects with relapsed/refractory DLBCL who have failed at least one line of standard therapy. The study will explore two drug doses for each novel agent using a standard 3+3 dose escalation design with higher dose cohorts including the addition of a fixed dose of rituximab. Treatment arms include: Compound A+rituximab (Arm A), Compound A+Compound 1+/−rituximab (Arm B), Compound A+Compound AA+/−rituximab (Arm C) and Compound AA+Compound 1+/−rituximab (Arm D).

All treatments will be administered in 28-day cycles. Compound A, Compound 1 and Compound AA, are administered orally on continuous dosing schedules either once daily (QD)

or twice daily (BID) on days 1-28 of each 28-day cycle. Rituximab, when included in the regimen, will employ a standard fixed dose (375 mg/m²) administered intravenously (IV) on Day 1 of each 28-day cycle only. All three compounds will be explored at two dose levels including: Compound A (2.0 and 3.0 mg QD), Compound 1 (20 and 30 mg QD), and Compound AA (375 and 500 mg BID). The highest two doublet dose levels for Arms B, C, and D will explore the doublets with and without rituximab.

A standard "3+3" dose escalation design will be used to identify initial toxicity of each combination. Subjects will be assigned to study treatment arms based on Investigator choice and open slots. Cohorts of 3 subjects will take study drugs in defined dose increments and, in the event of dose-limiting toxicity (DLT) in 1 of 3 evaluable subjects, cohorts will be expanded to 6 subjects.

An evaluable subject for DLT is defined as one that received at least 80% of the planned doses of Compound A, Compound 1 or Compound AA during Cycle 1; received at least 80% of the planned dose of rituximab during Cycle 1 (in rituximab containing cohorts only); and experienced study drug-related DLT after receiving at least one dose of any study drug. Non-evaluable subjects not due to DLT will be replaced. Additional subjects within any dose cohort may be enrolled at the discretion of the Safety Review Committee (SRC).

A dose will be considered the non-tolerated dose (NTD) when 2 of 6 evaluable subjects in a cohort experience drug-related DLT in Cycle 1. The maximum tolerated dose (MTD) is defined as the last dose level below the NTD with 0 or 1 out of 6 evaluable subjects experiencing DLT during Cycle 1. If 2 of 6 DLT are observed at the first dose level with either combination, a lower dose combination may be explored at the discretion of the SRC. An intermediate dose of Compound 1 (one between the NTD and the last dose level before the NTD) may be evaluated to accurately determine the MTD of the combination.

Following completion of dose escalation, selected combination treatment arms may be expanded up to approximately 20 subjects per arm. Expansion may occur at the MTD established in the dose escalation phase, or at an alternative tolerable combination dose level, based on review of study data.

Paired tumor biopsies for analysis of genetic abnormalities, gene expression and biomarkers of treatment activity are optional in the dose escalation phase but mandatory during the dose expansion phase.

The study population will consist of men and women, 18 years or older, with relapsed or refractory DLBCL, with disease progression following at least one standard first-line treatment regimen. Prior autologous stem cell transplant (greater than 3 months prior to enrollment) is allowed.

Enrollment is expected to take approximately 24 months (18 months for dose escalation, 6 months for expansion). Completion of active treatment and post-treatment follow-up is expected to take 6-12 additional months. The entire study is expected to last approximately 3 years.

Dose levels to be explored in this Phase 1b study are shown below:

If unacceptable toxicity occurs at dose level 1, one starting dose reduction for Compound A (1 mg QD) and Compound 1 (15 mg QD) is allowed. No starting dose reductions for Compound AA are planned.

For Arms A and C, the Compound A dose will be reduced; for Arm D, the Compound 1 dose will be reduced. For Arm B, the safety review committee (SRC) will determine which of the two drugs in the doublet to dose reduce.

In Arm A (Compound A+rituximab), dose escalation will proceed from dose level 1 to 3b, since only Compound A is escalated. In Arms B, C and D dose levels 2b (doublet+rituximab) and 3a (dose escalation of doublet without rituximab) may be enrolled concurrently once dose level 2a (doublet) has been cleared. Both dose levels 2b and 3a must be cleared to move to dose level 3b.

Compound A, Compound 1 and Compound AA will be dosed daily and rituximab will be dosed on Day 1 of each 28-day cycle. For both the dose escalation and expansion phases, slight modifications to the dosing schedule will occur during Cycle 1 in order to facilitate PK and PD evaluation of each drug alone and in combination. Starting with Cycle 2 and thereafter, all oral drugs will start on Day 1 and continue through Day 28 and rituximab will be administered on Day 1.

Administration of study drugs during Cycle 1 is described below:

In Arm B: Compound 1 will be initiated on Cycle 1 Day 1 followed by PK and PD sampling and continue through Day 28. Compound A will be initiated on Cycle 1 Day 2 and continue through Day 28. Rituximab will be administered on Cycle 1 Day 8.

In Arm C: Compound A will be initiated on Cycle 1 Day 1 followed by PK and PD sampling and continue through Day 28. Compound AA will be initiated on Cycle 1 Day 2 and continue through Day 28. Rituximab will be administered on Cycle 1 Day 8.

In Arm D: Compound 1 will be initiated on Cycle 1 Day 1 followed by PK and PD sampling and continue through Day 28. Compound AA will be initiated on Cycle 1 Day 2 and continue through Day 28. Rituximab will be administered on Cycle 1 Day 8.

After the first dose is administered on Day 1 in any cohort, subjects will be observed for at least 28 days before the next higher protocol-specified dose cohort can begin. Intra-subject dose escalation of study drugs is not permitted during Cycle 1 but may be permitted in cycles beyond Cycle 1 if approved by the SRC. Dose reduction and temporary interruption of one or both drugs due to toxicity is allowed, but dose reduction during Cycle 1 will constitute DLT.

Study treatment may be discontinued if there is evidence of disease progression, unacceptable toxicity or subject/physician decision to withdraw. Subjects may continue to receive study drugs beyond disease progression at the discretion of the Investigator.

| | Arm A | | Arm B | | | Arm C | | | Arm D | | |
|---|---|---|---|---|---|---|---|---|---|---|---|
| Dose Level | Cmpd A (mg/ daily) | Ritux (mg/m² D1q28) | Cmpd A (mg daily) | Cmpd 1 (mg daily) | Ritux (mg/m² D1q28) | Cmpd A (mg/bid daily) | Cmpd AA (mg daily) | Ritux (mg/m² D1q28) | Cmpd 1 (mg daily) | Cmpd AA (mg bid daily) | Ritux (mg/m² D1q28) |
| 1 | 2 | 375 | 2 | 20 | | 2 | 375 | | 20 | 375 | |
| 2a | | | 2 | 30 | | 2 | 500 | | 20 | 500 | |
| 2b | | | 2 | 30 | 375 | 2 | 500 | 375 | 20 | 500 | 375 |
| 3a | | | 3 | 30 | | 3 | 500 | | 30 | 500 | |
| 3b | 3 | 375 | 3 | 30 | 375 | 3 | 500 | 375 | 30 | 500 | 375 |

The estimated total number of subjects to be enrolled during dose escalation is approximately 50 to 100, depending on cohort size. Approximately 30 to 60 additional subjects (10-20 per selected regimen) will be evaluated for safety, PK, PD, and preliminary antitumor effects during the expansion phase.

Subjects will be evaluated for efficacy after every 2 cycles through Cycle 6, every 3 cycles through Cycle 12 and every 6 months thereafter. All treated subjects will be included in the efficacy analyses. The primary efficacy variable is tumor response rate. Tumor response will be determined by the Investigator, based on International Workshop Criteria (IWC) for NHL/DLBCL.

The safety variables for this study include adverse events (AEs), safety clinical laboratory variables, 12-lead electrocardiograms (ECGs), left ventricular ejection fraction (LVEF) assessments, physical examinations, vital signs, exposure to study treatment, assessment of concomitant medications, and pregnancy testing for females of child bearing potentials (FCBP).

During dose escalation, the decision to either evaluate a higher dose level or declare an MTD will be determined by the SRC, based on their review of all available clinical and laboratory safety data for a given dose cohort.

The SRC will also select the dose and schedule of treatment regimens of interest for cohort expansion. One or more regimens may be selected for cohort expansion. The SRC will continue to review safety data regularly throughout the study and make recommendations about study continuation and dose modification, as appropriate.

The concentration-time profiles of Compound A, Compound 1 and Compound AA will be determined from serial blood samples collected after administration of study drugs as single agents and after combination treatment.

The effect of Compound A and Compound AA on Compound 1 and M1 PK will be assessed, as will the effect of Compound AA on Compound A PK. Systemic exposure of Compound A, Compound 1 and the M1 metabolite, and Compound AA will be correlated with safety, PD and activity outcomes.

6.5 Clinical Protocol B

A Phase 1B, Multi-Center, Open-Label Study of Novel Combinations and Rituximab in Diffuse Large B Cell Lymphoma.

This study is a Phase 1B, multi-center, open-label study of the TOR kinase inhibitor Compound 1, Compound A (3-(5-Amino-2-methyl-4-oxoquinazolin-3(4H)-yl)-piperidine-2,6-dione), and Compound AA (N-(3-(5-fluoro-2-(4-(2-methoxyethoxy)phenylamino)pyrimidin-4-ylamino)phenyl)acrylamide), when administered in combination and in combination with rituximab, in subjects having Diffuse Large B Cell Lymphoma (DLBCL).

The primary objective of the study is to determine the safety and tolerability of Compound A, Compound 1 and Compound AA, when administered orally as doublets and as triplets in combination with rituximab, determine the safety and tolerability of Compound A when administered in combination with rituximab, and to define the non-tolerated dose (NTD) and the maximum tolerated dose (MTD) and/or the recommended phase 2 dose (RP2D) of each combination. The secondary objectives of the study are to provide information on the preliminary efficacy of each drug combination and to characterize the steady state pharmacokinetics (PK) of Compound A, Compound 1 and Compound AA following combination oral administration as single agents.

Study Design.

This study is a phase 1b dose escalation and expansion clinical study of Compound A, Compound 1 and Compound AA administered orally as doublets, and as triplets in combination with rituximab, as well as a Compound A plus rituximab doublet, in subjects with relapsed/refractory DLBCL who have failed at least one line of standard therapy. The dose escalation phase of the study will explore one or more drug doses for each novel agent using a standard 3+3 dose escalation design with higher dose cohorts including the addition of a fixed dose of rituximab, followed by expansion of selected cohorts of interest. The addition of rituximab can also be evaluated at the doublet MTD if the higher dose levels are not reached. Treatment arms include: Compound A+Compound 1+/−rituximab (Arm A), Compound A+Compound AA+/−rituximab (Arm B), Compound AA+Compound 1+/−rituximab (Arm C), and Compound A+rituximab (Arm D).

All treatments will initially be administered in 28-day cycles. Compound A, Compound 1 and Compound AA, will initially be administered orally on continuous dosing schedules either once daily (QD) or twice daily (BID) on days 1 to 28 of each 28-day cycle. Rituximab, when included in the regimen, will be administered only once in each cycle as a standard fixed intravenous (IV) dose of 375 mg/m$^2$ on Day 8 of Cycle 1, and Day 1 of each subsequent cycle. All three compounds will be explored at one or two dose levels including: Compound A (2.0 and 3.0 mg QD), Compound 1 (20 and 30 mg QD), and Compound AA (500 mg BID). The highest two doublet dose levels (or the MTD if at a lower dose level) will explore the combinations with rituximab.

A standard "3+3" dose escalation design will be used to identify initial toxicity of each combination. Subjects will be assigned to study treatment arms based on investigator choice and open slots. Cohorts of 3 subjects will take study drugs in defined dose increments and, in the event of dose-limiting toxicity (DLT) in 1 of 3 evaluable subjects, cohorts will be expanded to 6 subjects.

An evaluable subject for DLT is defined as one that received at least 80% of the planned doses of Compound A, Compound 1 or Compound AA during Cycle 1 without experiencing a DLT, and received at least 80% of the planned dose of rituximab during Cycle 1 (in rituximab containing cohorts only); without experiencing a DLT, or experienced a DLT after receiving at least one dose of any study drug. Non-evaluable subjects will be replaced. Additional subjects within any dose cohort may be enrolled at the discretion of the Safety Review Committee (SRC).

A dose will be considered the NTD when 2 of 6 evaluable subjects in a cohort experience a drug-related DLT in Cycle 1. The MTD is defined as the last dose level(s) below the NTD with 0 or 1 out of 6 evaluable subjects experiencing a DLT during Cycle 1. If 2 of 6 DLTs are observed at the first dose level with either combination, a lower dose combination may be explored at the discretion of the SRC. An intermediate dose of study drugs (one between the NTD and the last dose level before the NTD) may be evaluated to accurately determine the MTD of the combination. Alternative schedules reducing the total exposure of study drug during a cycle may also be evaluated for tolerability.

Following completion of dose escalation, selected combination treatment arms may be expanded up to approximately 20 subjects per arm. Expansion may occur at the MTD established in the dose escalation phase, or at an alternative tolerable combination dose level, based on review of study data.

Paired tumor biopsies for analysis of genetic abnormalities, RNA and protein expression, and biomarkers of treatment activity are optional in the dose escalation phase but mandatory during the dose expansion phase.

The study population will consist of men and women, 18 years or older, with relapsed or refractory DLBCL, with disease progression following at least two prior standard treatment regimens and autologous stem cell transplant (ASCT) in chemotherapy sensitive patients are eligible. Enrollment will also include selected high-risk subjects prior to ASCT and subjects not otherwise eligible for ASCT.

Inclusion Criteria:

Subjects must satisfy all of the following criteria to be enrolled in the study: (1) Understand and voluntarily sign an informed consent document prior to conducting any study related assessments or procedures; (2) Consent to retrieve archival tumor tissue for analysis (in the event that archival tissue is not available an exception may be granted by the Sponsor); (3) Consent to undergo paired tumor biopsies (Screening and on treatment) for genetic analysis and biomarker evaluation (expansion cohorts only) (waiver to this requirement may be given under exceptional circumstances); (4) Men and women, 18 years or older, with histologically or cytologically-confirmed, relapsed or refractory DLBCL (including transformed low grade lymphoma) following at least two prior standard treatment regimens (eg, R—CHOP or similar first-line regimen and at least one second-line salvage regimen) and ASCT in chemotherapy sensitive patients, with the following exceptions: (i) Subjects in the pre-ASCT setting with poor prognosis, defined as primary refractory disease, relapse within 12 months following first-line treatment, "double-hit" lymphomas with Bcl-2/Myc gene rearrangements or overexpression, or high IPI score (2,3) at relapse; (ii) Subjects age >65 refusing, or not otherwise appropriate, per the Investigator's judgment, for ASCT; (5) At least one site of measurable disease (>1.5 cm in the long axis or >1.0 cm in both the long and short axis); (6) ECOG PS of 0 or 1; (7) Subjects must have the following laboratory values: (i) Absolute Neutrophil Count (ANC) $\geq 1.5 \times 10^9$/L without growth factor support for 7 days; (ii) Hemoglobin (Hgb) $\geq 8$ g/dL; (iii) Platelets (plt) $\geq 50 \times 10^9$/L without transfusion for 7 days (14 days if received pegfilgrastim); (iv) Potassium within normal limits or correctable with supplements; (v) AST/SGOT and ALT/SGPT $\leq 2.5 \times$ Upper Limit of Normal (ULN) or $\leq 5.0 \times$ ULN if liver tumor is present; (vi) Serum bilirubin $\leq 1.5 \times$ ULN; (vii) Estimated serum creatinine clearance of $\geq 50$ mL/min using the Cockcroft-Gault equation; (8) Females of childbearing potential (FCBP) (A female of childbearing potential is a sexually mature woman who 1) has not undergone a hysterectomy (the surgical removal of the uterus) or bilateral oophorectomy (the surgical removal of both ovaries) or 2) has not been naturally postmenopausal for at least 24 consecutive months (ie, has had menses at any time during the preceding 24 consecutive months) must: (i) Agree to use at least two effective contraceptive methods (oral, injectable, or implantable hormonal contraceptive; tubal ligation; intrauterine device; barrier contraceptive with spermicide; or vasectomized partner), one of which must be barrier, throughout the study, and for up to 28 days following the last dose of study drug; (ii) Have a negative serum pregnancy test (sensitivity of at least 25 mIU/mL) at Screening; (iii) Have a negative serum or urine pregnancy test (investigator's discretion) within 72 hours prior to Cycle 1 Day −1 of study treatment (note that the Screening serum pregnancy test can be used as the test prior to Day −1 study treatment if it is performed within the prior 72 hours); (iv) Avoid conceiving for 28 days after the last dose of any study drug; (v) Agree to ongoing pregnancy testing during the course of the study; (9) Males must practice complete abstinence or agree to use a condom (a latex condom is recommended) during sexual contact with a pregnant female or a female of childbearing potential and will avoid conceiving while participating in the study, during dose interruptions, and for at least 28 days following study drug discontinuation, even if he has undergone a successful vasectomy; (10) All subjects enrolled into treatment arms receiving Compound A must: (i) Understand that the (investigational product) IP could have a potential teratogenic risk; (ii) Agree to abstain from donating blood or sperm while taking IP and for at least 28 days following discontinuation of IP; (iii) Agree not to share IP with another person; (iv) Be counseled about pregnancy precautions and risks of fetal exposure and agree to requirements of PPRMP; (11) Able to adhere to the study visit schedule and other protocol requirements.

Exclusion Criteria:

The presence of any of the following will exclude a subject from enrollment: (1) Symptomatic central nervous system involvement; (2) Known symptomatic acute or chronic pancreatitis; (3) Persistent diarrhea or malabsorption $\geq$NCI CTCAE grade 2, despite medical management; (4) Peripheral neuropathy $\geq$NCI CTCAE grade 2; (5) Impaired cardiac function or clinically significant cardiac diseases, including any of the following: (i) LVEF <45% as determined by MUGA or ECHO; (ii) Complete left bundle branch or bifascicular block (iii) Congenital long QT syndrome; (iv) Persistent or clinically meaningful ventricular arrhythmias; (v) QTcF >460 msec on Screening ECG (mean of triplicate recordings); (vi) Unstable angina pectoris or myocardial infarction $\leq 3$ months prior to starting study drugs; (vii) Troponin-T value >0.4 ng/ml or BNP >300 pg/mL (Subjects with baseline troponin-T >ULN or BNP >100 pg/mL are eligible but must have cardiologist evaluation prior to enrollment in the trial for baseline assessment and optimization of cardioprotective therapy); (6) Subjects with diabetes on active treatment or subjects with either of the following (for subjects treated on Compound 1 containing arms only): (i) Fasting blood glucose (FBG) $\geq 126$ mg/dL (7.0 mmol/L); (ii) HbA1c $\geq 6.5$%; (7) Prior ASCT $\leq 3$ months before first dose; (8) Prior allogeneic stem cell transplant with either standard or reduced intensity conditioning; (9) Prior systemic cancer-directed treatments or investigational modalities $\leq 5$ half lives or 4 weeks prior to starting study drugs, whichever is shorter; (10) Prior treatment with a dual mTORC1/mTORC2 inhibitor (Compound 1 only) or BTK inhibitor (Compound AA arms only) (Prior treatment with rapamycin analogues, PI3K or AKT inhibitors, lenalidomide and rituximab are allowed); (11) Subjects who have undergone major surgery $\leq 2$ weeks prior to starting study drugs (subjects must have recovered from any effects of recent surgery or therapy that might confound the safety evaluation of study drug; no specific washout is required for radiotherapy); (12) Women who are pregnant or breast feeding (adults of reproductive potential not employing two forms of birth control); (13) Subjects with known HIV infection; (14) Subjects with known chronic active hepatitis B or C virus (HBV/HCV) infection; (15) Subjects with treatment-related myelodysplastic syndrome; (16) Chronic use of proton pump inhibitors or H2 antagonists or their use within 7 days of first dose for subjects treated on Compound AA-containing arms (B and C). Subjects with chronic gastroesophageal reflux disease, dyspepsia, and peptic ulcer disease, should be carefully evaluated for their suitability for this treatment prior to enrollment in this study (these medications are prohibited concomitant medications throughout the study); (17) Any other significant medical condition, laboratory abnormality, or psychiatric illness which places the subject at unacceptable risk or that would prevent the subject from complying with the study; (18) History of concurrent second cancers requiring active, ongoing systemic treatment.

Enrollment is expected to take approximately 24 months to complete (18 months for dose escalation, and 6 months for expansion). Completion of active treatment and post-treatment follow-up is expected to take—an additional 6-12 months. The entire study is expected to last approximately 3 years.

The End of Trial is defined as either the date of the last visit of the last subject to complete the study, or the date of receipt of the last data point from the last subject that is required for primary, secondary and/or exploratory analysis, as pre-specified in the protocol and/or the Statistical Analysis Plan, whichever is the later date.

Dose levels to be explored in this Phase 1b study are shown below:

| Dose Level | Arm A | | Arm B | | Arm C | | Arm D | Arms A, B, C, D Ritux |
|---|---|---|---|---|---|---|---|---|
| | Cmpd A (mg QD) | Cmpd 1 (mg QD) | Cmpd A (mg QD) | Cmpd AA (mg BID) | Cmpd 1 (mg QD) | Cmpd AA (mg BID) | Cmpd A (mg QD) | (mg/m$^2$) (q 28) |
| 1 | 2 | 20 | — | — | — | — | | — |
| 2 | 2 | 30 | 2 | 500 | 20 | 500 | | — |
| 3 | 2 | 30 | 2 | 500 | 20 | 500 | 2 | 375 |
| 4 | 3 | 30 | 3 | 500 | 30 | 500 | 3 | 375 |

BID = twice a day; QD = once a day; q 28 = once every 28 days (Day 8 in Cycle 1; Day 1 in subsequent cycles); Ritux = rituximab All treatment cycles are 28 days in length. Dosing will start at Dose Level 1 for Arm A, Dose Level 2 for Arms B and C and Dose Level 3 for Arm D. Each dose level must clear before initiating the next higher dose level. If unacceptable toxicity occurs at the initial dose level, dose reductions for Compound A (1.5 mg QD and 1 mg QD) and Compound 1 (15 mg QD) are allowed. Additionally, exploration of an alternative schedule of Compound A (daily for 5 out of 7 days) is allowed based on SRC review. No starting dose reductions for Compound AA are planned.

For Arms B and D, the Compound A dose will be reduced; for Arm C, the Compound 1 dose will be reduced. For Arm A, the SRC will determine which of the two drugs in the doublet to dose reduce.

Compound A, Compound 1 and Compound AA will be dosed daily on a continuous basis in 28-day cycles. Compound A dosing may be modified to 5 out of 7 days based on SRC review (the cycle length will remain 28 days). To minimize the risk of tumor lysis syndrome, rituximab, when administered, will be dosed on Day 8 of Cycle 1, then on Day 1 of each subsequent cycle.

After the first dose is administered on Day 1 in any cohort, subjects will be observed for at least 28 days before the next higher protocol-specified dose cohort can begin. Intra-subject dose escalation of study drugs is not permitted during Cycle 1 but may be permitted in later cycles if approved by the SRC. Dose reduction and temporary interruption of one or both drugs due to toxicity is allowed, but dose reduction during Cycle 1 will constitute DLT.

Study treatment may be discontinued if there is evidence of disease progression, unacceptable toxicity or subject/physician decision to withdraw. Subjects may continue to receive study drugs beyond disease progression at the discretion of the Investigator.

The estimated total number of subjects to be enrolled during dose escalation is approximately 36 to 72, depending on cohort size. Approximately 40 to 80 additional subjects (10 to 20 per selected regimen) will be evaluated for safety, PK, PD, and preliminary antitumor effects during the expansion phase.

Subjects will be evaluated for efficacy after every 2 cycles through Cycle 6, every 3 cycles through Cycle 12 and every 6 months thereafter. All treated subjects will be included in the efficacy analyses. The primary efficacy variable is tumor response rate and duration. Tumor response will be determined by the Investigator, based on International Workshop Criteria (IWC) for Malignant Lymphoma (Cheson et al, *J Clin Oncol*, 2007, 25 (5): 579-586).

Secondary and exploratory endpoints include evaluation of Compound A, Compound 1, and Compound AA pharmacodynamic and predictive biomarkers in blood and/or tumor and exploration of PK, PD, toxicity, and activity relationships The safety variables for this study include adverse events (AEs), safety clinical laboratory variables, 12-lead electrocardiograms (ECGs), Eastern Cooperative Oncology Group performance status (ECOG-PS), left ventricular ejection fraction (LVEF) assessments, physical examinations, vital signs, exposure to study treatment, assessment of concomitant medications, and pregnancy testing for females of child bearing potential (FCBP).

During dose escalation, the decision to either evaluate a higher dose level or declare an MTD will be determined by the SRC, based on their review of all available clinical and laboratory safety data for a given dose cohort.

The SRC will also select the dose and schedule and treatment regimens of interest for cohort expansion. One or more regimens may be selected for cohort expansion. The SRC will continue to review safety data regularly throughout the study and make recommendations about study continuation and dose modification, as appropriate.

The steady-state plasma pharmacokinetics of Compound A, Compound 1, the M1 metabolite of Compound 1, and Compound AA will be determined in Arm C. Sparse plasma concentrations of Compound A, Compound 1, and Compound AA will be evaluated after single dose administration of drug combinations and at steady state in all arms (except dose level 2 in Arm C, which will undergo intensive PK monitoring at steady state). Correlations of drug exposure with safety, PD and clinical endpoints may also be explored as an exploratory endpoint.

Pharmacodynamic biomarkers of each novel agent at baseline and on study treatment will be explored, including: 1) Compound A, modulation of CRBN substrates in B and T cells; 2) Compound 1, mTOR signaling pathway biomarkers (p4E-BP1, pAKT, and possibly others); 3) Compound AA, B-cell receptor signaling pathway biomarkers (pBTK, pERK, and possibly others).

Overview of Statistical Methodology.

Statistical analyses will be performed by study phase, treatment arm, and dose level as needed or applicable. All analyses will be descriptive in nature. The efficacy variable of primary interest is tumor response and duration. Other preliminary efficacy variables, including (FDG)-PET outcomes will be summarized using frequency tabulations for categorical variables or descriptive statistics for continuous variables. Efficacy analysis will be repeated for enrolled, treated and efficacy evaluable populations, with the result using treated population considered primary. All summaries of safety data will be conducted using subjects receiving at least one dose of Study Drug (the Safety Population).

All biomarker-related data presentations will be based on treated subjects with at least one baseline and one on-study evaluation (the biomarker evaluable population), unless specified otherwise. Descriptive statistics will be presented for baseline and change from baseline of continuous biomarker endpoints, by treatment arm and overall.

During the dose escalation phase, approximately 36 to 72 subjects will be enrolled. After that, up to 20 subjects may be enrolled in each of the selected cohorts during the dose expansion phase. Since the primary objective of this study is to determine safety/tolerability and MTD/RP2D, an exact sample size for either phase will not be stated in advance.

6.6 Compound Formulations

Illustrative formulations of Compound 1 useful in the methods provided herein are set forth in Tables 1-4, below.

TABLE 1

| Ingredients | Amounts | |
|---|---|---|
| | mg | % w/w |
| Compound 1 | 20.0 | 15.38 |
| Lactose monohydrate, NF (Fast Flo 316) | 63.98 | 49.22 |
| Microcrystalline cellulose, NF (Avicel pH 102) | 40.30 | 31.00 |
| Croscarmellose sodium, NF (Ac-Di-Sol) | 3.90 | 3.00 |
| Stearic acid, NF | 0.52 | 0.40 |
| Magnesium Stearate, NF | 1.30 | 1.00 |
| Total | 130.0 | 100 |
| Opadry yellow 03K12429 | 5.2 | 4.0 |

TABLE 2

| Ingredients | Amounts | |
|---|---|---|
| | mg | % w/w |
| Compound 1 | 5.0 | 3.80 |
| Lactose monohydrate, NF (Fast Flo 316) | 78.98 | 60.70 |
| Microcrystalline cellulose, NF (Avicel pH 102) | 40.30 | 31.00 |
| Croscarmellose sodium, NF (Ac-Di-Sol) | 3.90 | 3.00 |
| Stearic acid, NF | 0.52 | 0.40 |
| Magnesium Stearate, NF | 1.30 | 1.00 |
| Total | 130.0 | 100 |
| Opadry II pink 85F94211 | 5.2 | 4% weight gain |

TABLE 3

| Ingredients | Amounts | | | |
|---|---|---|---|---|
| | mg | | | % w/w |
| Compound 1 | 15.0 | 20.0 | 30.0 | 15.38 |
| Lactose monohydrate, NF (Fast Flo 316) | 48.37 | 64.50 | 96.75 | 49.62 |
| Microcrystalline cellulose, NF (Avicel pH 112) | 30.23 | 40.30 | 60.45 | 31.00 |
| Croscarmellose sodium, NF (Ac-Di-Sol) | 2.925 | 3.90 | 5.85 | 3.00 |
| Magnesium Stearate, NF | 0.975 | 1.30 | 1.95 | 1.00 |
| Total | 97.50 | 130.0 | 195.00 | 100 |
| Opadry yellow 03K12429 | 3.9 | | | 4.0 |
| Opadry II Pink 85F94211 | | 5.2 | | 4.0 |
| Opadry Pink 03K140004 | | | 7.8 | 4.0 |

TABLE 4

| Ingredients | Amounts | |
|---|---|---|
| | mg | % w/w |
| Compound 1 | 45.00 | 15.38 |
| Lactose monohydrate, NF (Fast Flo 316) | 143.955 | 49.22 |
| Microcrystalline cellulose, NF (Avicel pH 102) | 90.675 | 31.00 |
| Croscarmellose sodium, NF (Ac-Di-Sol) | 8.775 | 3.00 |
| Stearic acid, NF | 1.170 | 0.40 |
| Magnesium Stearate, NF | 2.925 | 1.00 |
| Total | 292.50 | 100 |
| Opadry pink 03K140004 | 11.70 | 4.0 |

Illustrative formulations of Compound 2 useful in the methods provided herein are set forth in Table 5, below.

TABLE 5

Exemplary Tablet Formulations

| Ingredients | % w/w (mg) Batch # | | | |
|---|---|---|---|---|
| | 1 | 2 | 3 | 4 |
| Compound 2 (active ingredient) | 10 | 10 | 10 | 10 |
| Mannitol (Mannogem EZ) | qs | qs | qs | qs |
| Microcrystalline Cellulose (PH 112) | 25 | 25 | 25 | 25 |
| Sodium Starch Glycolate | 3 | 3 | 3 | 3 |
| Silicon dioxide | 1 | 1 | 1 | 1 |
| Stearic acid | 0.5 | 0.5 | 0.5 | 0.5 |
| Disodium EDTA | | | 0.5 | 0.5 |
| BHT | | 0.4 | | 0.4 |
| Magnesium Stearate | 0.65 | 0.65 | 0.65 | 0.65 |
| Total | 100 | 100 | 100 | 100 |
| Color | Yellow | Yellow | Yellow | Yellow |

Illustrative formulations of Compound AA useful in the methods provided herein are set forth in Table 6, below.

TABLE 6

Components of N-(3-(5-fluoro-2-(4-(2-methoxyethoxy)phenylamino)-pyrimidin-4-ylamino)phenyl)acrylamide besylate capsules

| Component | First Generation Capsules | | Second Generation Capsules | |
|---|---|---|---|---|
| | Amount per 25 mg | Amount per 125 mg | Amount per 25 mg | Amount per 125 mg |
| Capsule shell | Capsule 1, size 0 dark green capsule | Capsule 1, size 0 white capsule | Capsule 1, size 0 white capsule | Capsule 1, size 0 white capsule |
| N-(3-(5-fluoro-2-(4-(2-methoxyethoxy)phenylamino)pyrimidin-4-ylamino)phenyl) acrylamide besylate | 34.97 mg (25 mg free base) | 174.86 mg (125 mg free base) | 34.97 mg (25 mg free base) | 174.30 mg (125 mg free base) |
| Microcrystalline cellulose | 186.03 mg | 105.27 mg | 186.03 mg | 101.68 mg |
| Lactose monohydrate | 32.50 mg | 41.50 mg | 32.50 mg | 41.50 mg |
| Sodium starch glycolate | 32.50 mg | 41.50 mg | 32.50 mg | 41.50 mg |
| Poloxamer 407 | 32.50 mg | 41.50 mg | 32.50 mg | 41.50 mg |
| Fumed silica | 3.25 mg | 4.15 mg | 3.25 mg | 4.15 mg |
| Magnesium stearate | 3.25 mg† | 6.23 mg˜ | 3.25 mg† | 10.38 mg‡ |

†0.5% (1.625 mg) intragranular; 0.5% (1.625 mg) extragranular.
˜0.5% (2.08 mg) intragranular; 1.0% (4.15 mg) extragranular.
‡2.0% (8.30 mg) intragranular; 0.5% (2.08 mg) extragranular.

A number of references have been cited, the disclosures of which are incorporated herein by reference in their entirety. The embodiments disclosed herein are not to be limited in scope by the specific embodiments disclosed in the examples which are intended as illustrations of a few aspects of the disclosed embodiments and any embodiments that are functionally equivalent are encompassed by the present disclosure. Indeed, various modifications of the embodiments disclosed herein are in addition to those shown and described herein will become apparent to those skilled in the art and are intended to fall within the scope of the appended claims.

What is claimed is:

1. A method for treating diffuse large B-cell lymphoma, comprising administering an effective amount of a TOR kinase inhibitor in combination with an effective amount of N-(3-(5-fluoro-2-(4-(2-methoxyethoxy)phenylamino)pyrimidin-4-ylamino)phenyl)acrylamide, or a pharmaceutically acceptable salt thereof, to a patient having diffuse large B-cell lymphoma, wherein the TOR kinase inhibitor is 7-(6-(2-hydroxypropan-2-yl)-pyridin-3-yl)-1-((1r,4r)-4-methoxycyclohexyl)-3,4-dihydropyrazino-[2,3-b] pyrazin-2(1H)-one or a pharmaceutically acceptable salt, stereoisomer, tautomer or isotopologue thereof.

2. The method of claim 1, wherein the diffuse large B-cell lymphoma is associated with the pathways involving mTOR, PI3K, or Akt kinases and mutants or isoforms thereof.

3. The method of claim 1, wherein the TOR kinase inhibitor is administered in combination with a besylate salt of N-(3-(5-fluoro-2-(4-(2-methoxyethoxy)phenylamino)pyrimidin-4-ylamino)phenyl)acrylamide.

4. The method of claim 1, wherein the TOR kinase inhibitor is administered in combination with the free base of N-(3-(5-fluoro-2-(4-(2-methoxyethoxy)phenylamino)pyrimidin-4-ylamino)phenyl)acrylamide.

5. The method of claim 1, further comprising the administration of an anti-CD20 antibody.

6. The method of claim 5, wherein anti-CD20 antibody is rituximab.

* * * * *